United States Patent
Park et al.

(10) Patent No.: US 8,734,455 B2
(45) Date of Patent: May 27, 2014

(54) HIP RESURFACING SURGICAL GUIDE TOOL

(75) Inventors: Ilwhan Park, Walnut Creek, CA (US);
Michael Koehle, Santa Rosa, CA (US);
Lorenzo R. Deveza, San Ramon, CA (US)

(73) Assignee: OtisMed Corporation, Alameda, CA (US)

(*) Notice: Subject to any disclaimer, the term of this patent is extended or adjusted under 35 U.S.C. 154(b) by 1154 days.

(21) Appl. No.: 12/390,667

(22) Filed: Feb. 23, 2009

(65) Prior Publication Data
US 2009/0222015 A1 Sep. 3, 2009

Related U.S. Application Data

(60) Provisional application No. 61/032,671, filed on Feb. 29, 2008, provisional application No. 61/108,761, filed on Oct. 27, 2008, provisional application No. 61/111,238, filed on Nov. 4, 2008.

(51) Int. Cl.
*A61B 17/58* (2006.01)
*A61B 17/60* (2006.01)
*A61F 2/00* (2006.01)

(52) U.S. Cl.
USPC .............................................. 606/89; 606/96

(58) Field of Classification Search
USPC .............................. 606/79–99; 623/22.11, 22
See application file for complete search history.

(56) References Cited

U.S. PATENT DOCUMENTS

| | | | |
|---|---|---|---|
| 3,195,411 A | 7/1965 | MacDonald et al. |
| 3,825,151 A | 7/1974 | Arnaud |
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,517,969 A | 5/1985 | Halcomb et al. |

(Continued)

FOREIGN PATENT DOCUMENTS

| | | |
|---|---|---|
| DE | 3305237 A1 | 8/1983 |
| DE | 4341367 C1 | 6/1995 |

(Continued)

OTHER PUBLICATIONS

U.S. Appl. No. 12/546,545, filed Aug. 24, 2009, Park et al.

(Continued)

*Primary Examiner* — Sameh Boles
*Assistant Examiner* — Samuel Hanna
(74) *Attorney, Agent, or Firm* — Polsinelli PC

(57) ABSTRACT

Disclosed herein is a tool for guiding a drill hole along a central axis of a femur head and neck for preparation of a femur head that is the subject of a hip resurfacing surgery. In one embodiment, the tool includes a mating region and a guide hole. The mating region is configured to matingly receive a predetermined surface of the femur. The mating region and guide hole are positionally correlated or referenced with each other such that when the mating region matingly receives the predetermined surface of the femur, the guide hole will be generally coaxial with a central axis extending through the femur head and the femur neck.

5 Claims, 35 Drawing Sheets

(56) References Cited

U.S. PATENT DOCUMENTS

| | | |
|---|---|---|
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,098,436 A | 3/1992 | Ferrante et al. |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,768,134 A | 6/1998 | Swaelens et al. |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 | 2/2002 | Hayama et al. |
| 6,382,975 B1 | 5/2002 | Poirier |
| 6,383,228 B1 | 5/2002 | Schmotzer |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |

(56) References Cited

U.S. PATENT DOCUMENTS

| | | | |
|---|---|---|---|
| 7,128,745 B2 | 10/2006 | Masini | |
| D532,515 S | 11/2006 | Buttler et al. | |
| 7,141,053 B2 | 11/2006 | Rose et al. | |
| 7,153,309 B2 | 12/2006 | Huebner et al. | |
| 7,166,833 B2 | 1/2007 | Smith | |
| 7,172,597 B2 | 2/2007 | Sanford | |
| 7,174,282 B2 | 2/2007 | Hollister et al. | |
| 7,184,814 B2 | 2/2007 | Lang et al. | |
| 7,235,080 B2 | 6/2007 | Hodorek | |
| 7,238,190 B2 | 7/2007 | Schon et al. | |
| 7,239,908 B1 | 7/2007 | Alexander et al. | |
| 7,258,701 B2 | 8/2007 | Aram et al. | |
| 7,275,218 B2 | 9/2007 | Petrella et al. | |
| 7,309,339 B2 | 12/2007 | Cusick et al. | |
| 7,340,316 B2 | 3/2008 | Spaeth et al. | |
| 7,359,746 B2 | 4/2008 | Arata | |
| 7,383,164 B2 | 6/2008 | Aram et al. | |
| 7,388,972 B2 | 6/2008 | Kitson | |
| 7,392,076 B2 | 6/2008 | de La Barrera | |
| 7,393,012 B2 | 7/2008 | Funakura et al. | |
| 7,394,946 B2 | 7/2008 | Dewaele | |
| 7,429,346 B2 | 9/2008 | Ensign et al. | |
| 7,468,075 B2 | 12/2008 | Lang et al. | |
| 7,517,365 B2 | 4/2009 | Carignan et al. | |
| 7,534,263 B2 | 5/2009 | Burdulis, Jr. et al. | |
| 7,542,791 B2 | 6/2009 | Mire et al. | |
| 7,547,307 B2 | 6/2009 | Carson et al. | |
| 7,611,519 B2 | 11/2009 | Lefevre et al. | |
| 7,616,800 B2 | 11/2009 | Paik et al. | |
| 7,618,421 B2 | 11/2009 | Axelson, Jr. et al. | |
| 7,618,451 B2 | 11/2009 | Berez et al. | |
| 7,630,750 B2 | 12/2009 | Liang et al. | |
| 7,634,119 B2 | 12/2009 | Tsougarakis et al. | |
| 7,634,306 B2 | 12/2009 | Sarin et al. | |
| 7,641,660 B2 | 1/2010 | Lakin et al. | |
| 7,643,862 B2 | 1/2010 | Schoenefeld | |
| 7,693,321 B2 | 4/2010 | Lehtonen-Krause | |
| 7,702,380 B1 | 4/2010 | Dean | |
| 7,715,602 B2 | 5/2010 | Richard | |
| 7,717,956 B2 | 5/2010 | Lang | |
| D618,796 S | 6/2010 | Cantu et al. | |
| 7,747,305 B2 | 6/2010 | Dean et al. | |
| D619,718 S | 7/2010 | Gannoe et al. | |
| D622,854 S | 8/2010 | Otto et al. | |
| 7,787,932 B2 | 8/2010 | Vilsmeier et al. | |
| 7,794,467 B2 | 9/2010 | McGinley et al. | |
| D626,234 S | 10/2010 | Otto et al. | |
| 7,806,896 B1 | 10/2010 | Bonutti | |
| 7,842,039 B2 | 11/2010 | Hodorek et al. | |
| 7,842,092 B2 | 11/2010 | Otto et al. | |
| 7,881,768 B2 | 2/2011 | Lang et al. | |
| 7,927,335 B2 | 4/2011 | Deffenbaugh et al. | |
| 7,950,924 B2 | 5/2011 | Brajnovic | |
| 7,963,968 B2 | 6/2011 | Dees, Jr. | |
| D642,263 S | 7/2011 | Park | |
| D642,689 S | 8/2011 | Gannoe et al. | |
| 8,007,448 B2 | 8/2011 | Moctezuma de La Barrera | |
| 8,036,729 B2 | 10/2011 | Lang et al. | |
| 8,052,623 B2 | 11/2011 | Haimerl et al. | |
| 8,059,878 B2 | 11/2011 | Feilkas et al. | |
| 8,077,950 B2 | 12/2011 | Tsougarakis et al. | |
| 8,086,336 B2 | 12/2011 | Christensen | |
| D655,008 S | 2/2012 | Gannoe et al. | |
| 8,115,485 B1 | 2/2012 | Maier et al. | |
| 8,126,234 B1 | 2/2012 | Edwards et al. | |
| 8,126,533 B2 | 2/2012 | Lavallee | |
| RE43,282 E | 3/2012 | Alexander et al. | |
| 8,133,234 B2 | 3/2012 | Meridew et al. | |
| 8,142,189 B2 | 3/2012 | Brajnovic | |
| 8,152,855 B2 | 4/2012 | Tulkis et al. | |
| 8,160,345 B2 | 4/2012 | Pavlovskaia et al. | |
| 8,165,657 B2 | 4/2012 | Krueger | |
| 8,170,641 B2 | 5/2012 | Belcher | |
| 8,177,850 B2 | 5/2012 | Rudan et al. | |
| D661,808 S | 6/2012 | Kang | |
| 8,202,324 B2 | 6/2012 | Meulink et al. | |
| 8,214,016 B2 | 7/2012 | Lavallee et al. | |
| 8,221,430 B2 | 7/2012 | Park et al. | |
| 8,224,127 B2 | 7/2012 | Woodard et al. | |
| 8,231,634 B2 | 7/2012 | Mahfouz et al. | |
| 8,234,097 B2 | 7/2012 | Steines et al. | |
| 8,241,293 B2 | 8/2012 | Stone et al. | |
| 8,265,949 B2 | 9/2012 | Haddad | |
| 8,306,601 B2 | 11/2012 | Lang et al. | |
| 8,311,306 B2 | 11/2012 | Pavlovskaia et al. | |
| D672,038 S | 12/2012 | Frey | |
| 8,323,288 B2 | 12/2012 | Zajac | |
| 8,331,634 B2 | 12/2012 | Barth et al. | |
| 8,337,501 B2 | 12/2012 | Fitz et al. | |
| 8,460,302 B2 | 6/2013 | Park et al. | |
| 8,460,303 B2 | 6/2013 | Park | |
| 8,480,679 B2 | 7/2013 | Park | |
| 8,483,469 B2 | 7/2013 | Pavlovskaia et al. | |
| 2002/0087274 A1 | 7/2002 | Alexander et al. | |
| 2002/0160337 A1 | 10/2002 | Klein et al. | |
| 2003/0009167 A1 | 1/2003 | Wozencroft | |
| 2003/0055502 A1 | 3/2003 | Lang et al. | |
| 2003/0176783 A1 | 9/2003 | Hu | |
| 2004/0097952 A1 | 5/2004 | Sarin et al. | |
| 2004/0102792 A1 | 5/2004 | Sarin et al. | |
| 2004/0102866 A1 | 5/2004 | Harris et al. | |
| 2004/0133276 A1 | 7/2004 | Lang et al. | |
| 2004/0138754 A1 | 7/2004 | Lang et al. | |
| 2004/0146369 A1 | 7/2004 | Kato | |
| 2004/0147927 A1 | 7/2004 | Tsougarakis et al. | |
| 2004/0152970 A1 | 8/2004 | Hunter et al. | |
| 2004/0153066 A1 | 8/2004 | Coon et al. | |
| 2004/0153079 A1 | 8/2004 | Tsougarakis et al. | |
| 2004/0153087 A1 | 8/2004 | Sanford et al. | |
| 2004/0204760 A1 | 10/2004 | Fitz et al. | |
| 2004/0220583 A1 | 11/2004 | Pieczynski, II et al. | |
| 2004/0236424 A1* | 11/2004 | Berez et al. | 623/14.12 |
| 2004/0243148 A1 | 12/2004 | Wasielewski | |
| 2004/0243481 A1 | 12/2004 | Bradbury et al. | |
| 2004/0254584 A1 | 12/2004 | Sarin et al. | |
| 2005/0054914 A1 | 3/2005 | Duerk et al. | |
| 2005/0059978 A1 | 3/2005 | Sherry et al. | |
| 2005/0065617 A1 | 3/2005 | de la Barrera et al. | |
| 2005/0080426 A1* | 4/2005 | Qian | 606/96 |
| 2005/0113841 A1 | 5/2005 | Sheldon et al. | |
| 2005/0148843 A1 | 7/2005 | Roose | |
| 2005/0148860 A1 | 7/2005 | Liew et al. | |
| 2005/0192588 A1 | 9/2005 | Garcia | |
| 2005/0201509 A1 | 9/2005 | Mostafavi et al. | |
| 2005/0216024 A1 | 9/2005 | Massoud | |
| 2005/0245934 A1* | 11/2005 | Tuke et al. | 606/79 |
| 2005/0245936 A1 | 11/2005 | Tuke et al. | |
| 2005/0256389 A1 | 11/2005 | Koga et al. | |
| 2005/0267584 A1 | 12/2005 | Burdulis, Jr. et al. | |
| 2005/0272998 A1 | 12/2005 | Diehl et al. | |
| 2006/0015018 A1 | 1/2006 | Jutras et al. | |
| 2006/0015030 A1 | 1/2006 | Poulin et al. | |
| 2006/0015109 A1 | 1/2006 | Haines | |
| 2006/0015188 A1 | 1/2006 | Grimes | |
| 2006/0030853 A1 | 2/2006 | Haines | |
| 2006/0036257 A1 | 2/2006 | Steffensmeier | |
| 2006/0079755 A1 | 4/2006 | Stazzone et al. | |
| 2006/0110017 A1 | 5/2006 | Tsai et al. | |
| 2006/0111628 A1 | 5/2006 | Tsai et al. | |
| 2006/0122491 A1 | 6/2006 | Murray et al. | |
| 2006/0155293 A1 | 7/2006 | McGinley et al. | |
| 2006/0155294 A1 | 7/2006 | Steffensmeier et al. | |
| 2006/0195113 A1 | 8/2006 | Masini | |
| 2006/0244448 A1 | 11/2006 | Ballon et al. | |
| 2006/0271058 A1 | 11/2006 | Ashton et al. | |
| 2006/0293681 A1 | 12/2006 | Claypool et al. | |
| 2007/0005073 A1 | 1/2007 | Claypool et al. | |
| 2007/0010732 A1 | 1/2007 | DeYoe et al. | |
| 2007/0021838 A1 | 1/2007 | Dugas et al. | |
| 2007/0038059 A1 | 2/2007 | Sheffer et al. | |
| 2007/0055268 A1 | 3/2007 | Utz et al. | |
| 2007/0073305 A1 | 3/2007 | Lionberger et al. | |
| 2007/0083266 A1 | 4/2007 | Lang | |
| 2007/0100338 A1 | 5/2007 | Deffenbaugh et al. | |

(56) References Cited

U.S. PATENT DOCUMENTS

| | | |
|---|---|---|
| 2007/0100462 A1 | 5/2007 | Lang et al. |
| 2007/0106389 A1 | 5/2007 | Croxton et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123856 A1 | 5/2007 | Deffenbaugh et al. |
| 2007/0123857 A1 | 5/2007 | Deffenbaugh et al. |
| 2007/0123912 A1 | 5/2007 | Carson |
| 2007/0162039 A1* | 7/2007 | Wozencroft ............... 606/89 |
| 2007/0167833 A1 | 7/2007 | Redel et al. |
| 2007/0173858 A1 | 7/2007 | Engh et al. |
| 2007/0191741 A1 | 8/2007 | Tsai et al. |
| 2007/0198022 A1 | 8/2007 | Lang et al. |
| 2007/0211928 A1 | 9/2007 | Weng et al. |
| 2007/0213738 A1 | 9/2007 | Martin et al. |
| 2007/0219560 A1 | 9/2007 | Hodorek |
| 2007/0226986 A1 | 10/2007 | Chi et al. |
| 2007/0232959 A1 | 10/2007 | Couture et al. |
| 2007/0233136 A1* | 10/2007 | Wozencroft ............... 606/86 |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2007/0282451 A1 | 12/2007 | Metzger et al. |
| 2007/0288030 A1 | 12/2007 | Metzger et al. |
| 2007/0293734 A1 | 12/2007 | Coste-Maniere et al. |
| 2008/0004701 A1 | 1/2008 | Axelson et al. |
| 2008/0015433 A1 | 1/2008 | Alexander et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | D'Alessio et al. |
| 2008/0015607 A1 | 1/2008 | D'Alessio et al. |
| 2008/0021299 A1 | 1/2008 | Meulink |
| 2008/0031412 A1 | 2/2008 | Lang et al. |
| 2008/0033442 A1 | 2/2008 | Amiot et al. |
| 2008/0058613 A1 | 3/2008 | Lang et al. |
| 2008/0088761 A1 | 4/2008 | Lin et al. |
| 2008/0089591 A1 | 4/2008 | Zhou et al. |
| 2008/0114370 A1 | 5/2008 | Schoenefeld |
| 2008/0137926 A1 | 6/2008 | Skinner et al. |
| 2008/0147072 A1 | 6/2008 | Park et al. |
| 2008/0153067 A1 | 6/2008 | Berckmans et al. |
| 2008/0161815 A1 | 7/2008 | Schoenefeld et al. |
| 2008/0195108 A1 | 8/2008 | Bhatnagar et al. |
| 2008/0215059 A1 | 9/2008 | Carignan et al. |
| 2008/0234685 A1 | 9/2008 | Gjerde |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0286722 A1 | 11/2008 | Berckmans, III et al. |
| 2008/0287953 A1 | 11/2008 | Sers |
| 2008/0287954 A1* | 11/2008 | Kunz et al. ............... 606/87 |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0085567 A1 | 4/2009 | Kimmlingen et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0093816 A1 | 4/2009 | Roose et al. |
| 2009/0110498 A1 | 4/2009 | Park |
| 2009/0112213 A1 | 4/2009 | Heavener et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0157083 A1 | 6/2009 | Park et al. |
| 2009/0163923 A1 | 6/2009 | Flett et al. |
| 2009/0209884 A1 | 8/2009 | Van Vorhis et al. |
| 2009/0222014 A1 | 9/2009 | Bojarski et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0234217 A1 | 9/2009 | Mire et al. |
| 2009/0248044 A1 | 10/2009 | Amiot et al. |
| 2009/0254093 A1* | 10/2009 | White et al. ............... 606/89 |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0285465 A1 | 11/2009 | Haimerl et al. |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0016986 A1* | 1/2010 | Trabish ............... 623/23.14 |
| 2010/0023015 A1 | 1/2010 | Park |
| 2010/0042105 A1 | 2/2010 | Park et al. |
| 2010/0049195 A1 | 2/2010 | Park et al. |
| 2010/0087829 A1 | 4/2010 | Metzger et al. |
| 2010/0099977 A1 | 4/2010 | Hershberger |
| 2010/0145344 A1 | 6/2010 | Jordan et al. |
| 2010/0152741 A1 | 6/2010 | Park et al. |
| 2010/0153076 A1 | 6/2010 | Bellettre et al. |
| 2010/0153081 A1 | 6/2010 | Bellettre et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0185202 A1 | 7/2010 | Lester et al. |
| 2010/0191242 A1 | 7/2010 | Massoud |
| 2010/0191244 A1 | 7/2010 | White et al. |
| 2010/0198351 A1 | 8/2010 | Meulink |
| 2010/0209868 A1 | 8/2010 | De Clerck |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0256479 A1 | 10/2010 | Park et al. |
| 2010/0262150 A1 | 10/2010 | Lian |
| 2010/0274253 A1 | 10/2010 | Ure |
| 2010/0274534 A1 | 10/2010 | Steines et al. |
| 2010/0292963 A1 | 11/2010 | Schroeder |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0324692 A1 | 12/2010 | Uthgenannt et al. |
| 2010/0329530 A1 | 12/2010 | Lang et al. |
| 2010/0332194 A1 | 12/2010 | McGuan et al. |
| 2011/0015636 A1 | 1/2011 | Katrana et al. |
| 2011/0016690 A1 | 1/2011 | Narainasamy et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0046735 A1 | 2/2011 | Metzger et al. |
| 2011/0054486 A1 | 3/2011 | Linder-Ganz et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071537 A1 | 3/2011 | Koga et al. |
| 2011/0071581 A1 | 3/2011 | Lang et al. |
| 2011/0071645 A1 | 3/2011 | Bojarski et al. |

(56) References Cited

U.S. PATENT DOCUMENTS

| | | |
|---|---|---|
| 2011/0071802 A1 | 3/2011 | Bojarski et al. |
| 2011/0087332 A1 | 4/2011 | Bojarski et al. |
| 2011/0087465 A1 | 4/2011 | Mahfouz |
| 2011/0092804 A1 | 4/2011 | Schoenefeld et al. |
| 2011/0092977 A1 | 4/2011 | Salehi et al. |
| 2011/0092978 A1 | 4/2011 | McCombs |
| 2011/0093108 A1 | 4/2011 | Ashby et al. |
| 2011/0106093 A1 | 5/2011 | Romano et al. |
| 2011/0112808 A1 | 5/2011 | Anderson et al. |
| 2011/0144760 A1 | 6/2011 | Wong et al. |
| 2011/0160736 A1 | 6/2011 | Meridew et al. |
| 2011/0166578 A1 | 7/2011 | Stone et al. |
| 2011/0166666 A1 | 7/2011 | Meulink et al. |
| 2011/0172672 A1 | 7/2011 | Dubeau et al. |
| 2011/0184526 A1 | 7/2011 | White et al. |
| 2011/0190899 A1 | 8/2011 | Pierce et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park |
| 2011/0218539 A1 | 9/2011 | Fitz et al. |
| 2011/0218542 A1 | 9/2011 | Lian |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0268248 A1 | 11/2011 | Simon et al. |
| 2011/0270072 A9 | 11/2011 | Feilkas et al. |
| 2011/0276145 A1 | 11/2011 | Carignan et al. |
| 2011/0282473 A1 | 11/2011 | Pavlovskaia et al. |
| 2011/0295329 A1 | 12/2011 | Fitz et al. |
| 2011/0295378 A1 | 12/2011 | Bojarski et al. |
| 2011/0305379 A1 | 12/2011 | Mahfouz |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0004725 A1 | 1/2012 | Shterling et al. |
| 2012/0029520 A1 | 2/2012 | Lang et al. |
| 2012/0041446 A1 | 2/2012 | Wong et al. |
| 2012/0053591 A1 | 3/2012 | Haines et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0130434 A1 | 5/2012 | Stemniski |
| 2012/0143197 A1 | 6/2012 | Lang et al. |
| 2012/0143198 A1 | 6/2012 | Boyer et al. |
| 2012/0150243 A9 | 6/2012 | Crawford et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165820 A1 | 6/2012 | De Smedt et al. |
| 2012/0165821 A1 | 6/2012 | Carignan et al. |
| 2012/0172882 A1 | 7/2012 | Sato |
| 2012/0179147 A1 | 7/2012 | Geebelen et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0221008 A1 | 8/2012 | Carroll et al. |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0265499 A1 | 10/2012 | Mahfouz et al. |
| 2012/0310400 A1 | 12/2012 | Park et al. |
| 2013/0039551 A1 | 2/2013 | Pavlovskaia et al. |
| 2013/0115474 A1 | 5/2013 | Park |
| 2013/0116697 A1 | 5/2013 | Park et al. |
| 2013/0123789 A1 | 5/2013 | Park |

FOREIGN PATENT DOCUMENTS

| | | |
|---|---|---|
| DE | 102005023028 A1 | 11/2006 |
| EP | 0097001 A | 12/1983 |
| EP | 0574098 A | 12/1993 |
| EP | 0622052 A | 11/1994 |
| EP | 0908836 A2 | 4/1999 |
| EP | 0908836 A3 | 12/1999 |
| EP | 1059153 A2 | 12/2000 |
| EP | 1486900 A1 | 12/2004 |
| EP | 1532939 A1 | 5/2005 |
| GB | 2215610 A1 | 9/1989 |
| GB | 2420717 A | 6/2006 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 01/00096 A1 | 1/2001 |
| WO | WO 01/70142 A1 | 9/2001 |
| WO | WO 01/85040 A1 | 11/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |

OTHER PUBLICATIONS

U.S. Appl. No. 12/563,809, filed Sep. 21, 2009, Park et al.
U.S. Appl. No. 10/146,862, filed May 15, 2002, Park et al.
U.S. Appl. No. 29/296,687, filed Oct. 25, 2007, Park.
U.S. Appl. No. 12/111,924, filed Apr. 29, 2008, Park et al.
U.S. Appl. No. 12/391,008, filed Feb. 23, 2009, Park et al.
U.S. Appl. No. 12/386,105, filed Apr. 14, 2009, Pavlovskaia et al.
U.S. Appl. No. 12/505,056, filed Jul. 17, 2009, Park.
Advisory Action, U.S. Appl. No. 11/642,385, dated Oct. 29, 2010, 3 pages.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action, U.S. Appl. No. 11/656,323, filed Jun. 25, 2010, 7 pages.
Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.

(56) References Cited

OTHER PUBLICATIONS

Amendment and Response, U.S. Appl. No. 11/642,385, filed May 28, 2010, 11 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Final Office Action and PTO-892, U.S. Appl. No. 11/641,382, mailed Aug. 5, 2010, 13 pages.
Final Office Action and PTO-892, U.S. Appl. No. 11/656,323, mailed Sep. 3, 2010, 11 pages.
Final Office Action, U.S. Appl. No. 11/641,569, mailed May 10, 2010, 9 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2011/032342, dated Jul. 1, 2011, 8 pages.
Non-Final Office Action and PTO-892, U.S. Appl. No. 11/641,382, mailed Jan. 20, 2010, 12 pages.
NonFinal Office Action and PTO-892, U.S. Appl. No. 11/642,385, mailed Mar. 2, 2010, 11 pages.
Non-Final Office Action and PTO-892, U.S. Appl. No. 11/656,323, mailed Mar. 30, 2010, 10 pages.
Nonfinal Office Action, U.S. Appl. No. 11/959,344, dated Feb. 15, 2011, 29 pages.
Notice of Allowance, U.S. Appl. No. 29/296,687, mailed Mar. 31, 2011, 18 pages.
Notice of Non-Compliant Amendment, U.S. Appl. No. 11/641,569, mailed Aug. 7, 2009, 3 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
Response to Notice of Non-Complaint Amendment, U.S. Appl. No. 11/641,569, dated Aug. 19, 2009, 11 pages.
Response to Restriction Requirement U.S. Appl. No. 29/296,687, filed Oct. 7, 2010, 3 pages.
Response to Restriction Requirement, U.S. Appl. No. 11/959,344, filed Nov. 24, 2010, 13 pages.
Restriction Requirement, U.S. Appl. No. 11/959,344, dated Oct. 29, 2010, 6 pages.
Restriction Requirement, U.S. Appl. No. 29/296,687, mailed Sep. 21, 2010, 7 pages.
Akca, "Matching of 3D Surfaces and Their Intensities," ISPRS Journal of Photogrammetry & Remote Sensing, 62(2007), 112-121.
Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.
Bargar et al., "Robotic Systems in Surgery," Orthopedic and Spine Surgery, Surgical Technology International II, 1993, 419-423.
Besl et al., "A Method for Registration of 3-D Shapes," IEEE Transactions on Pattern Analysis and Machine Intelligence (PAMI), 14(2):239-256, Feb. 1992.
Blaha et al., "Using the Transepicondylar Axis to Define the Sagittal Morphology of the Distal Part of the Femur," J Bone Joint Surg Am. 2002;84-A Suppl 2:48-55.
Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.
Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.
Canny, "A computational Approach to Edge Detection," IEEE Transactions on Pattern Analysis and Machine Intelligence, PAMI 8(6), pp. 679-698 (1986).
Churchill et al., "The Transepicondylar Axis Approximates the Optimal Flexion Axis of the Knee," Clin Orthop Relat Res. 1998(356):111-8.
Cicuttini et al., "Gender Differences in Knee Cartilage Volume as Measured by Magnetic Resonance Imaging," Osteoarthritis Cartilage 1999, 7:265-71.
Cicuttini et al., "Longitudinal Study of the Relationship Between Knee angle and Tibiofemoral cartilage Volume in Subjects with Knee Osteoarthritis," Rheumatology (Oxford) 2004, 43:321-4.
Eckhoff et al., "Difference Between the Epicondylar and Cylindrical Axis of the Knee," Clin Orthop Relat Res. 2007;461:238-44.
Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).
Eisenhart-Rothe et al., "The Role of Knee alignment in Disease Progression and Functional Decline in Knee Osteoarthritis," JAMA 2001, 286:188-95.
Elias et al., "A Correlative Study of the Geometry and anatomy of the Distal Femur," Clin orthop Relat Res. 1990(260):98-103.
Favorito et al., "total Knee Arthroplasty in the Valgus Knee," Journal Am Acad Orthop surg. 2002;10(1):16-24.
Freeman et al., "The Movement of the Knee Studied by Magnetic Resonance Imaging," Clinical orthop Relat Res. 2003(410):35-43.
Freeman et al., "The movement of the Normal Tibio-Femoral Joint," Journal Biomech. 2005;38(2):197-208.
Graichen et al., "quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.
Gruen et al., "least Squares 3D Surface and Curve Matching," ISPRS Journal of Photogrammetry & Remote Sensing, 59(2005), 151-174.
Hollister et al., "The Axes of Rotation of the Knee," Clin Orthop Relat Res. 1993(290):259-68.
Howell et al., "Longitudinal Shapes of the Tibia and Femur are Unrelated and Variable," Clinical Orthopaedics and Related Research (2010) 468: 1142-1148.
Howell et al., "Results of an Initial Experience with Custom-Fit Positioning Total Knee Arthroplasty in a Series of 48 Patients," Orthopedics, 2008;31(9):857-63.
Howell et al., "In Vivo Adduction and Reverse Axial Rotation (External) of the Tibial Component can be Minimized During Standing and Kneeling," Orthopedics, In Press.
Iwaki et al., "Tibiofemoral Movement 1: The Shapes and Relative Movements of the Femur and Tibia in the Unloaded Cadaver Knee," Journal Bone Joint Surg Br. 2000;82(8):1189-95.
Jacobs et al., "Hip Resurfacing Through an Anterolateral Approach," J. Bone Joint Surg Am. 2008:90 Suppl 3:38-44.
Johnson, "Joint Remodeling as the Basis for Osteoarthritis," Journal Am Vet Med Assoc. 1962, 141:1233-41.
Kass et al., "Active Contour Models, International Journal of Computer Vision," pp. 321-331 (1988).
Kellgren et al., "Radiological Assessment of Osteoarthrosis," Ann Rheum Dis 1957, 10:494-501.
Kessler et al, "Sagittal Curvature of Total Knee Replacements Predicts in vivo Kinematics," Clin Biomech (Bristol, Avon) 2007; 22(1):52-8.
Kienzel III et al., "Total Knee Replacement," IEEE May/Jun. 1995.
Kienzel III et al., "An Integrated CAD-Robotics System for Total Knee Replacement Surgery", IEEE International Conference, pp. 889-894, vol. 1, May 1993.
Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.

(56) References Cited

OTHER PUBLICATIONS

Krackow et al., "Primary Total Knee Arthroplasty in Patients with Fixed Valgus Deformity," Clin Orthop Relat Res. 1991(273):9-18.
Krackow, "Approaches to Planning lower Extremity alignment for Total Knee arthroplasty and Osteotomy About the Knee," adv Orthop surg 7:69, 1983.
Lea et al., "Registration and immobilization in robot-assisted surgery", Journal of Image Guided Surgery, pp. 1-10, 1995.
Manner et al., "Knee Deformity in Congenital Longitudinal Deficiencies of the Lower Extremity," Clin Orthop Relat Res. 2006;448:185-92.
Matsuda et al, "Anatomical Analysis of the Femoral Condyle in Normal and Osteoarthritic Knees," Journal Orthopaedic Res. 2004;22(1):104-9.
Matsuda et al., "Femoral Condyle Geometry in the Normal and Varus Knee," Clinical Orthop Relat Res. 1998(349):183-8.
Messmer et al., "Volumetric Determination of the Tibia Based on 2d Radiographs Using a 2d/3d Database", Dept. of Surgery, Trauma Unit, University Hospital, Bassel, Switzerland, *Computer Aided Surgery* 6:183-194 (2001).
Mihalko et al., The Variability of Intramedullary Alignment of the Femoral Component During Total Knee Arthroplasty, Journal Arthroplasty. 2005;20(1):25-8.
Morvan et al., IVECS, Interactively Correcting .STL Files in a Virtual Environment, Clemson University, Clemson, SC, Proc. Conf. Virtual Design, Aug. 1996.
Naoki Kusumoto, Taiji et al., "Application of Virtual Reality Force Feedback Haptic Device for Oral Implant Surgery", Graduate School of Dentistry Course for Integrated Oral Science and Stomatology, Jun. 16, 2005.
Panjabi et al., "Errors in Kinematic Parameters of a Planar Joint: Guidelines for Optimal Experimental Design," Journal Biomech. 1982;15(7):537-44.
Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.
Peterfy et al., "Quantification of articular Cartilage in the Knee with Pulsed Saturation Transfer Subtraction and Fact-Suppressed MR Imaging: Optimization and Validation," Radiology 1994, 192:485-91.
Pinskerova et al., "The Shapes and Relative Movements of the Femur and Tibia at the Knee," Orthopaedics 2000;29 Suppl 1:S3-5.
Rosset et al., "General Consumer Communication Tools for Improved Image Management and Communication in Medicine," Journal Digital Imaging, 2005;18(4):270-9.
Shakespeare D., "Conventional Instruments in Total Knee Replacement: What Should We Do With Them?" Knee. 2006;13(1):1-6.
Shepstone et al., "The shape of the Distal Femur: A Palaeopathological Comparison of Eburnated and Non-Eburnated Femora," Ann. Rheum Dis. 1999, 58:72-8.
Siston et al., "The Variability of Femoral Rotational Alignment in Total Knee Arthroplasty," Journal Bone Joint Surg Am. 2005;87(10):2276-80.
Siston et al., "Averaging Different Alignment Axes Improves Femoral Rotational Alignment in Computer-Navigated Total Knee Arthroplasty," Journal Bone Joint Surg Am. 2008;90(10):2098-104.
Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.
Spencer et al., "Initial Experience with Custom-Fit Total Knee Replacement: Intra-operative Events and Long-Leg Coronal alignment," International Orthopaedics (SICOT), 2009:In Press.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.

Teeny et al., "Primary Total Knee Arthroplasty in Patients with Severe Varus Deformity. A Comparative Study," Clin Orthop Relat Res. 1991(273):19-31.
Wright Medical Technology, Inc., "Prophecy Pre-Operative Naviation Guides Surgical Technique," 2009.
International Search Report and Written Opinion, International Application No. PCT/US2009/040629, mailed Aug. 6, 2009, 9 pages.
Restriction Requirement, U.S. Appl. No. 11/641,382, mailed Sep. 3, 2009, 6 pages.
Restriction Requirement, U.S. Appl. No. 11/642,385, mailed Oct. 27, 2009, 7 pages.
International Search Report and Written Opinion, International Application No. PCT/US2009/051109, mailed Nov. 6, 2009, 13 pages.
NonFinal Office Action, U.S. Appl. No. 11/641,569, mailed Nov. 12, 2009, 9 pages.
Restriction Requirement, U.S. Appl. No. 11/656,323, mailed Nov. 13, 2009, 10 pages.
International Search Report and Written Opinion, PCT/US2007/001624, dated Dec. 12, 2007, 14 pages.
Invitation to Pay Additional Fees mailed on Jul. 31, 2007, for PCT Application No. PCT/US2007/001624 filed on Jan. 19, 2007, 5 pages.
International Search Report and Written Opinion, PCT/US2007/001622, dated Jun. 11, 2007, 14 pages.
Office Action, U.S. Appl. No. 10/146,862, mailed Jan. 13, 2005, 10 pages.
Amendment and Response to Office Action and Petition to Revive, U.S. Appl. No. 10/146,862, filed Jan. 18, 2006, 29 pages.
Restriction Requirement, U.S. Appl. No. 11/641,569, mailed Apr. 27, 2009, 7 pages.
International Search Report and Written Opinion, PCT/US2008/083125, dated Mar. 9, 2009, 13 pages.
International Search Report and Written Opinion, International Application No. PCT/US2009/34983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
Akenine-Möller et al., Real-Time Rendering, Second Edition, AK Peters, Natick, MA, 6 pages (Table of Contents), 2002.
Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.
Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.
Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.
Barequet et al., "Filling Gaps in the Boundary of a Polyhedron," Computer Aided Geometric Design, vol. 12, pp. 207-229, 1995.
Barequet et al., "Repairing CAD Models," Proceedings of the 8th IEEE Visualization '97 Conference, pp. 363-370, Oct. 1997.
Berry et al., "Personalised image-based templates for intra-operative guidance," Proc. Inst. Mech. Eng. Part H: J. Engineering in Medicine, vol. 219, pp. 111-118, Oct. 7, 2004.
Biščević et al., "Variations of Femoral Condyle Shape," Coll. Antropol., vol. 29 No. 2, pp. 409-414, 2005.
Blinn, Jim Blinn's Corner—A Trip Down the Graphics Pipeline, Morgan Kaufmann Publishers, Inc., San Francisco, CA, 5 pages (Table of Contents), 1996.

(56) References Cited

OTHER PUBLICATIONS

Boøhn et al., "A Topology-Based Approach for Shell-Closure," Geometric Modeling for Product Realization (P.R. Wilson et al. editors), pp. 297-319, Elsevier Science Publishers B.V., North-Holland, 1993.
Chauhan et al., "Computer-assisted knee arthroplasty versus a conventional jig-based technique—a randomised, prospective trial," The Journal of Bone and Joint Surgery, vol. 86-B, No. 3, pp. 372-377, Apr. 2004.
Cohen et al., Radiosity and Realistic Image Synthesis, Academic Press Professional, Cambridge, MA, 8 pages (Table of Contents), 1993.
Couglin et al., "Tibial Axis and Patellar Position Relative to the Femoral Epicondylar Axis During Squatting," The Journal of Arthroplasty, vol. 18, No. 8, Elsevier, 2003.
Delp et al., "Computer Assisted Knee Replacement," Clinical Orthopaedics and Related Research, No. 354, pp. 49-56, Sep. 1998.
Dutréet al., Advanced Global Illumination, AK Peters, Natick, MA, 5 pages (Table of Contents), 2003.
Eckhoff et al., "Three-Dimensional Mechanics, Kinematics, and Morphology of the Knee Viewed in Virtual Realty," The Journal of Bone and Joint Surgery, vol. 87-A, Supplement 2, pp. 71-80, 2005.
Erikson, "Error Correction of a Large Architectural Model: The Henderson County Courthouse," Technical Report TR95-013, Dept. of Computer Science, University of North Carolina at Chapel Hill, pp. 1-11, 1995.
Ervin et al., Landscape Modeling, McGraw-Hill, New York, NY, 8 pages (Table of Contents), 2001.
Farin, Nurb Curves and Surfaces: From Projective Geometry to Practical Use, AK Peters, Wellesley, MA, 7 pages. (Table of Contents), 1995.
Fleischer et al., "Accurate Polygon Scan Conversion Using Half-Open Intervals," Graphics Gems III, pp. 362-365, code: pp. 599-605, 1992.
Foley et al., Computer Graphics: Principles and Practice, Addison-Wesley Publishing Company, Reading, MA, 9 pages (Table of Contents), 1990.
Glassner (editor), An Introduction to Ray Tracing, Academic Press Limited, San Diego, CA, 4 pages (Table of Contents), 1989.
Glassner, Principles of Digital Image Synthesis, vols. One and Two, Morgan Kaufmann Publishers, Inc., San Francisco, CA, 32 pages (Tables of Contents), 1995.
Gooch et al., Non-Photorealistic Rendering, AK Peters, Natick, MA, 4 pages (Table of Contents), 2001.
Grüne et al., "On numerical algorithm and interactive visualization for optimal control problems," Journal of Computation and Visualization in Science, vol. 1, No. 4, pp. 221-229, Jul. 1999.
Guéziec et al., "Converting Sets of Polygons to Manifold Surfaces by Cutting and Stitching," Proc. IEEE Visualization 1998, pp. 383-390, Oct. 1998.
Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: Fact and Fiction Syllabus, San Diego, CA, 8 pages, Oct. 20-22, 2005 (best available copy).
Hafez et al., "Computer Assisted Total Knee Replacement: Could a Two-Piece Custom Template Replace the Complex Conventional Instrumentations?", Computer Aided Surgery, vol. 9, No. 3, pp. 93-94, 2004.
Hafez et al., "Computer-Assisted Total Knee Arthroplasty Using Patient-Specific Templating," Clinical Orthopaedics and Related Research, No. 0, pp. 1-9, 2006.
Jensen, Realistic Image Synthesis Using Photon Mapping, AK Peters, Natick, MA, 7 pages (Table of Contents), 2001.
Jones et al., "A new approach to the construction of surfaces from contour data," Computer Graphics Forum, vol. 13, No. 3, pp. 75-84, 1994 [ISSN 0167-7055].
Khorramabadi, "A Walk Through the Planned CS Building," Technical Report UCB/CSD 91/652, Computer Science Department, University of California at Berkeley, 74 pages, 1991.
Kidder et al., "3-D Model Acquisition, Design, Planning and Manufacturing of Orthopaedic Devices: A Framework," Advanced Sensor and Control-System Interface (B.O. Nnaji editor), Proceedings SPIE—The International Society for Optical Engineering, Bellingham, WA, vol. 2911, pp. 9-22, Nov. 21-22, 1996.
Kumar, Robust Incremental Polygon Triangulation for Surface Rendering, Center for Geometric Computing, Department of Computer Science, Johns Hopkins University, Baltimore, Md, WSCG, the International Conference in Central Europe on Computer Graphics, Visualization and Computer Vision, pp. 381-388, 2000.
Kunz et al., "Computer Assisted Hip Resurfacing Using Individualized Drill Templates," The Journal of Arthroplasty, vol. 00, No. 0, pp. 1-7, 2009.
Lorensen et al., "Marching Cubes: A High Resolution 3d Surface Construction Algorithm," Computer Graphics, vol. 21, No. 4, pp. 163-169, 1987.
Nooruddin et al., Simplification and Repair of Polygonal Models Using Volumetric Techniques, IEEE Transactions on Visualization and Computer Graphics, vol. 9, No. 2, pp. 191-205, Apr.-Jun. 2003.
Pharr et al., Physically Based Rendering, from Theory to Implementation, Morgan Kaufmann Publishers, San Francisco, CA, 13 pages (Table of Contents), 2004.
Platt et al., "Mould Arthroplasty of the Knee, A Ten-Year Follow-up Study," The Journal of Bone and Joint Surgery (British Volume), vol. 51-B, No. 1, pp. 76-87, Feb. 1969.
Potter, "Arthroplasty of the Knee with Tibial Metallic Implants of the McKeever and MacIntosh Design," The Surgical Clinics of North America, vol. 49, No. 4, pp. 903-915, Aug. 1969.
Radermacher et al., "Computer Assisted Orthopaedic Surgery with Image Based Individual Templates," Clinical Orthopaedics and Related Research, vol. 354, pp. 28-38, Sep. 1998.
Rohlfing et al., "Quo Vadis, Atlas-Based Segmentation?", The Handbook of Medical Image Analysis: Segmentation and Registration Models (Kluwer), pp. 1-55, (http://www.stanford.edu/~rohlfing/publications/2005-rohlfing-chapter-quo_vadis_atlas_based_segmentation.pdf).
Shirley et al., Realistic Ray Tracing, Second Edition, AK Peters, Natick, MA, 7 pages (Table of Contents), 2003.
Strothotte et al., Non-Photorealistic Computer Graphics—Modeling, Rendering, and Animation, Morgan Kaufmann Publishers, San Francisco, CA, 9 pages (Table of Contents), 2002.
Vande Berg et al., "Assessment of Knee Cartilage in Cadavers with Dual-Detector Spiral CT Arthrography and MR Imaging," Radiology, vol. 222, No. 2, pp. 430-436, Feb. 2002.
Wikipedia, the Free Encyclopedia, "CNC," (date unknown) located at http://en.wikipedia.org/wiki/CNC>, 6 pages last visited on Apr. 12, 2007.
Final Office Action, U.S. Appl. No. 11/959,344, mailed Oct. 27, 2011, 12 pages.
Non-Final Office Action, U.S. Appl. No. 11/641,569, dated Aug. 3, 2011, 14 pages.
Non-Final Office Action, U.S. Appl. No. 12/391,008, mailed Oct. 31, 2011, 44 pages.
Notice of Allowance, U.S. Appl. No. 13/066,568, mailed Oct. 26, 2011, 28 pages.
Response to Restriction Requirement, U.S. Appl. No. 12/391,008, filed Aug. 29, 2011, 9 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 12/386,105, dated Oct. 24, 2011, 7 pages.
Restriction Requirement, U.S. Appl. No. 12/391,008, dated Aug. 18, 2011, 6 pages.
Final Office Action, U.S. Appl. No. 11/641,569, mailed Mar. 1, 2012, 12 pages.
Non-Final Office Action, U.S. Appl. No. 12/386,105, dated Feb. 9, 2012, 30 pages.

(56) References Cited

OTHER PUBLICATIONS

Notice of Allowance, U.S. Appl. No. 11/959,344, mailed Mar. 5, 2012, 13 pages.
Office Action (Restriction Requirement), U.S. Appl. No. 12/563,809, dated Feb. 2, 2012, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Restriction Requirement, U.S. Appl. No. 12/563,809, filed Feb. 24, 2012, 10 pages.
U.S. Appl. No. 13/374,960, filed Jan. 25, 2012, Pavlovskaia et al.
Response to Non-Final Office Action, U.S. Appl. No. 11/641,569, filed Dec. 2, 2011, 7 pages.
Non-Final Office Action, U.S. Appl. No. 11/946,002, dated Nov. 25, 2011, 44 pages.
Response to Restriction Requirement, U.S. Appl. No. 12/386,105, filed Dec. 21, 2011, 9 pages.
Response to Final Office Action, U.S. Appl. No. 11/959,344, filed Dec. 27, 2011, 16 pages.
Non-Final Office Action, U.S. Appl. No. 11/924,425, mailed Jan. 25, 2012, 35 pages.
Final Office Action, U.S. Appl. No. 11/641,382, mailed Jul. 25, 2012, 12 pages.
Final Office Action, U.S. Appl. No. 11/924,425, mailed Jul. 6, 2012, 14 pages.
Non-Final Office Action, U.S. Appl. No. 12/111,924, mailed Jun. 29, 2012, 35 pages.
Non-Final Office Action, U.S. Appl. No. 12/546,545, mailed Jul. 19, 2012, 28 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 12/386,105, mailed Jul. 5, 2012, 11 pages.
RCE/Amendment, U.S. Appl. No. 11/946,002, filed Sep. 6, 2012, 38 pages.
Response to Final Office Action, U.S. Appl. No. 11/641,569, filed Jun. 28, 2012, 10 pages.
Response to Final Office Action, U.S. Appl. No. 11/924,425, filed Sep. 5, 2012, 9 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Restriction, U.S. Appl. No. 12/563,809, filed Aug. 6, 2012, 10 pages.
Restriction Requirement, U.S. Appl. No. 12/563,809, mailed Jul. 6, 2012, 6 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Non-Final Office Action, U.S. Appl. No. 11/641,382, mailed Mar. 29, 2012, 24 pages.
Response to Non-Final Office Action, U.S. Appl. No. 11/924,425, filed Apr. 25, 2012, 8 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Restriction Requirement, U.S. Appl. No. 12/111,924, mailed Mar. 19, 2012, 8 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/636,939, mailed Apr. 13, 2012, 6 pages.
U.S. Appl. No. 13/573,662, filed Oct. 2, 2012, Pavlovskaia et al.
U.S. Appl. No. 13/723,904, filed Dec. 21, 2012, Park.
U.S. Appl. No. 13/730,467, filed Dec. 28, 2012, Park et al.
U.S. Appl. No. 13/730,585, filed Dec. 28, 2012, Park et al.
U.S. Appl. No. 13/730,608, filed Dec. 28, 2012, Park et al.
U.S. Appl. No. 13/731,697, filed Dec. 31, 2012, Pavlovskaia et al.
U.S. Appl. No. 13/731,850, filed Dec. 31, 2012, Park.
U.S. Appl. No. 13/749,095, filed Jan. 24, 2013, Song.
Amendment Under 37 C.F.R. 1.312, U.S. Appl. No. 12/386,105, filed Oct. 1, 2012, 6 pages.
Appeal Brief, U.S. Appl. No. 12/391,008, filed Oct. 16, 2012, 24 pages.
Examiner's Answer in appeal, U.S. Appl. No. 12/391,008, mailed Dec. 13, 2012, 27 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Howell et al., "In Vivo Adduction and Reverse Axial Rotation (External) of the Tibial Component can be Minimized During Standing and Kneeling," Orthopedics|ORTHOSupersite.com vol. 32 No. 5, 319-326 (May 2009).
Non-Final Office Action, U.S. Appl. No. 11/641,569, dated Jan. 3, 2013, 12 pages.
Non-Final Office Action, U.S. Appl. No. 13/086,275, mailed Feb. 7, 2013, 36 pages.
Non-Final Office Action, U.S. Appl. No. 12/563,809, mailed Sep. 21, 2012, 32 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 29/394,882, mailed Feb. 4, 2013, 32 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.
Notice of Allowance, U.S. Appl. No. 13/374,960, mailed Nov. 2, 2012, 24 pages.
Response to Final Office Action, U.S. Appl. No. 12/546,545, filed Feb. 20, 2013, 13 pages.
Response to Final Office Action, U.S. Appl. No. 11/641,382, filed Sep. 24, 2012, 11 pages.
Response to Non-Final Office Action, U.S. Appl. No. 12/563,809, filed Dec. 13, 2012, 15 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
U.S. Appl. No. 13/923,093, filed Jun. 20, 2013, Park.
U.S. Appl. No. 13/960,498, filed Aug. 6, 2013, Song.
Amendment Under 37 C.F.R. 1.312, U.S. Appl. No. 13/374,960, filed May 7, 2013, 6 pages.
Final Office Action, U.S. Appl. No. 12/563,809, mailed Mar. 7, 2013, 14 pages.
Non-Final Office Action, U.S. Appl. No. 11/641,569, mailed Jul. 12, 2013, 21 pages.
Non-Final Office Action, U.S. Appl. No. 12/505,056, mailed Jun. 28, 2013, 7 pages.

(56) References Cited

OTHER PUBLICATIONS

Non-Final Office Action, U.S. Appl. No. 12/546,545, mailed Mar. 13, 2013, 10 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/730,585, mailed Jun. 11, 2013, 10 pages.
Notice of Allowance, U.S. Appl. No. 29/394,882, mailed May 24, 2013, 16 pages.
Notice of Allowance, U.S. Appl. No. 12/111,924, mailed Mar. 11, 2013, 14 pages.
Notice of Allowance, U.S. Appl. No. 12/563,809, mailed May 28, 2013, 11 pages.
Notice of Allowance, U.S. Appl. No. 13/374,960, mailed May 6, 2013, 20 pages.
Notice of Allowance, U.S. Appl. No. 13/573,662, mailed Mar. 19, 2013, 34 pages.
Preliminary Amendment, U.S. Appl. No. 13/731,697, filed May 10, 2013, 6 pages.
Response to Final Office Action, U.S. Appl. No. 12/563,809, filed May 6, 2013, 15 pages.
Response to Final Office Action, U.S. Appl. No. 12/636,939, filed Apr. 8, 2013, 10 pages.
Response to Non-Final Office Action, U.S. Appl. No. 11/641,569, filed Apr. 3, 2013, 9 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Restriction Requirement, U.S. Appl. No. 12/760,388, filed Apr. 5, 2013, 7 pages.
Restriction Requirement, U.S. Appl. No. 12/760,388, mailed Mar. 6, 2013, 7 pages.
Final Office Action, U.S. Appl. No. 11/641,569, dated Nov. 29, 2013, 20 pages.
Final Office Action, U.S. Appl. No. 12/546,545, dated Oct. 7, 2013, 24 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/946,002, dated Oct. 2, 2013, 39 pages.
Non-Final Office Action, U.S. Appl. No. 13/730,608, dated Oct. 7, 2013, 10 pages.
Notice of Allowance, U.S. Appl. No. 12/636,939, dated Oct. 7, 2013, 28 pages.
Response to Final Office Action, U.S. Appl. No. 12/546,545, dated Dec. 9, 2013, 8 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
Response to Non-Final Office Action, U.S. Appl. No. 13/723,904, filed Nov. 6, 2013, 8 pages.
Response to Non-Final Office Action, U.S. Appl. No. 11/946,002, filed Dec. 6, 2013, 18 pages.
U.S. Appl. No. 14/084,255, filed Nov. 19, 2013, Park et al.
U.S. Appl. No. 14/086,849, filed Nov. 21, 2013, Park et al.
U.S. Appl. No. 14/086,878, filed Nov. 21, 2013, Park et al.
Non-Final Office Action, U.S. Appl. No. 11/946,002, dated Feb. 6, 2014, 46 pages.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/505,056, dated Mar. 6, 2014, 10 pages.
Notice of Allowance, U.S. Appl. No. 12/760,388, dated Jan. 22, 2014, 13 pages.
Notice of Allowance, U.S. Appl. No. 13/730,585, dated Mar. 18, 2014, 10 pages.
Response to Final Office Action, U.S. Appl. No. 11/641,569, dated Jan. 29, 2014, 10 pages.
Response to Final Office Action, U.S. Appl. No. 12/505,056, dated Feb. 26, 2014, 19 pages.
Response to Final Office Action, U.S. Appl. No. 13/723,904, dated Feb. 19, 2014, 7 pages.
Response to Final Office Action, U.S. Appl. No. 13/730,585, dated Feb. 26, 2014, 9 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Siemens MAGNETOM Sonata I.5T Technical Specifications, pp. 1-4, accessed online Jan. 28, 2014.

\* cited by examiner

HIP RESURFACING SURGICAL GUIDE TOOL

CROSS REFERENCE TO RELATED APPLICATIONS

This application claims benefit of priority under 35 U.S.C. 119(e) to: U.S. Patent Application No. 61/032,671, entitled Hip Resurfacing Surgical Guide Tool and filed Feb. 29, 2008; U.S. Patent Application No. 61/108,761, entitled Hip Resurfacing Surgical Guide Tool and filed Oct. 27, 2008; and U.S. Patent Application No. 61/111,238, entitled Total Hip Replacement Surgical Guide Tool and filed Nov. 4, 2008. The foregoing applications are hereby incorporated by reference into the present application in their entireties.

The present application also incorporates by reference in its entirety co-pending U.S. patent application Ser. No. 12/391,008, entitled Total Hip Replacement Surgical Guide Tool, and filed on the same date as the present application, namely, Feb. 23, 2009.

FIELD OF THE INVENTION

The present invention relates to medical apparatus and methods. More specifically, the present invention relates to hip resurfacing surgical guide tools and methods of using such tools.

BACKGROUND OF THE INVENTION

Arthroplasty is an orthopedic surgical procedure in which a dysfunctional or arthritic joint surface is replaced, remodeled or redesigned to alleviate pain, restore range of motion or to fix physical joint damage caused by a fracture. There are several surgical options available for a dysfunctional or arthritic hip joint. For example, Total Hip Replacement ("THR") surgery, also known as hip arthroplasty, is a surgical procedure wherein the proximal femur, with its femoral head and neck, is removed and a prosthetic device (or stem) having a prosthetic femoral head is implanted into the femur. The acetabulum, or hip socket, is also replaced or modified to accept a cup. The cup is configured to receive the prosthetic head. The prosthetic device (or stem) is typically made of titanium or a titanium alloy. The head may be made of a biocompatible plastic, ceramic or other suitable material. The cup may be made of a biocompatible plastic or other suitable material. The prosthetic device and the cup are typically anchored to the bone with bone cement.

Hip Resurfacing is another form of arthroplasty that was developed as an early intervention alternative to THR. In a Hip Resurfacing Surgery ("HRS"), the acetabulum is replaced, modified, or resurfaced to accept the cup, which is configured to receive the head. However, the proximal femur and, more specifically, the femoral head and neck, are not removed. Instead, the femoral head is resurfaced with, or otherwise modified to accept, a femoral head cap or other hip surface replacement.

Several factors, such as potential muscle damage or effect on the blood supply, are considered when choosing a surgical approach for a HRS or hip arthroplasty in general. Typically, a posterior approach or an anteriorlateral approach is utilized, but other approaches, such as a lateral approach or an anterior approach, may also be utilized. The posterior approach is traditionally known as a muscle sparing approach and is more common than the anteriorlateral approach, which is traditionally known as a muscle compromising approach. The posterior approach or anteriorlateral approach generally refers to the side to which the hip is dislocated as opposed to the location of the surgical incision. Regardless of which approach is used, the incision is on the side (lateral).

In some cases, the anteriorlateral approach may have a decreased rate of hip dislocation. This is important because in HRS, femoral neck impingement might occur more readily as a result of the absence of the head and neck offset that is normally associated with the original femoral components. Contact between the pelvic bone and the femoral neck may not only dislocate the femoral head but may also potentially become the origin of a stress-riser leading to a femoral neck fracture. The anteriorlateral approach may also preserve blood flow more consistently to the femoral head in comparison to the posterior approach because the approach produces less disruption to the blood flow in the femoral head-neck junction as reflected by a lower incidence of fracture of the femoral neck and avascular necrosis.

Typically, HRS utilizes a three part tool to properly place the femoral head cap through the center of the femoral head and along the central axis of the femoral neck. The tool is drilled into the femoral neck at a point that is estimated by observation of x-ray scans of the patient's femur. During surgery, this point is determined with a ruler and measured from the level of the greater trochanter of the femur. The three part tool is then drilled into the measured point. However, this three-part tool, the x-ray scan and hand measuring techniques are inaccurate and increase the error rate or potential for error in a hip resurfacing surgery.

Inaccurate drilling can result in a weakened femoral neck and/or damage to the artery extending through the femoral neck to supply the femoral head. Damage to this blood supply can lead to avascular necrosis.

There is a need in the art for a hip resurfacing surgical guide tool that increases accuracy, can be used with any surgical approach and reduces the potential for error associated with drilling through the femoral head and neck when preparing for hip surface replacement. There is also a need in the art for a method of manufacturing such a surgical guide tool.

BRIEF SUMMARY OF THE INVENTION

Disclosed herein is a tool for guiding a drill hole along a central axis of a femur head and neck for preparation of a femur head that is the subject of a hip resurfacing surgery. In one embodiment, the tool includes an index surface and a guide hole. The index surface is configured to matingly receive a predetermined surface of the femur. The index surface and guide hole are positionally correlated or referenced with each other such that when the index surface matingly receives the predetermined surface of the femur, the guide hole will be coaxial with a central axis extending through a centroid of a transverse cross section of the femur head and a centroid of a transverse cross section of the femur neck.

Disclosed herein is a tool for guiding a drill hole along a central axis of a femur head and neck for preparation of a femur head that is the subject of a hip resurfacing surgery. In one embodiment, the tool includes an index surface and a guide hole. The index surface is configured to matingly receive a predetermined surface of the femur. The index surface and guide hole are positionally correlated or referenced with each other such that when the index surface matingly receives the predetermined surface of the femur, the guide hole will be coaxial with a central axis extending through the femur head and the femur neck.

Disclosed herein is a surgical guide tool for use in hip resurfacing surgery on a proximal portion of a femur having a head, a neck extending distally from the head, a surface region distal the head, and a bone axis extending through a centroid of the head and a centroid of the neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a superior-posterior region of the neck. The at least a portion of a superior-posterior region of the neck may start between approximately 1 mm and approximately 5 mm after a cartilage covering the head terminates distally and may extend between approximately 15 mm and approximately 35 mm to a trochanteric fossa. In one embodiment, the at least a portion of a superior-posterior region of the neck may have an inferior border that begins approximately midway along an intertrochanteric crest and follows along the axis of the neck. In one embodiment, the at least a portion of a superior-posterior region of the neck may have a superior border between approximately 1 mm and approximately 3 mm below a junction between superior and anterior surfaces of the neck.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a superior-posterior region of the neck. The at least a portion of a superior-posterior region of the neck may include a narrow band that follows along an intertrochanteric crest and has a medial-lateral width of between approximately 0.5 mm and approximately 8 mm. In one embodiment, the at least a portion of a superior-posterior region of the neck may begin approximately midway along the intertrochanteric crest and may extend at least approximately 5 mm towards a most superior tip of a posterior surface of a greater trochanter.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a superior-anterior region of the neck. The at least a portion of a superior-anterior region of the neck may start between approximately 1 mm and approximately 5 mm after a cartilage covering the head terminates distally and may extend between approximately 15 mm and approximately 35 mm to terminate before a tubercle. In one embodiment, the at least a portion of a superior-anterior region of the neck may have a superior border approximately 1 mm to approximately 3 mm below a junction between superior and anterior surfaces of the neck. In one embodiment, the at least a portion of a superior-anterior region of the neck may have an inferior border that is between approximately 5 mm and approximately 10 mm from the superior boarder. In one embodiment, the at least a portion of a superior-anterior region of the neck may lie on an anterior greater trochanter, distal to a tubercle, and inferior to an origin of an obturator internus. In one embodiment, the at least a portion of a superior-anterior region may have a medial-lateral distance that measures between approximately 3 mm to approximately 14 mm. In one embodiment, the at least a portion of a superior-anterior region may have an inferior-superior distance that measures between approximately 3 mm to approximately 10 mm.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a superior-posterior region of the neck and at least a portion of a superior-anterior region of the neck, but may not include a junction between the superior-posterior and superior-anterior regions of the neck. In one embodiment, the at least a portion of the superior-posterior region of the neck may include an area that extends along the intertrochanteric chest, but may not include an area that spans portions of a trochanteric fossa. In one embodiment, the at least a portion of a superior-anterior region of the neck lies on an anterior greater trochanter, distal to a tubercle, and inferior to an origin of an obturator internus, but does not include portions of the tubercle.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a posterior region of the neck. The at least a portion of the posterior region of the neck may include an area that extends towards a trochanteric fossa between approximately 15 mm and approximately 35 mm from a first point being between approximately 1 mm and approximately 5 mm distal of a distal termination of a cartilage covering the head. In one embodiment, the at least a portion of a posterior region of the neck may have an inferior border that terminates up to approximately 5 mm superior to a border between posterior and inferior surfaces of the neck. In one embodiment, the at least a portion of a posterior region of the neck may have a superior border that terminates approximately 0 mm to approximately 5 mm posterior of a border between posterior and anterior surfaces of the neck. In one embodiment, the at least a portion of a posterior region of the neck may extend along an intertrochanteric crest from a lesser trochanter to a point near a tip of a greater trochanter. In one embodiment, the at least a portion of a posterior region of the neck may not include at least one of a portion of the trochanteric fossa and a portion of posterior region of the greater trochanter.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a posterior region of the neck. The at least a portion of the posterior region of the neck may include an area that includes a narrow band measuring between approximately 0.5 mm and approximately 12 mm and following along an intertrochanteric crest. In one embodiment, the narrow band may begin approximately 0 mm to approximately 12 mm superior to a lesser trochanter. In one embodiment, the narrow band may extend approximately 0 mm to approximately 18 mm inferior to a most superior tip of a posterior surface of a greater trochanter.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a posterior region of the neck. The at least a portion of the posterior region of the neck may include an area that extends towards a trochanteric fossa from a first point being between approximately 1 mm and approximately 5 mm distal of a distal termination of a cartilage covering the head, but may not include an area spanning portions of the trochanteric fossa. In one embodiment, the area spanning portions of the trochanteric fossa may have a width generally transverse to a femoral longitudinal axis of between approximately 0 mm and approximately 20 mm. In one embodiment, the at least a portion of the posterior region of the neck further includes an area that includes a band following along an intertrochanteric crest, but may not include portions of a posterior greater trochanter. In one embodiment, the portions of the posterior greater trochanter may have a distally extending dimension of between approximately 0 mm and approximately 12 mm.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of an anterior region of the neck. The at least a portion of an anterior region of the neck may extend up to approximately 8 mm laterally past an intertrochanteric line. In one embodiment, the surface region includes a medial surface of a greater trochanter.

Disclosed herein is a surgical guide tool for use in hip resurfacing surgery on a proximal portion of a femur having a head, a neck extending distally from the head, a surface region distal the head, and a bone axis extending through centers of the head and neck. In one embodiment, the tool may include a body including a guide hole and a mating region configured to matingly contact the surface region. The guide hole may include a hole axis. The guide hole and mating region may be positioned relative to each other so the hole axis is generally coaxially aligned with the bone axis when the mating region matingly contacts the surface region. The surface region may include at least a portion of a lateral posterior greater trochanter. In one embodiment, the surface region may further include at least a portion of a medial posterior greater trochanter. In one embodiment, the surface region may not include at least a portion of an intertrochanteric crest. In one embodiment, the surface region may further include at least a portion of a posterior region of the neck. In one embodiment, the surface region may not include at least a portion of a trochanteric fossa. In one embodiment, the surface region may further include at least a portion of a medial posterior greater trochanter and at least a portion of a posterior region of the neck, and wherein the surface region may not include at least a portion of an intertrochanteric crest and may not include at least a portion of a trochanteric fossa.

Disclosed herein is a method of manufacturing a surgical guide tool for use in hip resurfacing surgery on a proximal portion of a femur having a head, a neck extending distally from the head, and a surface region distal the head. In one embodiment, the method may include: a) generating medical imaging data associated with the proximal portion of the femur; b) employing the imaging data to generate a three-dimensional computer-generated femur model of the proximal portion of the femur; c) identifying a bone axis extending through a centroid of a head and a centroid of a neck of the femur model; d) providing a three-dimensional computer-generated tool model of at least portions of at least a surgical guide tool and a surgical guide tool blank; e) positionally referencing the bone axis with surface data associated with a surface of the femur model; f) merging the positionally referenced bone axis and surface data with the tool model so the bone axis and a hole axis associated with a guide hole of the tool model are coaxially aligned; g) computer generating manufacturing instructions from data determined from step f; and h) employing the manufacturing instructions at a manufacturing machine to generate the surgical guide tool from a surgical guide tool blank.

Disclosed herein is a method of manufacturing a surgical guide tool for use in hip resurfacing surgery on a proximal portion of a femur having a head, a neck extending distally from the head, and a surface region distal the head. In one embodiment, the method may include: a) generating medical imaging data associated with the proximal portion of the femur; b) employing the imaging data to generate a three-dimensional computer-generated femur model of the proximal portion of the femur; c) identifying a bone axis generally extending through a centroid of a head and a centroid of a neck of the femur model; d) providing a three-dimensional computer-generated tool model of at least portions of at least a surgical guide tool and a surgical guide tool blank; e) positionally referencing the bone axis with surface data associated with a surface of the femur model; f) merging the tool model and the positionally referenced bone axis and surface data so the bone axis and a hole axis associated with a guide hole of the tool model are generally coaxially aligned; g) computer generating manufacturing instructions from data determined from step f; and h) employing the manufacturing instructions at a manufacturing machine to generate the surgical guide tool from a surgical guide tool blank.

In one version of the embodiment of the method, the medical imaging data may be generated via at least one of MRI and CT. Also, the manufacturing machine may be at least one of a CNC machine and a SLA.

In one version of the embodiment of the method, the method may further include subjecting the medical imaging data to a segmentation process that determines bone contour lines and then adjusts the bone contour lines outward in locations of the bone contour lines corresponding to regions of the proximal portion of the femur that have surface topography that rapidly varies. The method may also include employing the adjusted bone contour lines to generate the three-dimensional computer-generated femur model of the proximal portion of the femur.

In one version of the embodiment of the method, the regions of the proximal portion of the femur that have surface topography that rapidly varies may include at least one of a portion of a tubercle and a portion of a superior intersection between anterior and posterior regions of the neck. In one version of the embodiment of the method, the regions of the proximal portion of the femur that have surface topography that rapidly varies may include at least one of a portion of a trochanteric fossa and a portion of a superior intersection between anterior and posterior regions of the neck. In one version of the embodiment of the method, the regions of the proximal portion of the femur that have surface topography that rapidly varies may include at least one of a portion of a trochanteric fossa and a portion of a posterior greater trochanter near an intertrochanteric crest. In one version of the embodiment of the method, the regions of the proximal portion of the femur that have surface topography that rapidly varies may include at least one of a portion of a trochanteric fossa and a portion of an intertrochanteric crest.

Disclosed herein is a method of manufacturing a surgical guide tool for use in hip resurfacing surgery on a proximal portion of a femur having a head, a neck extending distally from the head, and a surface region distal the head. In one embodiment, the method may include: a) generating medical imaging data associated with the proximal portion of the femur; b) employing the imaging data to generate a three-dimensional computer-generated femur model of the proximal portion of the femur; c) providing a three-dimensional computer-generated pin model including a longitudinal axis; d) superimposing the pin model and femur model; e) identifying a bone axis extending through a head and a neck of the femur model as being an axis that is generally coaxial with the longitudinal axis of the pin model; f) providing a three-dimensional computer-generated tool model of at least portions of at least a surgical guide tool and a surgical guide tool blank; g) positionally referencing the bone axis with surface data associated with a surface of the femur model; h) merging the tool model and the positionally referenced bone axis and surface data so the bone axis and a hole axis associated with a guide hole of the tool model are generally coaxially aligned; i) computer generating manufacturing instructions from data determined from step h; and j) employing the manufacturing instructions at a manufacturing machine to generate the surgical guide tool from a surgical guide tool blank.

In one version of the embodiment of the method, the medical imaging data may be generated via at least one of MRI and CT. Also, the manufacturing machine may be at least one of a CNC machine and a SLA.

In one version of the embodiment of the method, the pin model may further include a sphere centered on the longitudinal axis and, when the pin model and femur model are superimposed, at least a portion of a surface of the sphere coincides with at least a portion of a surface of the head of the femur model. The at least a portion of a surface of the head of the femur model may include at least one of an inferior portion and a posterior portion.

In one version of the embodiment of the method, the pin model may further include at least one of a first feature and a second feature, the first feature corresponding to an outer diameter of a resurfacing prosthetic implant, the second feature corresponding to an inner diameter of the resurfacing prosthetic implant. The pin model may further include a cylinder, wherein the first feature is an outer diameter of the sphere and the second feature is a diameter of the cylinder.

In one version of the embodiment of the method, the pin model may further include a cylinder generally coaxially centered on the longitudinal axis and further comprising at least one of translating the pin model and increasing the size of the pin model if a portion of the neck radially extends through a wall of the cylinder.

In one version of the embodiment of the method, the method may further include segmenting the imaging data via sections oriented at an angle with a central axis of the neck as viewed posteriorly of between approximately thirty degrees an approximately sixty degrees.

In one version of the embodiment of the method, the pin model and femur model may be initially superimposed such that the longitudinal axis of the pin model extends through both a centroid of a transverse cross-section of the neck and a centroid of a transverse cross-section of the head.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1A:
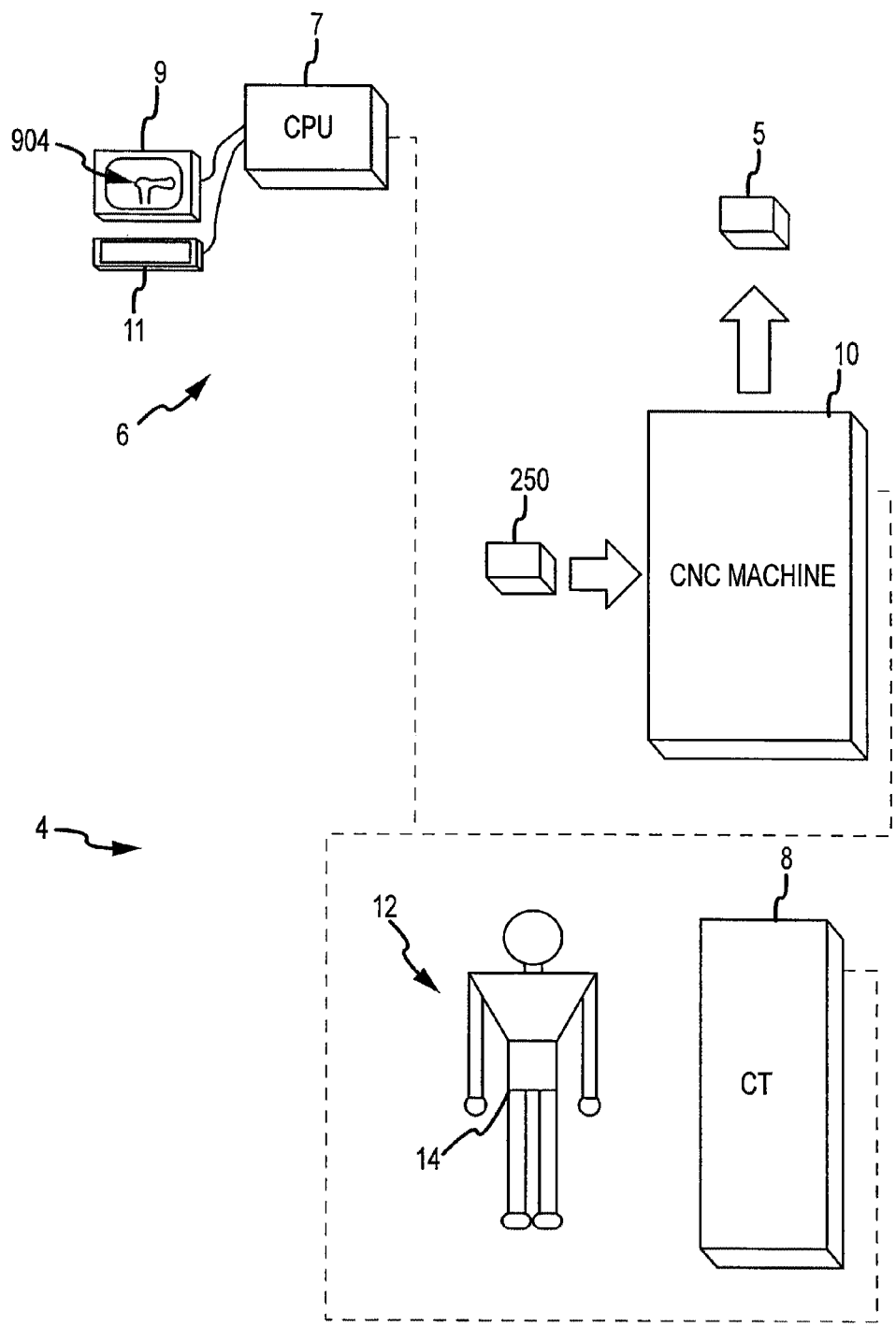
FIG. 1A is a diagrammatic depiction of a system for manufacturing a surgical guide tool as described herein.

The present disclosure describes a customized surgical guide tool or jig 5 for use in arthroplasty and systems and methods for making the same. In some embodiments, the tool 5 may be used in a hip resurfacing surgery. The tool 5 may have a single piece, unitary construction and a customized indexing or mating region 20 having indexing or mating surfaces for matingly contacting predetermined bone surfaces on the proximal femur. Which bone surfaces of the femur end up being used as the predetermined bone surfaces matingly received by the tool mating region 20 may depend on the type of surgery (e.g. hip resurfacing or hip replacement) or the surgical approach (e.g. a posterior approach or an anteriorlateral approach in a hip resurfacing procedure). In one embodiment, the tool 5 is customized such that when its mating region 20 matingly receives a region of the femur having the mating surfaces of the femur, the mating surfaces of the mating region 20 will matingly contact the mating surfaces of the femur. When the tool 5 thus properly fitted and fixed to the femur 40, an axis of a guide hole 65 of the tool 5 may be generally coaxially aligned with an axis extending through the head 30 and neck 35 of the femur 40. The guide hole 65 may then be used to guide a drill in a drilling operation used to form a hole extending along the axis of the femur for insertion of a guide wire used in the femur head resurfacing process.

As can be understood from FIG. 1A, which depicts a system 4 for the planning and manufacture of the customized tool 5, the system 4 may include a planning system or station 6, a medical imaging system 8 (e.g., a MRI system, a CT system, etc.), and an automated manufacturing system 10 (e.g., a CNC machine, a SLA, etc.), all of which may be in communication with one or more of each other via hardwire systems, wireless systems, internet, portable memory storage devices, a combination of these, etc. The planning system 6 may include a CPU 7, a monitor 9, and a user interface 11 such as a keyboard and/or mouse.

As can be understood from FIG. 1A, to preoperatively plan and manufacture the customized tool 5, medical imaging (e.g., MRI, CT, etc.) is taken of the hip region 14 of the patient 12 via the medical imaging machine 8. The resulting medical image slices 500 are sent to the CPU 7 of the planning system 6. The medical imaging slices 500 are segmented to identify the femur contour line 502 in each image slice 500. In one embodiment, the bone surface contour lines 502 of the bone 40 depicted in the image slices 500 may be auto segmented via a image segmentation process as disclosed in U.S. Patent Application No. 61/126,102, which was filed Apr. 30, 2008, is entitled System and Method for Image Segmentation in Generating Computer Models of a Joint to Undergo Arthroplasty, and is hereby incorporated by reference into the present application in its entirety. In one embodiment, the image segmentation process may be controlled via the user interface 11 and viewed via the monitor 9 to a greater or lesser extent, depending on the level of automation in the image segmentation process.

The regions of the femur contour lines 502 having rapid variation and/or associated with features too small to be replicated via automated manufacturing processes (e.g., CNC milling, a stereolithography apparatus ("SLA"), etc.) used to manufacture the tool 5 may be subjected to an overestimation process. Specifically, the contour lines may be moved outwardly away from the interior of the femur. In one embodiment, the method disclosed herein may employ an overestimation process as disclosed in U.S. Provisional Patent Application No. 61/083,053, which is entitled System and Method for Manufacturing Arthroplasty Jigs Having Improved Mating Accuracy, was filed by Park Jul. 23, 2008, and is hereby incorporated by reference in its entirety into this Detailed Description. In one embodiment, the overestimation process may be controlled via the user interface 11 and viewed via the monitor 9 to a greater or lesser extent, depending on the level of automation in the overestimation process.

Subsequent to the overestimation process, the contour lines are compiled into a three-dimensional ("3D") computer generated model 904 of the femur, wherein the surfaces of the 3D femur model are substantially identical to those of the scanned femur, except in those regions wherein the corresponding image contour lines were subjected to the overestimation process. Such surface regions subjected to the overestimation process may project outwardly from the interior of the femur model further than they would otherwise were it not for the overestimation process. Also, such surface regions subjected to the overestimation process may also be substantially smoother than they would otherwise be absent the impact of the overestimation process. The resulting 3D bone model 904 may be viewed on the monitor 9.

Computer programs for creating the 3D computer generated bone model 904 from the 2D images 500 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org. Such programs may be loaded on the CPU 7.

The 3D computer generated model 904 of the femur is analyzed on the planning system 6 via one of two methods to identify a desirable axis 100 extending through the femur neck 35 and head 30. In one embodiment, the centroids 135 of the femur neck and head are identified and the axis 100 is the one that extends through both centroids. In another embodiment, the axis is identified using a planning pin method. Each method is discussed separately in detail below.

In one embodiment and still using the planning system 6, once the axis 100 is identified, mating surfaces of the 3D femur model may be identified and positionally referenced relative to the axis 100. The axis 100 and mating surfaces may then be imported into a 3D computer model of a tool blank such that the axis 100 is coaxially aligned with an axis extending through a guide hole 65 of the tool blank. The mating surfaces may then be used to define the indexing surfaces of the mating region 20 of the resulting 3D computer model of the tool 5. The resulting 3D computer model of the tool 5 may then be used to create manufacturing instructions, which may be sent from the planning system 6 to the automated manufacturing system 10. The manufacturing system 10 may employ the manufacturing instructions to create the actual tool 5 from an actual tool blank 250.

In another embodiment and still using the planning system 6, once the axis 100 of the 3D femur model is identified, a 3D model of the tool blank may be imported into the 3D femur model such that an axis of a guide hole 65 of the tool blank is generally coaxially aligned with the axis 100 of the 3D femur model. The 3D tool blank model may be rotated about the axes, which are coaxially aligned, until the mating region 20 of the 3D tool blank is positioned on the 3D femur model as would be the case with the actual tool 5 on the actual patient femur 40. The mating surfaces of the 3D femur model covered by the mating region 20 of the 3D tool blank model may be used to define the index surfaces the mating region of the resulting 3D tool model. The resulting 3D computer model of the tool 5 or manufacturing instructions (e.g., tool path instructions, etc.) may then be sent from the planning system 6 to the manufacturing machine 10 to manufacture the actual tool 5 from an actual tool blank 250.

While the preceding embodiments are discussed in the context of 3D computer models or surfaces being imported into another 3D computer model, those of skill in the art will readily understand that in a computer environment, what may be caused to occur may be the correlation of one set of data with another set of data to generate manufacturing instructions that may be employed by a rapid manufacturing system such as, for example, a CNC machine or a SLA.

Once the tool 5 is manufactured via the manufacturing machine 10, the tool 5 may be labeled according to patient name, physician, joint name, etc., cleaned and sterilized, packaged and sent to the physician. During surgery, the patient's proximal femur may be exposed and dislocated from the hip joint. The tool 5 may be applied to the exposed proximal femur such that the mating region 20 of the tool 5 matingly receives the corresponding region of the proximal femur. The tool 5 may be held in place or secured in such a mating arrangement on the femur via screws, drill bits or other types of anchoring devices. Because of the preoperative planning that resulted in the customized configuration of the tool 5, the axis of the guide hole 65 of the tool 5 may be generally coaxial with a predetermined axis 100 of the femoral head and neck. A drill guide may be inserted into the tool guide hole, and a drill may be inserted through the drill guide to drill a hole in the proximal femur extending along the axis 100 of the femoral head and neck. Once the hole is drilled, a guide wire may be inserted into the drilled hole and the tool 5 may be removed and thrown away. The guide wire may then be used to guide the resurfacing device in the preparation of the femoral head for receiving the femoral head resurfacing implant 600.

The following sections A and B of this Detailed Discussion respectively discuss in detail a tool 5 configured for a posterior approach and a tool configured for a posterior or anterolateral approach. Each of these sections of the Detailed Discussion discuss in detail methods of preoperatively planning, manufacturing and using the respective tool 5. While certain bone mating surfaces and methods of planning and manufacture of the tool are discussed with respect to each type of tool 5 and in certain combinations, it should be understood that the bone mating surfaces and methods of manufacture and use of the tool are interchangeable in different combinations between the various tool embodiments disclosed herein, and these combinations and variations should be considered as being part of the inventions disclosed herein. Accordingly, any limitations associated with the inventions disclosed herein should be according to the scope of claims accompanying this Detailed Disclosure.

A. Surgical Guide Tool for a Posterior Approach

Figure 2A:
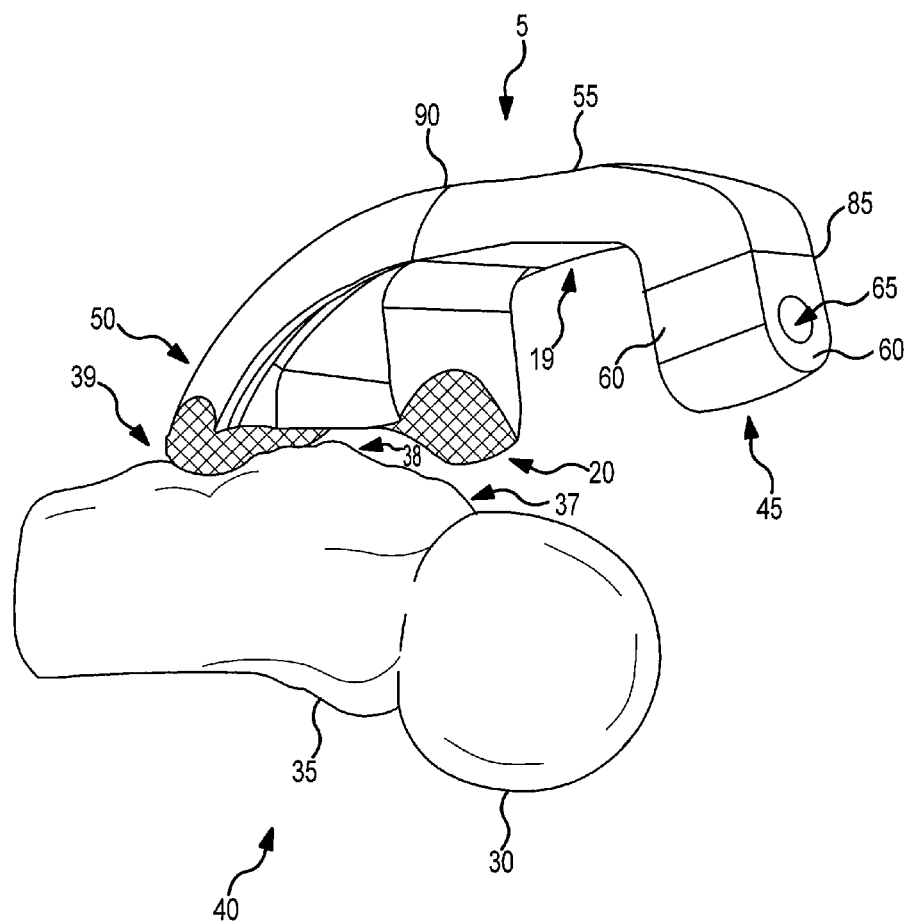
FIG. 2A is an isometric view of one embodiment of a surgical guide tool that may be used in a hip resurfacing procedure, wherein a proximal femur with its femoral head, neck and greater trochanter is also shown.
Figure 2B:
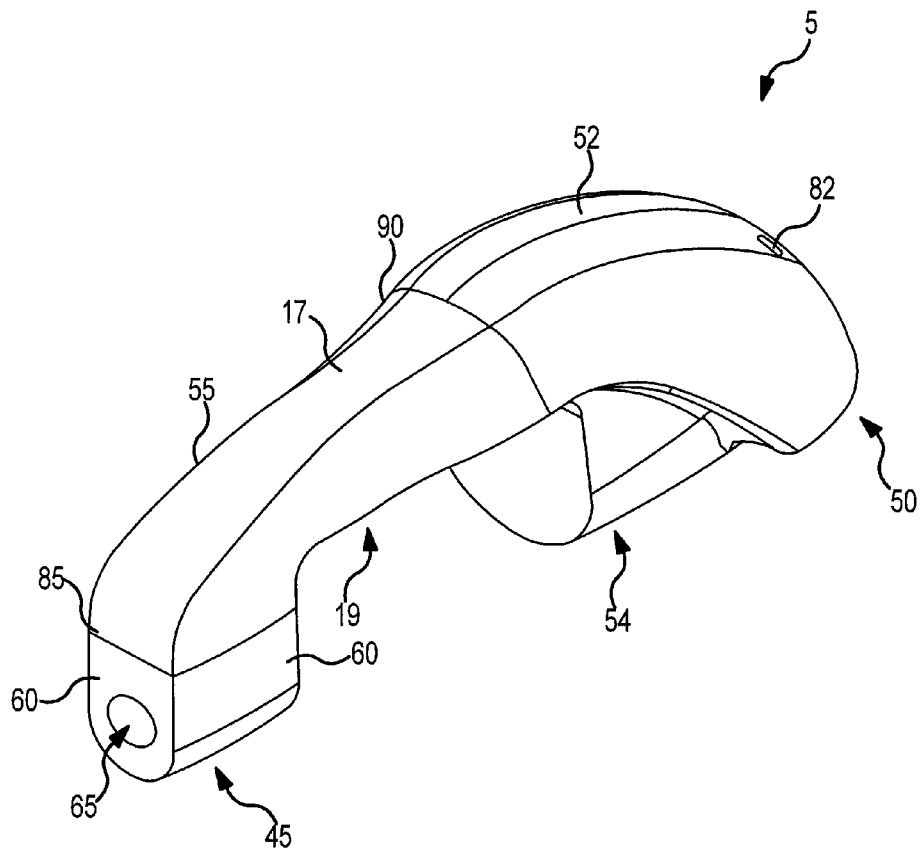
FIG. 2B is a side top isometric view of the surgical guide tool of FIG. 2A, wherein the tool is in a non-customized state or is the form of a blank from which the customized tool is generated via a CNC milling machine.
Figure 2C:
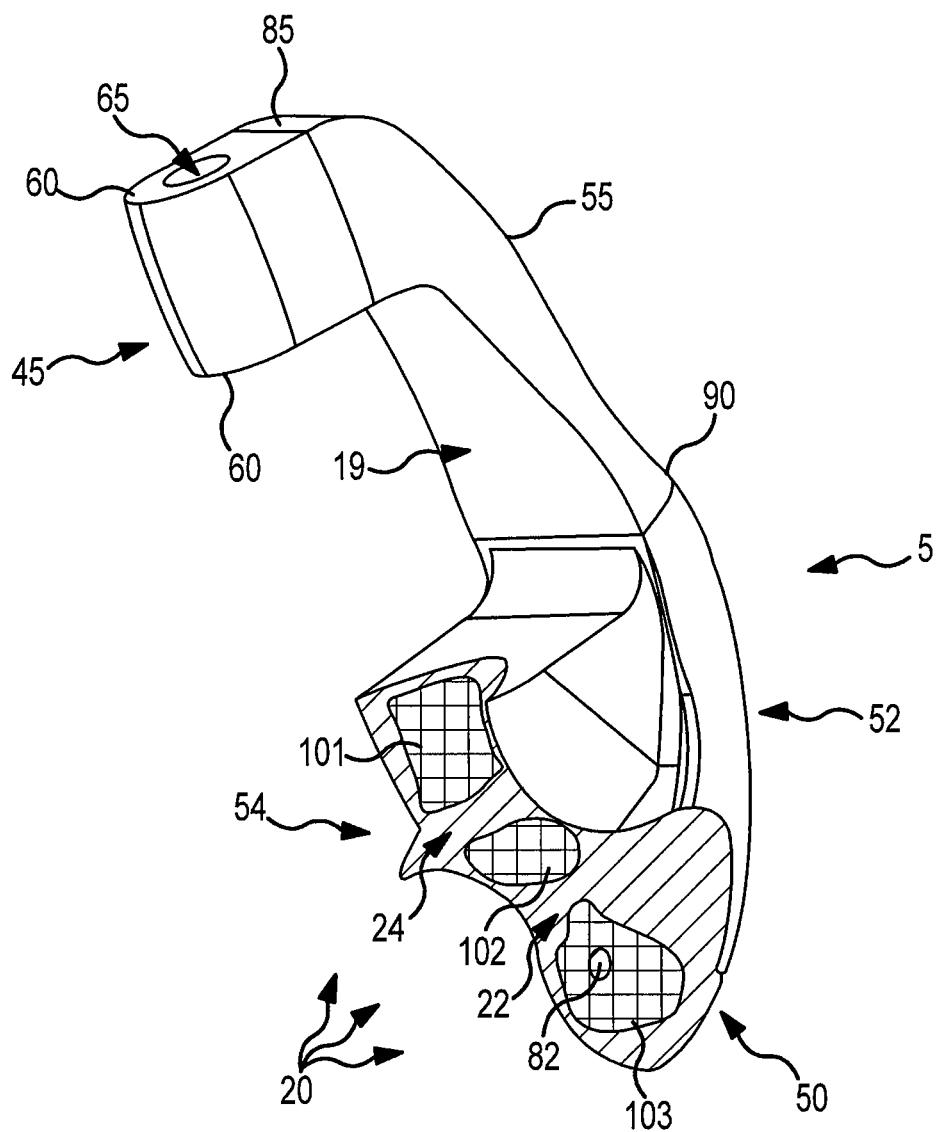
FIG. 2C is a side bottom isometric view of the surgical guide tool of FIG. 2A, wherein the tool is in a customized state.
Figure 2D:
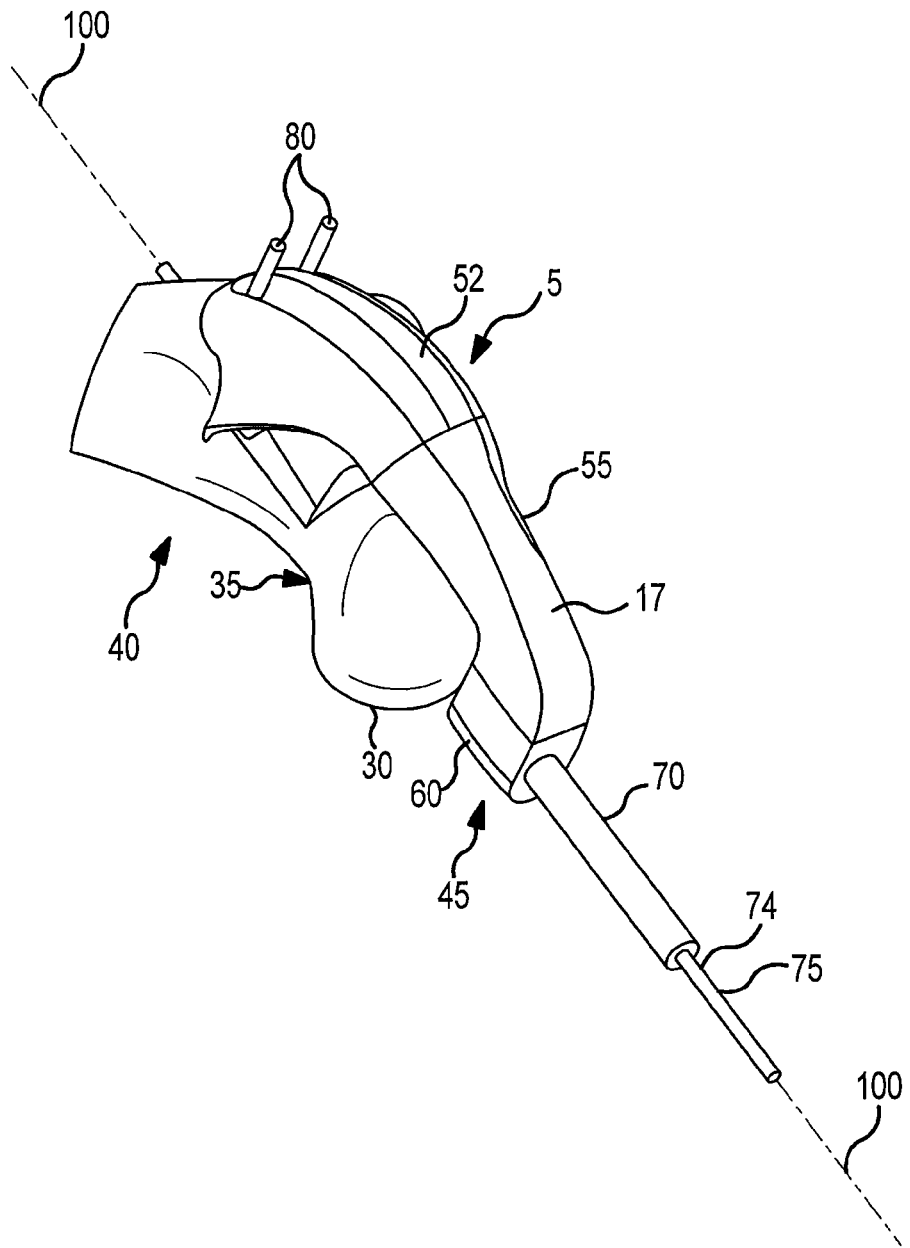
FIG. 2D is an isometric view of the surgical guide tool and the femur of FIG. 2A, wherein the tool is shown mounted on the femur.
Figure 2E:
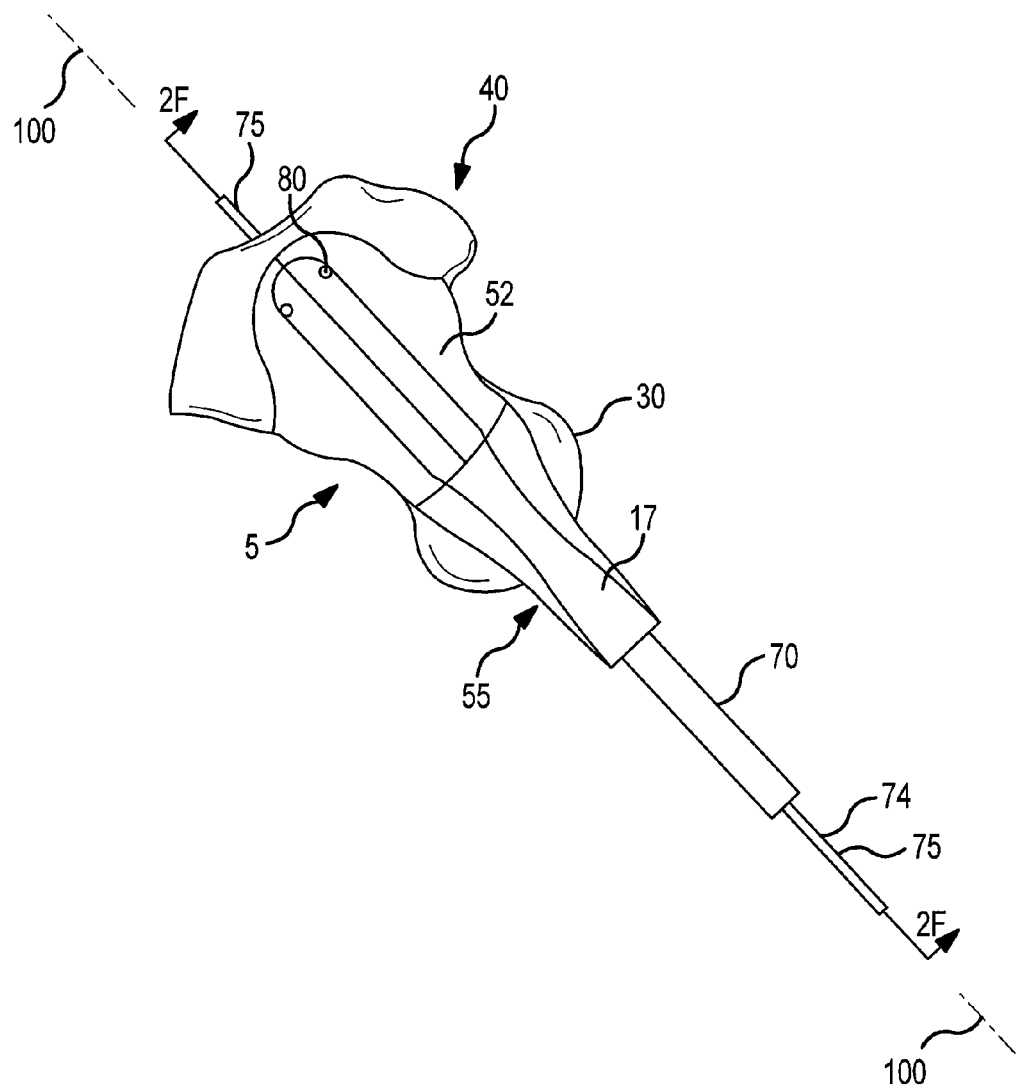
FIG. 2E is a top plan view of the tool and femur of FIG. 2D.
Figure 2F:
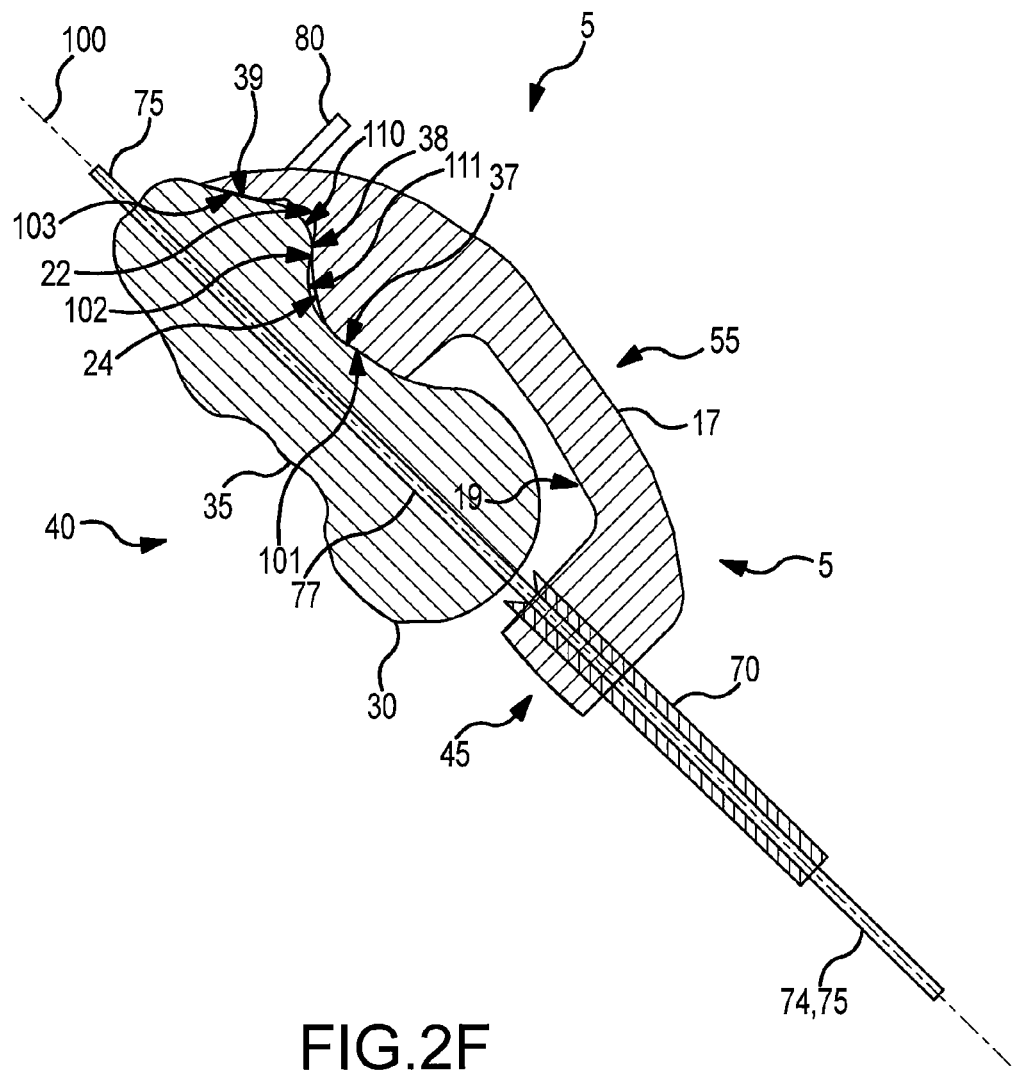
FIG. 2F is a longitudinal cross-section of the surgical guide tool and femur as taken along section line 2F-2F of FIG. 2E.

For a general discussion of features of an embodiment of a surgical guide tool 5 for use in a posterior approach to a hip resurfacing surgery, reference is first made to FIGS. 2A-2F. FIG. 2A is an isometric view of the surgical guide tool 5 and a proximal femur 40 with its femoral head 30, neck 35 and greater trochanter 115. FIG. 2B is side top isometric view of the surgical guide tool 5, wherein the tool 5 is in a non-customized state or is in the form of a blank from which the customized tool 5 is generated via a CNC milling machine. FIG. 2C is a side bottom isometric view of the surgical guide tool 5, wherein the tool 5 is in a customized state. FIGS. 2D and 2E are, respectively, isometric and top plan views of the surgical guide tool 5 and the femur 40 of FIG. 2A, wherein the tool 5 is shown mounted on the femur 40. FIG. 2F is a longitudinal cross-section of the surgical guide tool 5 and femur 40 as taken along section line 2E-2E of FIG. 2E.

As illustrated in FIGS. 2A-2E, in one embodiment, the surgical guide tool 5 includes a head end 45, a mating end 50, and a connecting arm 55. In one embodiment, the ends 45, 50 and the connecting arm 55 are formed or otherwise joined together such that the tool 5 is a single-piece tool having a single-piece construction that is generally unitary and continuous in nature. In other embodiments, the tool 5 will have a multi-piece construction formed of two or more individual pieces joined together in preparation for, or in the course of, being mounted on a femur during a HRS.

The mating end 50 may be machined or otherwise manufactured to have a mating region 20 that matingly receives a corresponding surface area of the proximal femur 40. More specifically, the mating region or surface 20 may have mating or index surfaces 101, 102, 103 and overestimated or non-contacting surfaces 22, 24, wherein, when the mating region 20 matingly receives the corresponding surface area of the proximal femur 40, the mating or index surfaces 101, 102, 103 matingly contact corresponding surfaces of the proximal femur 40 and the overestimated or non-contacting surfaces 22, 24 are spaced apart from their corresponding surfaces of the proximal femur 40 so as to not contact those proximal femur surfaces.

As will be discussed with respect to FIG. 4 later in this Detailed Description, which details those femur surfaces corresponding to the mating contact surfaces 101, 102, 103 and the overestimated non-contacting surfaces 22, 24 of the mating region 20 of the surgical guide tool 5 for a posterior approach, the mating end 50, and more specifically, the mating region 20 may be adapted to receive therein and mate with surfaces of the proximal femur 40, such as, for example, the posterior region 37 of the neck 35, a medial posterior surface 38 of the greater trochanter 115 between the intertrochanteric crest 116 and trochanteric fossa 118 and a region 39 that is part of the lateral posterior greater trochanter 115 and the lateral posterior body of the femur bordering the intertrochanteric crest 116. The surfaces 37, 38, 39 to be mated or indexed by the tool index surfaces 101, 102, 103 and may be separated by areas of non-mating regions 110, 111 that are spanned in a spaced-apart or non-contacting arrangement by non-contacting surfaces 22, 24 of tool 5. The non-contacting surfaces 22, 24 of the mating region 20 of the tool 5 are surfaces that do not contact the non-mating regions 110, 111 and may be generated via an over-estimating process during image segmentation as described later in this Detailed Description. The non-mating regions 110, 111 of the proximal femur 40 may be portions 111 of the trochanteric fossa 118 (i.e., the depression between the greater trochanter and the femur neck) and portions 110 of the intertrochanteric crest 116.

The head end 45 includes a guide hole 65 and is configured to be positioned adjacent to the femoral head 30 without contacting the femoral head 30 and, more specifically, to position the guide hole 65 near the center of the spherical surface of the femur head 30. In some embodiments, the head end 45 may contact the surface of the femoral head 30 while still positioning the guide hole 65 near the center of the spherical surface of the femur head 30. The connecting arm 55 extends from the mating end 50 to the head end 45, thereby connecting the ends 50, 45. The tool 5 may be made of polyoxymethylene (acetal resin), a low density polyethylene, or other biocompatible plastics.

As shown in FIGS. 2A-2F, the connecting arm 55 includes a top face 17 and a femur face 19, a first end 85 and a second end 90. In one embodiment, as best understood from FIG. 2F, the femur face 19 of the arm 55 is generally a rectangular-shaped arch and the top face 17 of the arm 55 is generally arcuate. The arm 55 is configured to generally extend across the femoral head 30 without contacting the head 30. That is, the arm 55 extends between, and thereby connects, the head and mating ends 45, 50 but does not contact the external surface of the head 30. In some embodiments, the arm 55 may contact the external surface of the head 30 or other portions of the proximal femur 40. In some embodiments, the femur face 19 of the arm 55 may not be a rectangular-shaped arch, but may be an arcuate shape to enable the tool 5 to fit or more closely follow along the femoral region as described herein.

As can be understood from FIGS. 2A-2C, the head end 45 of the tool 5 includes a semi-circular or U-shaped end 60 and at least one guide hole 65. The U-shaped end 60 generally extends from the first end 85 of the connecting arm 55 to approximately the center of the spherical surface of the femoral head 30 without contacting the head 30. In some embodiments, the U-shaped end 60 may contact an external surface of the femoral head 30.

The guide hole 65 of the head end 45 extends axially through the head end 45 and may have a cylindrical construction. As can be understood from FIGS. 2D-2F, the guide hole 65 of the head end 45 defines a passageway to receive a guide rod 70 through which a drill 74 is extended during surgery to drill a hole 77 through the femur head 30 and femur neck 35 along the central axis 100 thereof. Once the hole 77 is complete, the drill 74 can be removed and replaced with a guide wire 75 that may be used as a reference post for the devices employed in the resurfacing of the spherical surface of the femur head 30.

In one embodiment, the mating end 50 of the tool 5 may be adapted to receive therein and mate with the proximal femur 40 and, more specifically, limited and predetermined regions 37, 38, 39 of the proximal femur 40. As can be understood from FIGS. 2B and 2C, the mating end 50 of the tool 5 includes a top side 52 and a femur side 54. A portion of the femur side 54 of the mating end 50 includes a customizable or mating region 20, which, as depicted in FIG. 2F, may include one or more indexing or mating surfaces 101, 102, 103 configured to matingly contact portions of the proximal femur 40 (e.g., regions 37, 38, 39 of the proximal femur 40 as discussed with respect to FIG. 4) when the mating region 20 matingly receives the corresponding portion of the femur 40.

As shown in FIG. 2B, the mating end 50, when in a non-customized state such as when the tool 5 exists as a blank from which the tool 5 is machined, includes a generally arcuate top side 52, a generally U-shaped femur side 54, and fastening member-receiving openings 82. As indicated in FIGS. 2B and 2C, the openings 82 extend through the mating end 50 from the top side 52 to the femur side 54 and may have a cylindrical construction. The openings 82 are configured to receive fastening members 80 used to secure the tool 5 to the proximal femur 40 when the indexing surfaces 101, 102, 103 matingly contact the corresponding bone surfaces 37, 38, 39. In one embodiment, there may be two openings 82. In alternative embodiments, there may be more than two openings 82 or less than two openings 82.

As described in more detail below, the mating region 20 of the tool 5 may be customized based on a patient's individual bone shape. The tool 5 may be machined, molded or otherwise formed from the non-customized state as illustrated in FIG. 2B to a customized state as indicated in FIG. 2C, based on a patient's individual bone scan, for example an MRI scan or CT-scan. That is, through the information received from the MRI scan or CT-scan, the tool 5 may be customized at the mating region 20 such that the tool 5 will have mating or indexing surfaces 101, 102, 103 generally conforming to the predetermined specific surface geometry of the patient's own proximal femur 40. In some embodiments, the predetermined specific geometry will be that of regions 37, 38, 39 discussed with respect to FIG. 4. Such customization increases the likelihood the drill hole 77 (see FIG. 2F) will extend along the central axis 100 of the femur head 30 and neck 35, thereby increasing the accuracy of the femur head resurfacing procedures indexed off of the hole 77 and the placement of the prosthetic surface implanted on the resurfaced femur head as part of a HRS. Depending on the embodiment, the tool 5 may be manufactured in its customized configuration via a CNC machine or a SLA.

As illustrated in FIG. 2C, in a customized state, the mating end 50 includes a top side 52, a femur side 54, and fastening member-receiving openings 82. As described above with respect to FIGS. 4 and 2F, the bone mating region 20, in a customized state, includes mating surfaces 101, 102, 103 configured to matingly contact corresponding femoral bone surfaces 37, 38, 39 and overestimated or non-contacting surfaces 22, 24 configured to extend over, but not contact, corresponding surfaces 110, 111.

As can be understood from FIGS. 2D-2F, the fastening members 80 may be received in the fastening member-receiving openings 82 in the mating end 50, thereby securing or coupling the mating end 50 of the tool 5 with the proximal femur 40 in the vicinity of the greater trochanter 115 and maintaining the mating surfaces 101, 102, 103 of the mating region 20 of the tool 5 in an indexed or mating arrangement corresponding with mating surfaces 37, 38, 39 of the femur 40. The fastening members 80 may stabilize the tool 5 during surgery such that the guide rod 70 extending through the guide hole 65 may provide a stable and accurate mechanism for guiding a drill bit 74 extended through the guide rod 70. The fastening members 80 may be screws, pins, or drill bits.

As can be understood from FIGS. 2D-2F, and with reference to FIG. 2A, by securely mounting the tool 5 on the femur 40 such that the tool index surfaces 101, 102, 103 matingly receive corresponding mating surfaces 37, 38, 39 of the femur 40, the guide hole 65 is properly aligned to guide a drill bit in forming a hole 77 that is aligned with a central axis 100 of the femur head 30 and neck 35. Proper alignment of the hole 77 with the axis 100 prevents or at least minimizes the chances of several undesirable complications. For example, failure of the hole 77 to properly align with the axis 100 can cause the femoral neck to become prone to fracture. Additionally, failure of the hole 77 to properly align with the axis 100 can cause the drill bit 74 to hit the femoral artery when drilling the hole 77. The femoral artery is the only blood supply to this region of the femur and if severed, the hip will develop avascular necrosis.

As shown in FIGS. 2D-2F, during surgery, the guide rod 70 is received in the guide rod-receiving opening or guide hole 65 in the head end 45 of the tool 5. The guide rod 70 is configured to receive the drill hole 74 and guide wire 75. The guide rod 70 may be made of surgical stainless steel or titanium. The guide wire 75 may be made of surgical stainless steel or titanium. During surgery, the guide rod 70 is inserted in the guide rod-receiving opening 65 to aid the surgeon in aligning the drill 74 for accurately forming the reference hole 77 in the femur 40. A guide wire 75 may be placed in the hole 77 and used to guide the devices used in resurfacing the spherical surface of the femur head 30 in preparation for receiving the spherical prosthetic surface to be mounted on the resurfaced femur head. Thus, the tool 5 aids the surgeon in accurately drilling the hole 77 to extend along the central axis 100 of the femur head and neck, thereby decreasing the risks commonly associated with hip surface replacement surgery, such as fractures to the femoral neck and damage to the femoral artery.

1. Alignment Through a Central Axis

In some embodiments, the proper orientation of the guide hole 65, wherein a drill extended through the guide hole will be caused to extend along a central axis extending through the femoral head and neck, may be determined during the preoperative planning process by analyzing transverse cross-sections of the neck and head of a 3D computer model of the femur and approximating the centroid of each such transverse cross-section. For a discussion of one embodiment of a centroid determination method, reference is now made to FIG. 3, which is an isometric view of the proximal femur 40 of FIG. 2A, wherein the central axis 100 through the proximal femur 40 is shown.

Figure 3:
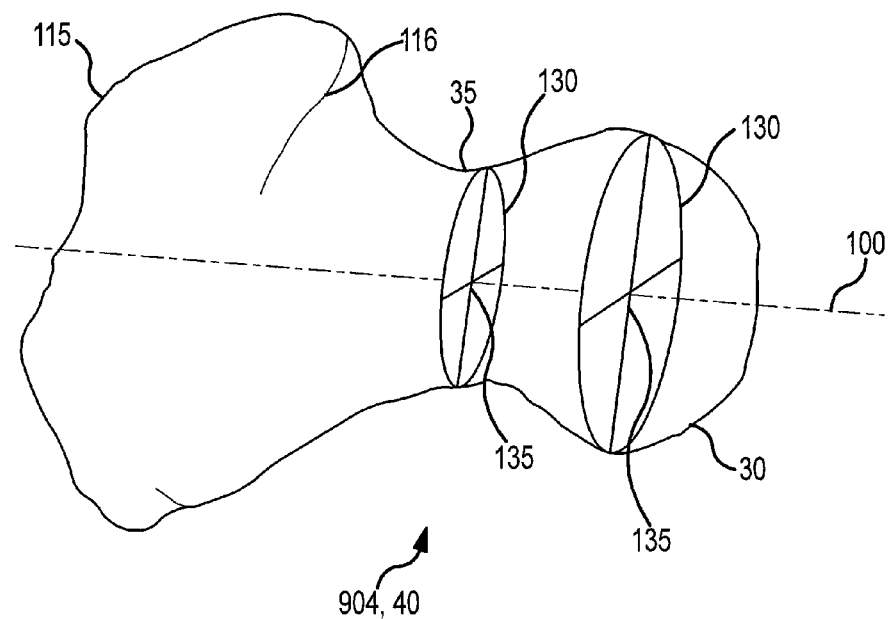
FIG. 3 is an isometric view of the femoral region of FIG. 2A, wherein the central axis through the region is shown.

With the aid of a modeling program, such as Solidworks or others described above in the section entitled "Overview of System and Method for Manufacturing Customized Surgical Guide Tools or Jigs", and as shown in FIG. 3, the approximate center axis 100 of the femoral neck 35 and head 30 may be found by identifying the centroids 135 of the cross-sections 130 of the head 30 and neck 35 of a 3D computer model of the femur 40. At each of these cross-sections 130, the centroid 135 of the section is approximated. An axis line 100 is drawn through the two approximated centroid points 135 determined by the centroid analysis of the two cross sections 130 of the neck 35 and head 30 of the 3D computer generated model of the proximal femur 40. The placement of a 3D computer generated model of the guide wire 75 may then be determined by positioning the 3D modeled guide wire to be coaxially aligned with the center axis 100 of the neck 35 and head 30 of the 3D model of the femur 40.

Computer modeling during the preoperative planning process may also determine placement of the tool relative to the femur. That is, the placement of the 3D model of the guide wire 75 may determine where the 3D computer model of the tool may be positioned on the 3D computer generated model of the femur. During the preoperative planning process, the guide rod receiving opening of the 3D model of the tool may be placed concentrically around the 3D model of the guide wire, and the 3D model of the tool is then free to rotate around the axis 100, wherein the axis 100 and the axis of the guide wire are maintained coaxial during the rotation. This coaxially consistent rotation is used to position the 3D model of the tool in proper position relative to the 3D model of the femur for the importation of the mating surfaces into the mating region 20 of the 3D model of the tool.

2. Mating Regions

Generation of the mating regions 101, 102, 103 may also be determined with the aid of a modeling computer program, such as Solidworks. For a discussion of the mating surfaces of one embodiment of a hip resurfacing surgical guide tool 5, reference is now made to FIG. 4, which is an isometric view of the proximal femur 40 of FIG. 2A showing the regions of the femur that are mated with the index surfaces of the tool and the regions that correspond to over-estimated or non-contacting surfaces of the tool.

Figure 4:
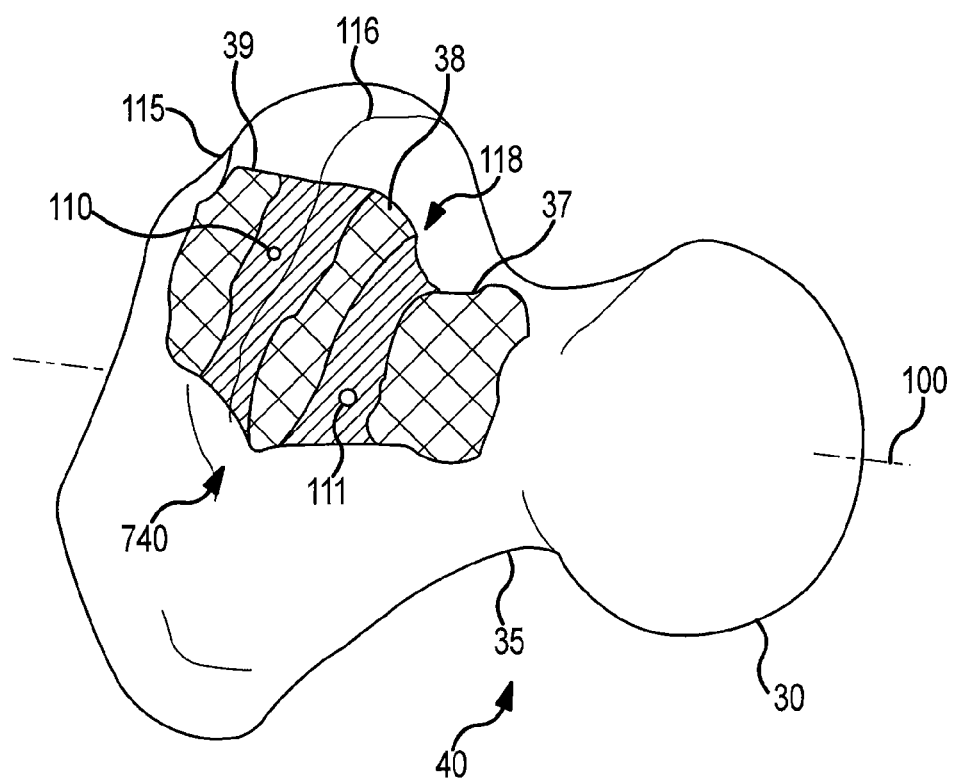
FIG. 4 is an isometric view of the proximal femur of FIG. 2A showing the surfaces of the femur that are mated with the index surfaces of the tool and the surfaces that correspond to over-estimated or non-contacting surfaces of the tool.

As can be understood from FIG. 4, the mating end 50 may be adapted to receive therein and mate with surfaces of the proximal femur 40, such as, for example, the posterior region 37 of the neck 35, a medial posterior surface 38 of the greater trochanter 115 between the intertrochanteric crest 116 and trochanteric fossa 118, and a region 39 that is part of the lateral posterior greater trochanter 115 and the lateral posterior body of the femur bordering the lateral side of the intertrochanteric crest 116. The mating surface 37 may cover portions of the posterior region of the neck 35, starting medially between approximately 1 mm and approximately 5 mm after the cartilage covering the head 30 of the femur 40 terminates laterally and laterally extends between approximately 15 mm and approximately 35 mm to or towards the trochanteric fossa 118. Region 38 may be a band, extending from the lesser trochanter 740 to the anterior surface of the femur, and ranging in width from between approximately 0 mm to approximately 14 mm. The medial border of region 38 is the trochanteric fossa 118 and the lateral border is approximately the intertrochanteric crest 116. Region 39 begins medially at approximately the crest 116, and may extend from 0 mm to approximately the edge of the posterior surface of the femur 40. The inferior/superior length of region 39 may be 0 mm, or may extend from the lesser trochanter 740 to the superior border of the posterior surface of the femur 40.

The surfaces 37, 38, 39, which are to be mated or indexed by the tool index surfaces 101, 102, 103 of the mating region 20 of the tool 5, may be separated by areas of non-mating surfaces 110, 111 that are spanned by overestimated or non-contacting surfaces 22, 24 of the mating region 20 of the tool 5. The non-contacting surfaces 22, 24 (see FIG. 2F) of the mating region 20 of the tool 5 do not contact the corresponding non-mating surfaces 110, 111 of the femur 40 and may be generated via an over-estimating process during image segmentation. The non-mating surfaces 110, 111 of the proximal femur 40 may be portions 111 of the trochanteric fossa 118 (i.e., the depression between the greater trochanter and the femur neck) and portions 110 of the intertrochanteric crest 116. The non-mating surface or portion 111 may span portions of the trochanteric fossa 118, and may have a medial boundary that is the mating surface 37 and a lateral boundary that is the mating surface 38, and a medial-lateral width that may vary between approximately 0 mm and approximately 20 mm. Non-mating surface or portion 110 may be a band including the intertrochanteric crest 116, and may extend from the lesser trochanter 740 to the most superior point of the greater trochanter 115. The medial-lateral width of the surface 110 may be from approximately 0 mm to approximately 12 mm. Generally, any surface of mating region 20 that is outside of tool mating surfaces 101, 102, 103 (which correspond to femur mating surfaces 37, 38, 39, respectively) may be tool non-contacting surfaces 22, 24, which correspond, respectively to femur non-contacting surfaces 110, 111.

As can be understood from FIG. 4, the mating end 50 of the tool may be placed on the femur 40 such that the mating region 20 of the tool 5 covers and matingly receives the femur area encompassing the mating surfaces 37, 38, 39 and non-mating surfaces 110, 111 of the proximal femur 40. As discussed above, non-mating regions 110, 111, including portions of the trochanteric fossa 118 (the depression between the greater trochanter and the neck of femur) and the intertrochanteric crest 116, are not easily estimated due to drastic changes in surface geometry, and corresponding non-mating surfaces 22, 24 of the mating region 20 of the tool 5 do not contact these surfaces 110, 111 when the region of the femur that includes the femur mating surfaces 37, 38, 39 and non-mating surfaces 110, 111 are matingly received by the mating region 20 of the tool 5. While this discussion of mating region 20 is made with respect to FIG. 4, the tool mating region 20 configured to have mating and non-mating surfaces that correspond to mating and non-mating surfaces of the femur, such as those discussed with respect to FIGS. 14A-16B, may also be used.

In one embodiment, during the preoperative planning process, once the 3D computer generated model of the blank of the tool 5 is rotated into a desired position about the coaxially aligned 3D computer generated model of the guide wire 75 and the axis 100 of the 3D computer generated model of the femur 40 such that the mating end 50 of the 3D model of the blank of the tool 5 is positioned over the desired mating region of the model of the femur 40, the mating surfaces 37, 38, 39 of the model of the femur 40 may be used to generate or define corresponding index surfaces 101, 102, 103 of the mating region 20 into the 3D model of the blank of the tool 5. The non-mating surfaces 110, 111 of the 3D model of the femur 40 may overestimated and then used to generate or define corresponding non-mating surfaces 22, 24 of the mating region 20 into the 3D model of the blank of the tool 5. Thus, the resulting 3D computer generated model of the tool 5 represents a tool 5 having a customized mating end 50 configured to matingly receive a desired and specific mating region of the patient's femur. The data associated with the 3D computer model of the customized tool 5 can be sent to a CNC machine or SLA to create an actual customized tool from an actual blank of the tool. The mating region 20 of the actual customized tool 5 will conform to the segmented CT scan or MRI scan of the patient's femur and be capable of matingly receiving the desired mating region of the patient's actual femur in a manner that causes the axis of the guide hole 65 to be coaxially aligned with the actual axis 100 of the actual patient's femur head and neck.

3. Method of Manufacture and Use

Figure 1B:
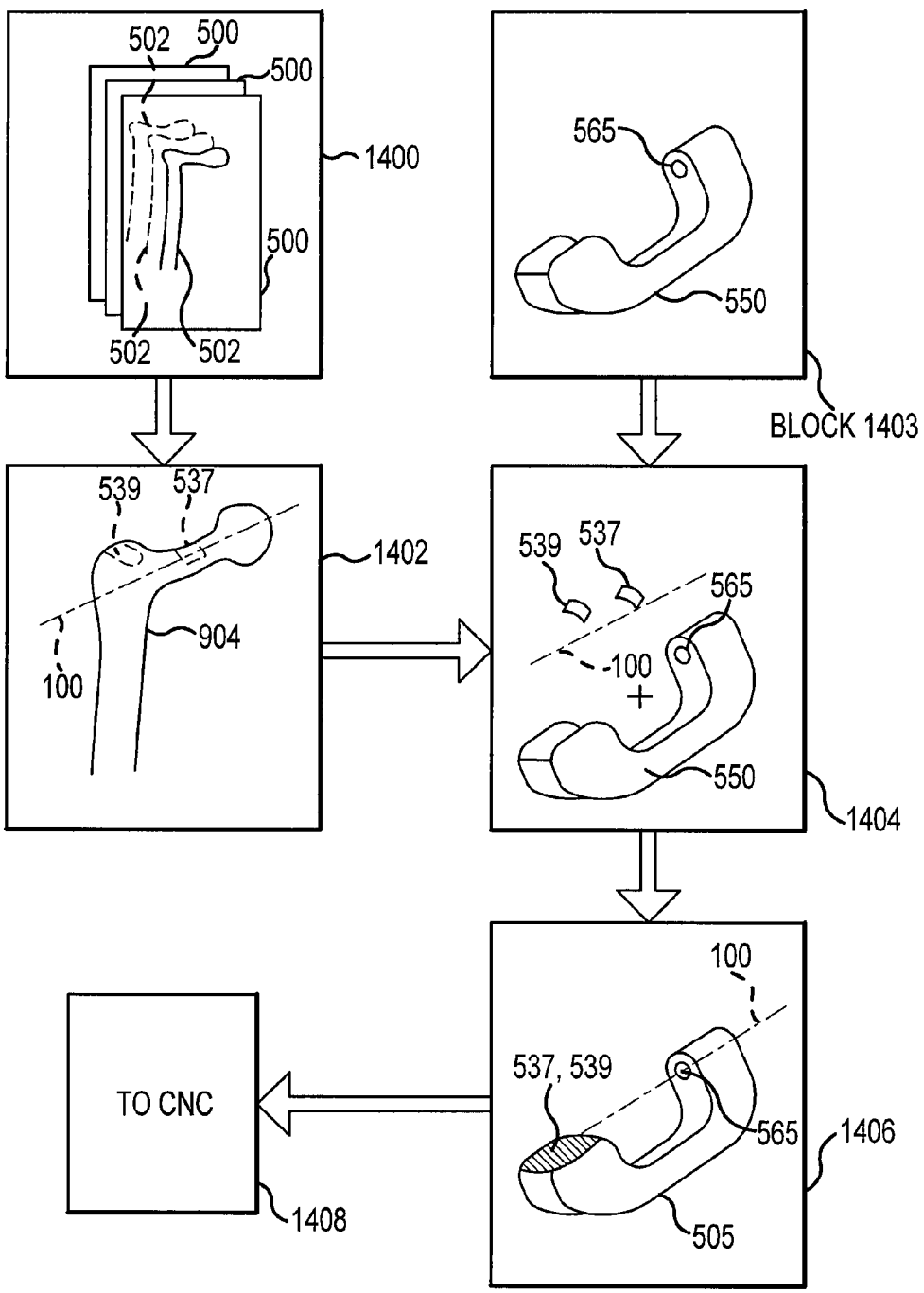
FIG. 1B is a diagrammatic depiction of a process of manufacturing some embodiments of the tool.
Figure 1C:
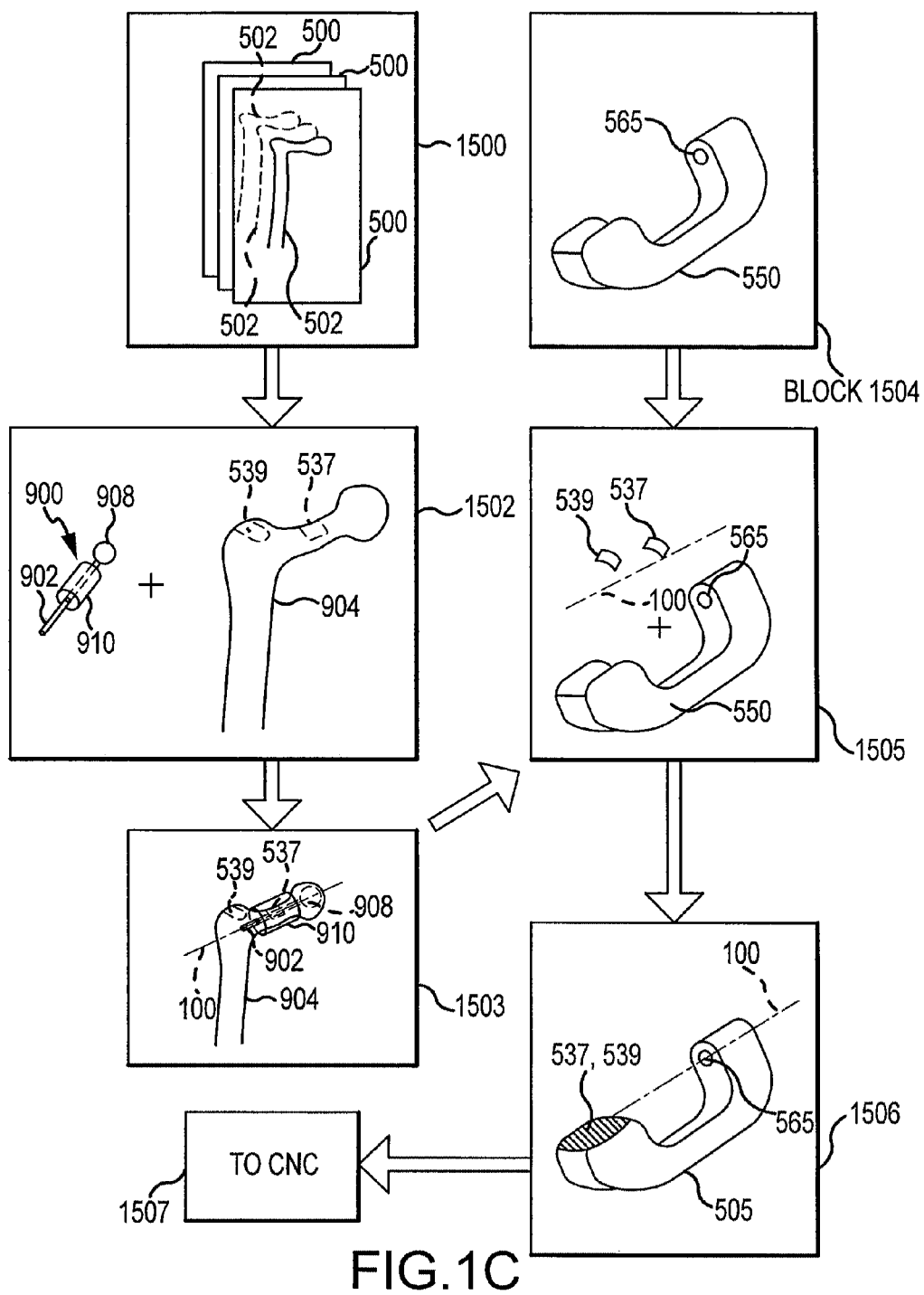
FIG. 1C is a diagrammatic depiction of another process of manufacturing some embodiments of the tool.
Figure 1D:
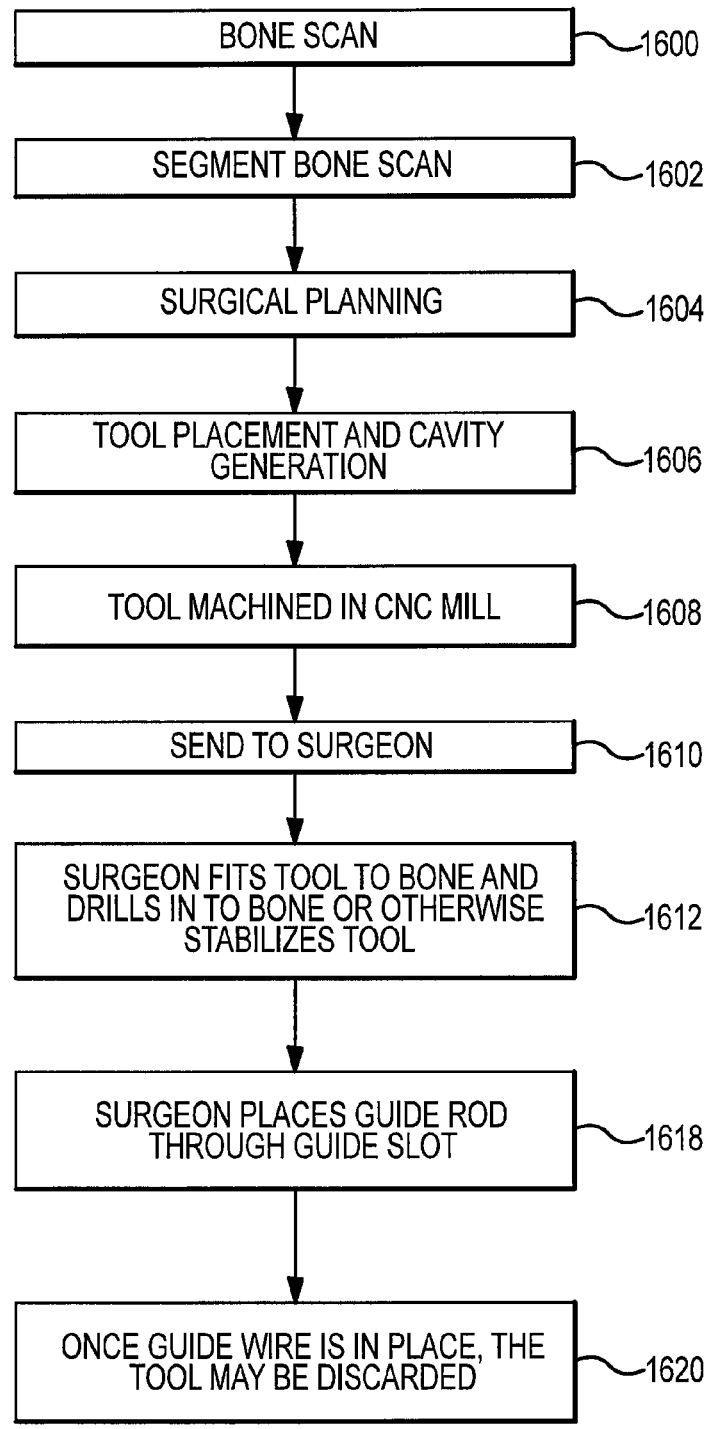
FIG. 1D is a flow chart describing a method of manufacturing and using a surgical guide tool as described herein.

For a discussion of a method of preoperatively planning and manufacturing the above-described tool 5, reference is made to FIGS. 1A-1B and 1D. FIG. 1A is a diagrammatic depiction of a system 4 for manufacturing a surgical guide tool 5 as described herein. FIG. 1B is a diagrammatic depiction of the process of manufacturing some embodiments of the tool 5. FIG. 1D is a flow chart describing a method of manufacturing and using a surgical guide tool 5 as described herein.

As can be understood from FIGS. 1A-1B and 1D, a process for producing the tool 5 may be as follows. CT or MRI image scans 500 are generated via a medical imaging machine 8 of the proximal femur 14 of the patient 12 and sent to the modeling system 6 [blocks 1400 and 1600]. Each image scan 500 may be subjected to a segmentation process to identify the femur contour line 502 depicted in the image scan 500 [block 1602]. Where the contour lines 502 correspond to regions of the femur contour that have rapidly changing geometry or geometry that is too small to be milled into or otherwise formed into the mating region 20 of the tool 5 (e.g., the non-mating surfaces 110, 111 discussed above), the contour lines 502 in such regions are subjected to an overestimation process as disclosed in U.S. Patent Application No. 61/083,053, entitled System and Method for Manufacturing Arthroplasty Jigs Having Improved Mating Accuracy, filed Jul. 23, 2008 and incorporated herein by reference in its entirety. Specifically, in one embodiment of the overestimation process, the contour lines 502 in such regions (e.g., 110, 111) are adjusted outwardly away from the interior region of the bone and potentially smoothed with respect to contour line variance.

Figure 6:
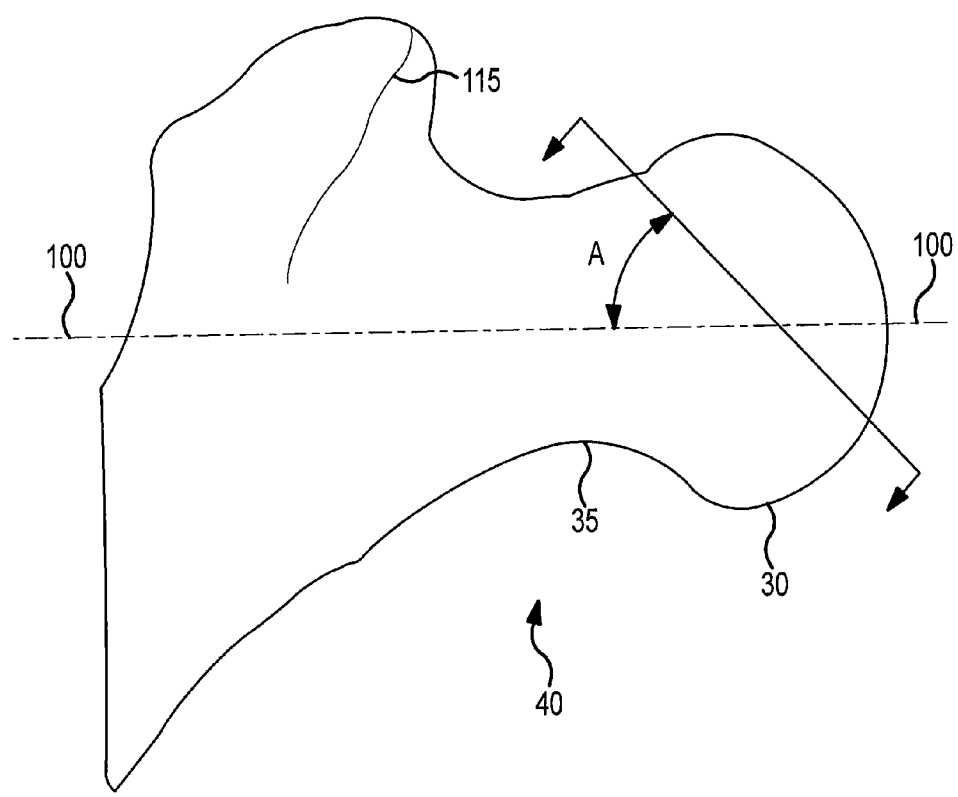
FIG. 6 is a side view of a 3D computer generated model of the proximal femur, including its femoral head, neck and greater trochanter, illustrating the angle A at which the bone scan is segmented or sectioned.
Figure 7A:
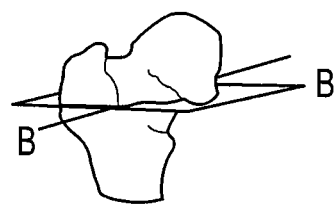
FIG. 7A is a 3D view of the proximal femur of FIG. 5A, illustrating a section plane B at which the bone is sectioned during a CT scan to help delineate mating and non-mating regions.
Figure 7B:
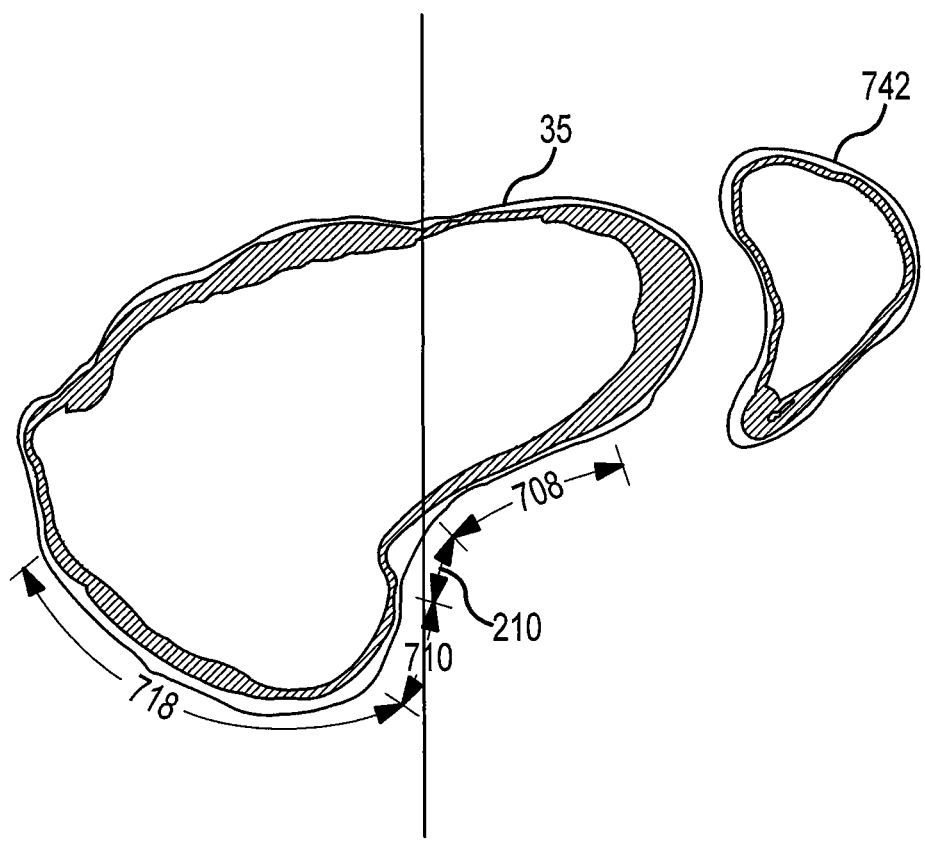
FIG. 7B is a CT slice as taken along section plane B of FIG. 7A.
Figure 8A:
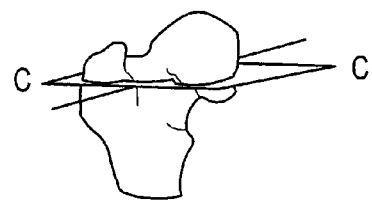
FIG. 8A is a 3D view of the proximal femur of FIG. 5A, illustrating a section plane C at which the bone is sectioned during a CT scan to help delineate mating and non-mating regions.
Figure 8B:
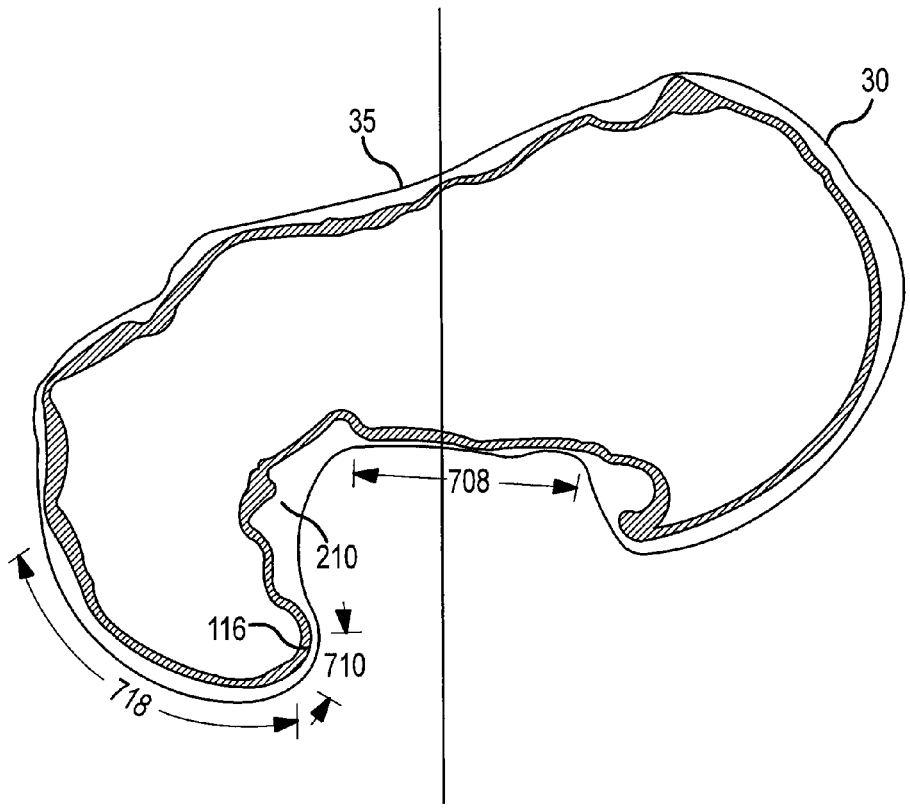
FIG. 8B is a CT slice as taken along section plane C of FIG. 8A.
Figure 9A:
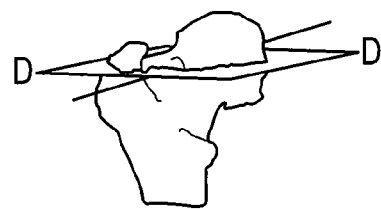
FIG. 9A is a 3D view of the proximal femur of FIG. 5A, illustrating a section plane D at which the bone is sectioned during a CT scan to help delineate mating and non-mating regions.
Figure 9B:
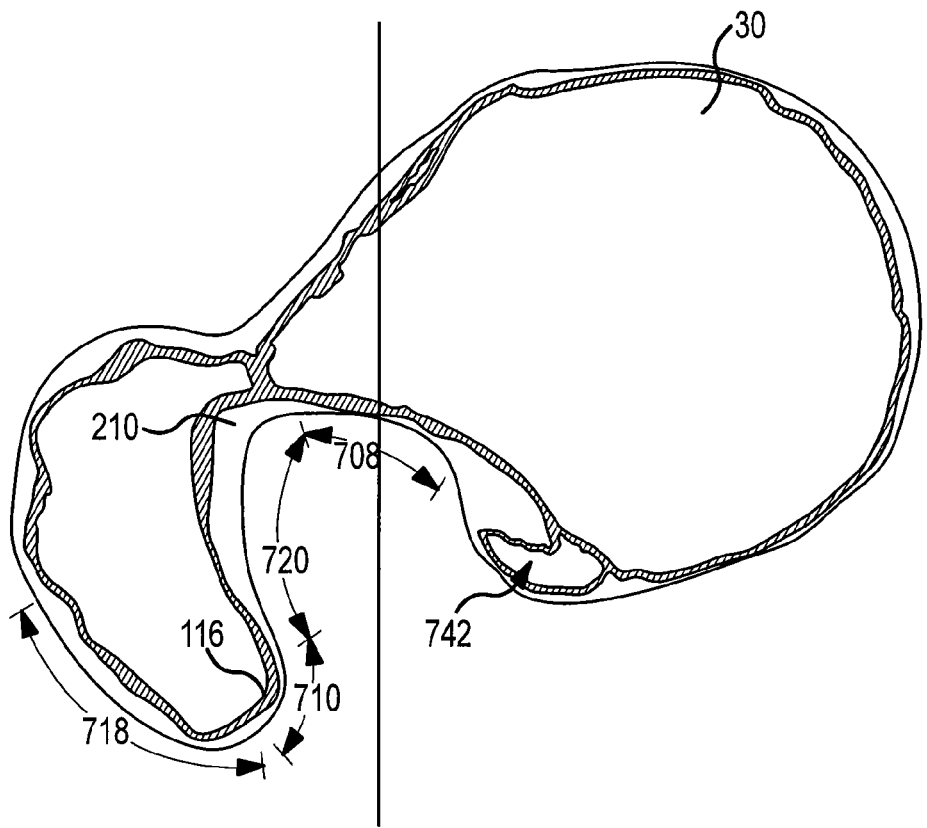
FIG. 9B is a CT slice as taken along section line D of FIG. 9A.

As can be understood from FIG. 6, which is a side view of a 3D computer generated model of the proximal femur 40, including its femoral head 30, neck 35 and greater trochanter 115, the femur may be segmented or sectioned during or after the imaging process at an angle A relative to the axis 100 of the femur. More specifically, in one embodiment, segmentation is performed utilizing slices or sections at an angle A off the central axis 100 of the femoral neck 35 viewed posteriorly. The segmentation can be done in several ways and for ease of the reader are described in relation to a CT-scan. It can be appreciated that segmentation of an MRI scan may be achieved in a similar manner. For example, the CT locator could be positioned at an angle A to section the CT scan. Alternatively or additionally, the CT scan could be sectioned at an angle A during post-processing. In one embodiment, the angle A is between approximately thirty degrees and approximately sixty degrees. In an alternative embodiment, the angle A is approximately a forty-five degree angle.

Once any overestimation is done for a specific contour line 502, the contour line 502 may be a combination of overestimated portions and portions that are not modified. Subsequent to the overestimation process, the various contour lines 502 from the various scans 500, which may be a combination of scan images with no adjustment to their respective contour lines and scan images that have undergone the overestimation process, are compiled via a 3D computer modeling program loaded on the modeling system 6 into a 3D bone model 904 of the proximal femur [block 1402].

To begin the preoperative planning process [block 1604], the bone model 904 may be analyzed as discussed above with respect to FIG. 3 to determine the central axis 100 through the centroids 135 of the transverse centroid cross-sections 130 of the neck 35 and head 30 of the bone model 904 of the femur 40. The bone model 904 may also be analyzed to determine indexing or mating surfaces 537, 539 (corresponding to femur mating surfaces such as, for example, 37, 38, 39 in FIG. 3) that will be determined and imported into a tool blank model 550 and be used to form the indexing surfaces 101, 102, 103 in the mating region 20 of the actual tool 5, as indicated in FIGS. 2A-2F. A tool blank model 550 is provided [blocks 1403 and 1606]. In one embodiment, the surfaces 537, 539 and axis 100 are positionally correlated and referenced with respect to each other and imported as a unit into the tool blank model 550 such that the axis 100 coaxially aligns with the axis of the guide hole 565 in the blank model 550, thereby creating a tool model 505 [blocks 1404, 1406 and 1606]. The tool model 505 is used to create milling tool paths that are sent to the CNC machine 10 [block 1408]. The CNC machine 10 uses the milling paths to generate the customized tool 5 of FIG. 2C from a tool blank 250 [block 1608]. Post processing of the tool may include cutting the tool away from the struts that may or may not be part of the blank and smoothing around the edges. The finished tool may then be shipped to the surgeon [block 1610].

As can be understood from FIGS. 1C and 2A-2F, during surgery, the surgeon may fit the tool 5 appropriately on the femur such that the tool index surfaces 101, 102, 103 matingly contact the corresponding femur mating surfaces 37, 38, 39 and the tool overestimated or non-contact surfaces 22, 24 do not contact the femur non-contact surfaces 110, 111 when the tool mating region 20 matingly receives the mating region of the femur 20. Once the tool 5 is appropriately fit to the femur 40, the surgeon drills into the two openings 82 at the mating end 50 of the tool 5 and insert fastening members 80 to stabilize the tool 5 on the femur 40 [block 1612]. Once tool 5 is appropriately positioned and secured to the femur 40, the surgeon may place the guide rod 70 through the guide rod receiving opening 65 and prepare to drill the hole for the guide wire 75 [block 1618]. Once the guide wire 75 is in place, the fastening members 80 at the mating end 50 of the tool 5 may be removed and the tool 5 may be discarded [block 1620]. The surgeon may then utilize the guide wire 75 to guide the resurfacing process used to prepare the femur head for the resurfacing prosthetic implant.

Some embodiments of the hip resurfacing tool, such as those discussed with respect to FIGS. 2A-4, may be for a posterior approach and designed based at least partially upon determining the central axis through the femur head and neck via a centroid determination process. In other embodiments, the hip resurfacing tool 5 may be for a posterior or an anterolateral approach and at least partially designed based on a 3D computer model of the actual resurfacing component (i.e. a planning pin model 900) to help determine the central axis through the femur head and neck. Such an embodiment will now be discussed in the following sections of this Detailed Description.

B. Surgical Guide Tool for a Posterior or Anterolateral Approach

Figure 5A:
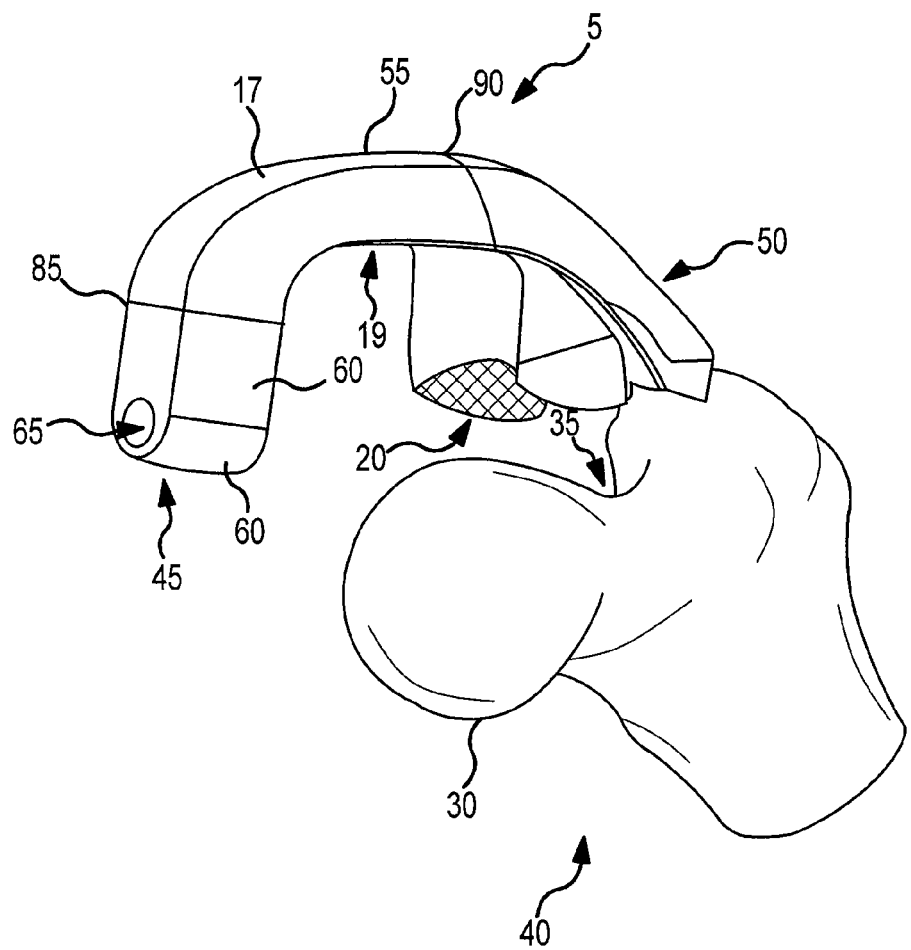
FIG. 5A is an isometric view of another embodiment of a surgical guide tool and a proximal femur with its femoral head, neck and greater trochanter, wherein the tool may be used in either an anterolateral approach or a posterior approach during a hip resurfacing procedure.
Figure 5B:
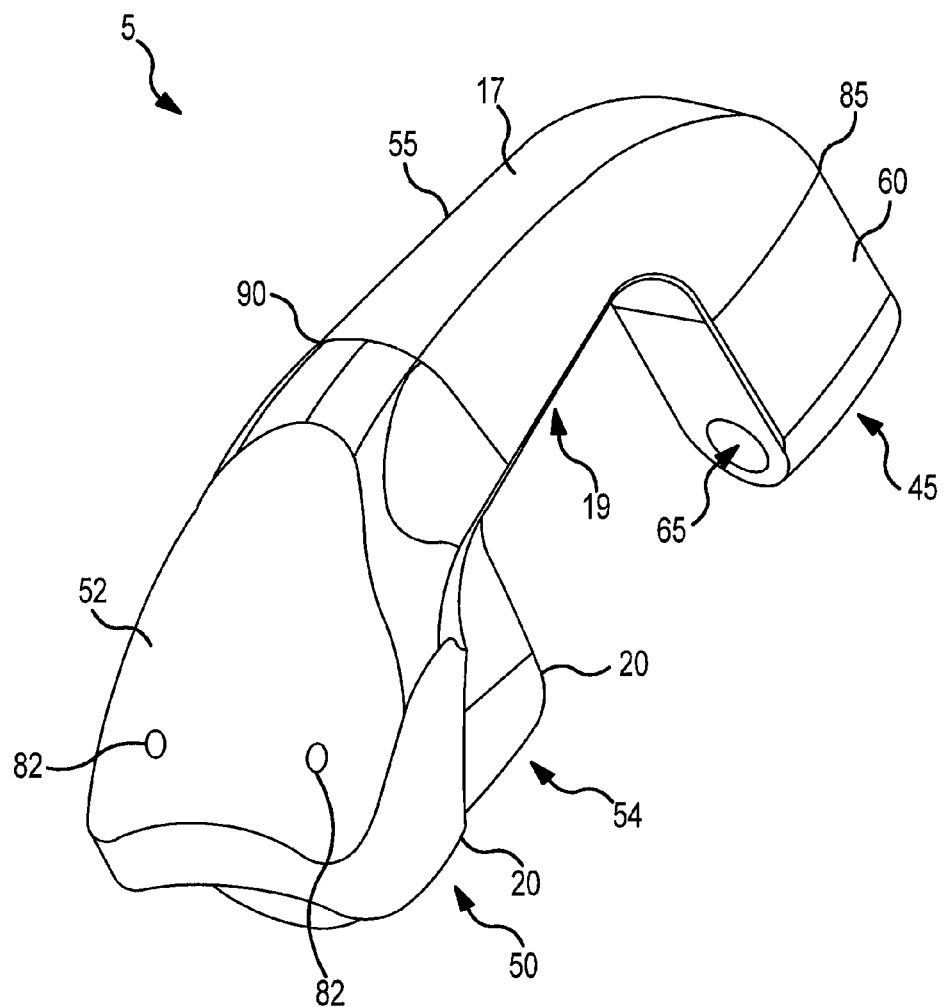
FIG. 5B is a side top isometric view of the surgical guide tool of FIG. 5A, wherein the tool is in a non-customized state or is the form of a blank from which the customized tool is generated via a CNC milling machine.
Figure 5C:
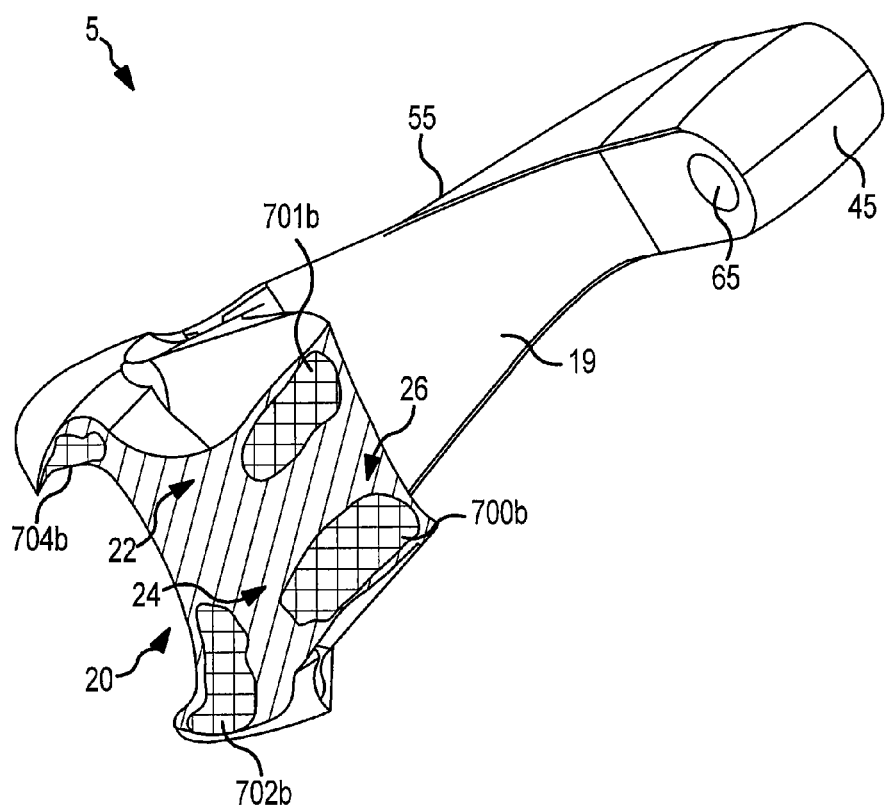
FIG. 5C is a side bottom isometric view of the surgical guide tool of FIG. 5A, wherein the tool is in a customized state.
Figure 5D:
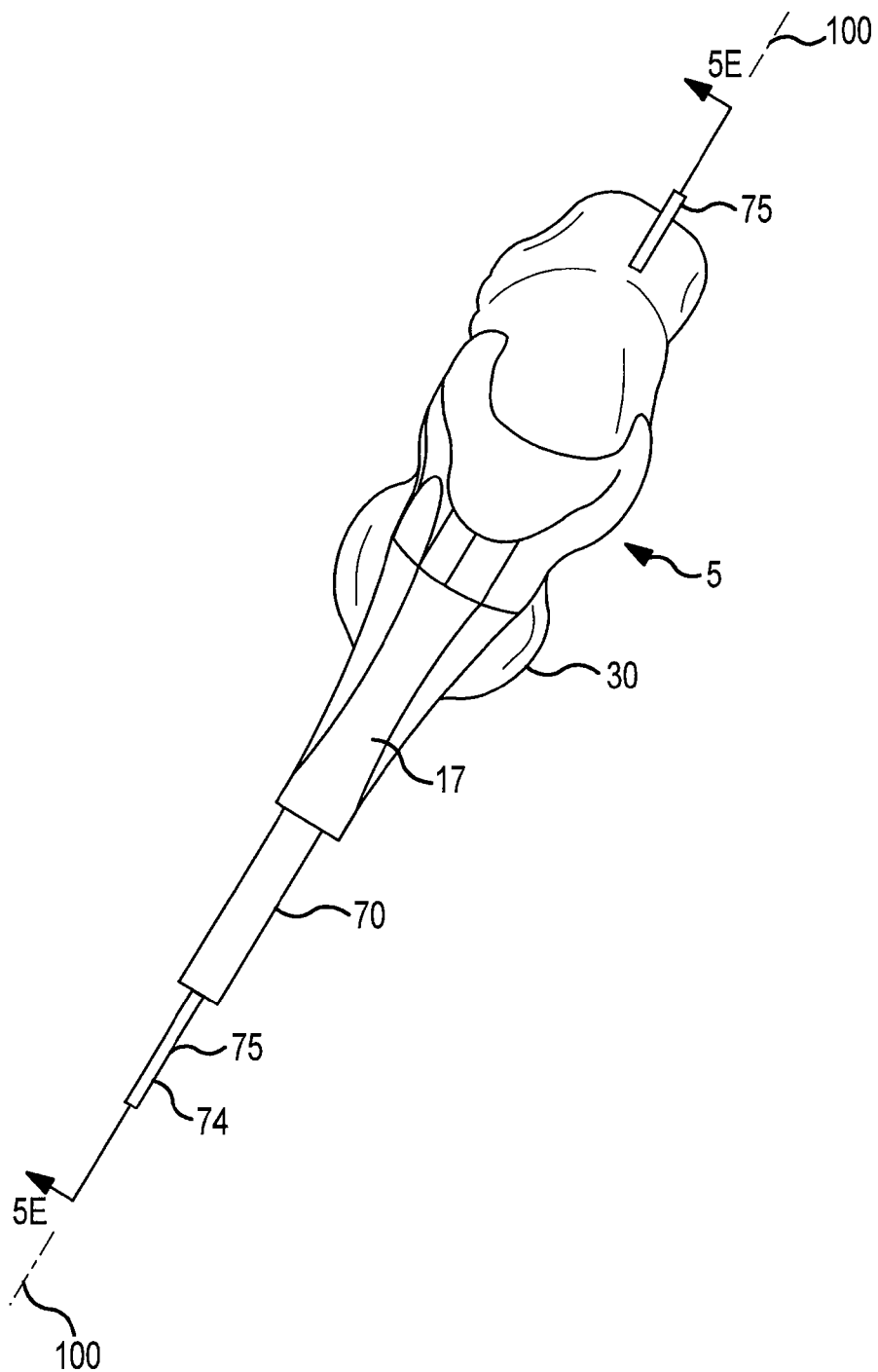
FIG. 5D is a top plan view of the surgical guide tool and the femur of FIG. 5A, wherein the tool is shown mounted on the femur.
Figure 5E:
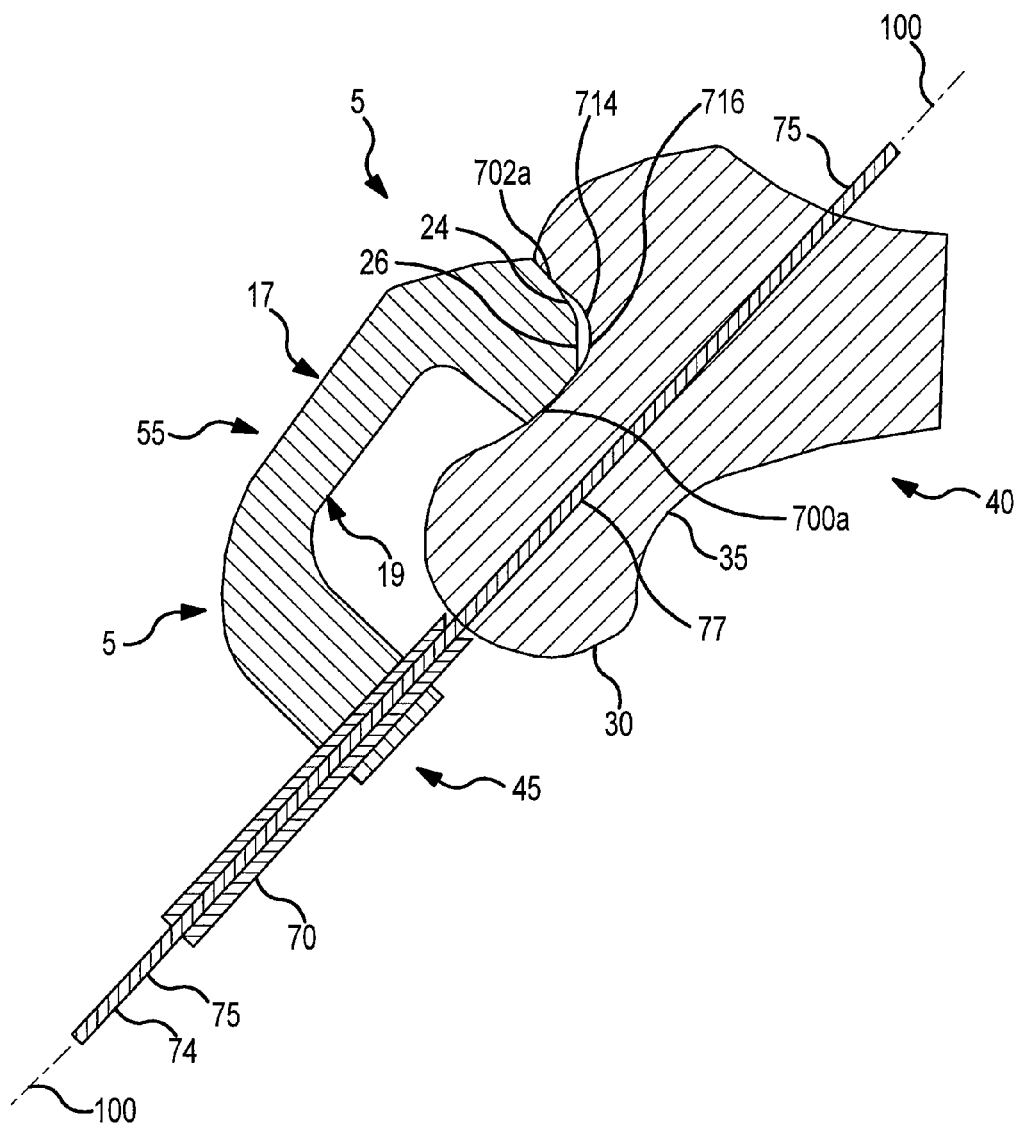
FIG. 5E is a longitudinal cross-section of the surgical guide tool and femur as taken along section line 5E-5E of FIG. 5D and corresponding to the path of line 14A-14A of FIG. 14A.

For a general discussion of features of an embodiment of the tool 5 that may be used in a posterior or an anterolateral approach and may utilize a computer model of the resurfacing component to determine the central axis through the femoral head and neck, reference is first made to FIGS. 5A-5E. FIG. 5A is an isometric view of the surgical guide tool 5 and a proximal femur 40 with its femoral head 30, neck 35 and greater trochanter. FIG. 5B is a side top isometric view of the surgical guide tool 5 in a non-customized state or in the form of a blank from which the customized tool 5 is generated via a CNC milling machine. FIG. 5C is a side bottom isometric view of the surgical guide tool 5 of FIG. 5A, wherein the tool 5 is in a customized state. FIG. 5D is a top plan view of the surgical guide tool 5 and the femur 40 of FIG. 5A, wherein the tool 5 is shown mounted on the femur 40. FIG. 5E is a longitudinal cross-section of the surgical guide tool 5 and femur 40 as taken along section line 5E-5E of FIG. 5D and corresponding to the path of line 14A-14A of FIG. 14A.

As illustrated in FIGS. 5A and 5B, in one embodiment, the surgical guide tool 5 includes a mating end 50, a head end 45 and a connecting arm 55. In one embodiment, the ends 45, 50 and the connecting arm 55 are formed or otherwise joined together such that the tool 5 is a single-piece tool having a single-piece construction that is generally unitary and continuous in nature. In other embodiments, the tool 5 will have a multi-piece construction formed of two or more individual pieces joined together in preparation for, or in the course of, being mounted on a femur during a HRS.

As can be understood from FIG. 5C and as will be discussed with respect to FIGS. 14A-16B later in this Detailed Description, the mating end 50 may include a mating region 20 adapted to receive therein and mate with surfaces of the proximal femur 40 that are available based on the surgical approach, such as, for example, the superior-posterior region 700a of the neck 35, the superior-anterior region 701a of the neck 35, a region 702a bordering the intertrochanteric crest 116, a region 704a of the anterior greater trochanter 115, a region 706 that may extend past the intertrochanteric crest 116, from the lesser trochanter 740 to the superior tip 215 of the greater trochanter 115 on the posterior side and past the intertrochanteric line 738 on the anterior side as well as the medial surface 216 of the greater trochanter 115, a region 708 covering portions of the posterior region of the neck 35, and a region 710 which is a narrow band following along the intertrochanteric crest 116. The surfaces 700a, 701a, 702a, 704a, 706, 708, 710 to be mated or indexed by the tool index surfaces 700b, 701b, 702b, 704b of the mating region 20 may be separated by areas of non-mating surfaces 712, 714, 716, 718, 720 that are spanned by non-contacting surfaces 22, 24, 26 of the mating region 20 of the tool 5 and which are also determined by the regions exposed by the surgical approach. The non-contacting surfaces 22, 24, 26 of mating region 20 the tool 5 have surfaces that do not contact the non-mating surfaces 712, 714, 716, 718, 720 and may be generated via an over-estimating process during image segmentation as described later in this Detailed Description. The non-mating surfaces 712, 714, 716, 718, 720 of the proximal femur 40 may be surfaces 712 of the tubercle 730 of the femur 40, surface portions 714 of the trochanteric fossa 210 (i.e., the depression between the greater trochanter and the femur neck), surface 716 which may contain the superior junction 728 between the posterior and anterior surfaces of the neck 35, region 718 which may include portions of the posterior greater trochanter 116, and region 720 which may span portions of the trochanteric fossa 210.

For ease of the reader, the mating end of the tool 5 as shown in FIGS. 5A-5E is discussed with reference to the mating regions 700a, 701a, 702a, 704a of FIG. 14A-14B. In other embodiments, the tool 5, and more specifically the mating region 20 of the mating end 50, may be configured to have mating surfaces that correspond to other mating surface arrangements of the femur as depicted in FIGS. 4, 15, and 16A-16B. Also, in general, any surface of mating region 20 that is outside of tool mating surfaces 700b, 701b, 702b, 704b may be tool non-contacting surfaces 22, 24, 26 which correspond to non-contacting surfaces 712, 714, 716 of the femur.

As can be understood from FIGS. 5A-5E, the head end 45 includes a guide hole 65 and is configured to be positioned adjacent to the femoral head 30 without contacting the femoral head 30 and, more specifically, to position the guide hole 65 near the center of the spherical surface of the femur head 30. In some embodiments, the head end 45 may contact the surface of the femoral head 30 while still positioning the guide hole 65 near the center of the spherical surface of the femur head 30. The connecting arm 55 extends from the mating end 50 to the head end 45, thereby connecting the ends 50, 45. The tool 5 may be made of polyoxymethylene (acetal resin), a low density polyethylene, or other biocompatible plastics.

As shown in FIGS. 5A and 5B, the connecting arm 55 includes a top face 17 and a femur face 19, a first end 85 and a second end 90. In one embodiment, as best understood from FIG. 5E discussed in more detail below, the femur face 19 of the arm 55 is generally a rectangular-shaped arch and the top face 17 of the arm 55 is generally arcuate. The arm 55 is configured to generally extend across the femoral head 30 without contacting the head 30. That is, the arm 55 extends between, and thereby connects, the head and mating ends 45, 50 but does not contact the external surface of the head 30. In some embodiments, the arm 55 may contact the external surface of the head 30 or other portions of the proximal femur 40. In some embodiments, the femur face 19 of the arm 55 may not be a rectangular-shaped arch, but may be an arcuate shape to enable the tool 5 to fit or more closely follow along the femoral region as described herein.

As can be understood from FIGS. 5A-5B, the head end 45 of the tool 5 includes a semi-circular or U-shaped end 60 and at least one guide hole 65. The U-shaped end 60 generally extends from the first end 85 of the connecting arm 55 to approximately the center of the spherical surface of the femoral head 30 without contacting the head 30. In some embodiments, the U-shaped end 60 may contact an external surface of the femoral head 30.

The guide hole 65 of the head end 45 extends axially through the head end 45 and may have a cylindrical construction. As can be understood from FIGS. 5C-5E, discussed in more detail below, the guide hole 65 of the head end 45 defines a passageway to receive a guide rod 70 through which a drill 74 is extended during surgery to drill a hole 77 through the femur head 30 and femur neck 35 along the central axis 100 thereof. Once the hole 77 is complete, the drill 74 can be removed and replaced with a guide wire 75 that may be used as a reference post for the resurfacing devices employed in preparing the femur head 30 to receive the prosthetic resurfacing component 600.

In one embodiment, the tool 5 may be adapted to receive therein and mate with the proximal femur 40 and, more specifically, limited and predetermined surfaces 700a, 701a, 702a, 704a, 706, 708, 710 (depending on the surgical approach) of the proximal femur 40.

As can be understood from FIGS. 5A and 5B, the mating end 50 of the tool 5 includes a top side 52 and a femur side 54. A portion of the top side 52 and the femur side 54 of the mating end 50 includes a customizable or mating region 20, which, as depicted in FIG. 5C and with reference to FIGS. 14A-14B, may include one or more indexing or mating surfaces 700b, 701b, 702b, 704b configured to matingly receive portions of the proximal femur 40 such as surfaces 700a, 701a, 702a, 704a of the proximal femur 40 as discussed with respect to FIGS. 14A-14B.

As shown in FIG. 5B, the mating end 50, when in a non-customized state such as when the tool 5 exists as a blank from which the tool 5 is machined, includes a generally arcuate top side 52 and a generally U-shaped or rectangular shaped femur side 54. In some embodiments, the mating end 50 may include fastening member-receiving openings 82 (which are configured to receive fastening members) for securing the tool 5 to the proximal femur 40 when the indexing surfaces 700b, 701b, 702b, 704b of the mating region 20 matingly receive the corresponding bone surfaces 700a, 701a, 702a, 704a, 706, 708, 710. In some embodiments, the mating end 50 may be secured to the proximal femur 40 without fastening members and instead simply by the indexing surfaces 700b, 701b, 702b, 704b of the mating region 20 matingly receiving the corresponding bone surfaces 700a, 701a, 702a, 704a or by the surgeon or other medical personnel securing the tool 5 in place.

As described in more detail below, the mating region 20 of the tool 5 may be customized based on a patient's individual bone shape. The tool 5 may be machined, molded or otherwise formed from the non-customized state as illustrated in FIG. 5B to a customized state as indicated in FIG. 5C, based on a patient's individual bone scan, for example an MRI scan or CT-scan. For example, the bone scan data may be utilized to generate a 3D computer generated model of the patient's proximal femur. A 3D computer generated model of a resurfacing component 600 and a 3D computer generated model of the tool blank may be superimposed onto and properly aligned with the 3D bone model to preoperatively plan the patient specific tool 5. That is, through the information received from the MRI scan or CT-scan and the computer modeling, the tool 5 may be customized at the mating region 20 such that the tool 5 will have mating or indexing surfaces 700b, 701b, 702b, 704b of the mating region 20 that generally conform to the predetermined specific surface geometry of the patient's own proximal femur 40. In some embodiments, the predetermined specific geometry will be that of surfaces 700a, 701a, 702a, 704a discussed with respect to FIGS. 14A-14B. In some embodiments, the predetermined specific geometry will be that of surface 706 discussed with respect to FIGS. 16A-16B. In some embodiments, the predetermined specific geometry will be that of surfaces 708, 710 discussed with respect to FIG. 15. In some embodiments, the predetermined specific geometry will be that of surfaces 37, 38, 39 discussed with respect to FIG. 4. In some embodiments, the predetermined specific geometry will be various combinations of the aforementioned mating surfaces in FIGS. 4 and 14A-16B, portions of those aforementioned mating surfaces, or other surfaces capable of offering the similar modeling, mating and manufacturing characteristics as the aforementioned mating surfaces. The customized mating surfaces ensure that the mating region 20 can properly matingly receive the corresponding regions of the proximal femur. The positional correlation between the axis of the guide hole 64 and the aforementioned mating surfaces of the mating region 20 ensures the drill hole 77 (see FIG. 5E) will extend along the central axis 100 of the femur head 30 and neck 35, thereby increasing the accuracy of the femur head resurfacing procedures indexed off of the hole 77 and the placement of the prosthetic surface 600 implanted on the resurfaced femur head as part of a HRS.

Figure 14A:
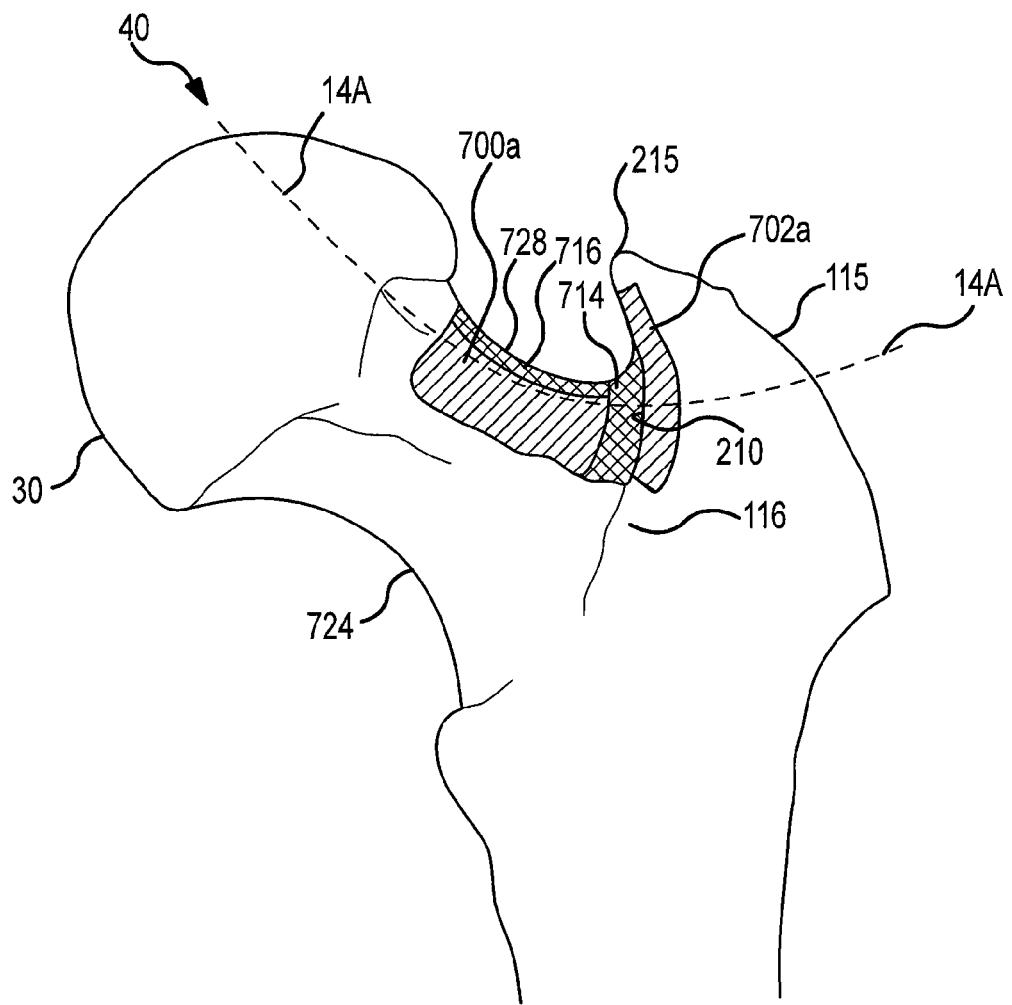
FIG. 14A is a posterior view of the proximal femur of FIG. 5A showing the surfaces of the femur that are mated with the index surfaces of an embodiment of the tool and the surfaces that correspond to over-estimated or non-contacting surfaces of the tool, for use with either an anterolateral or posterior approach during a hip resurfacing procedure.
Figure 14B:
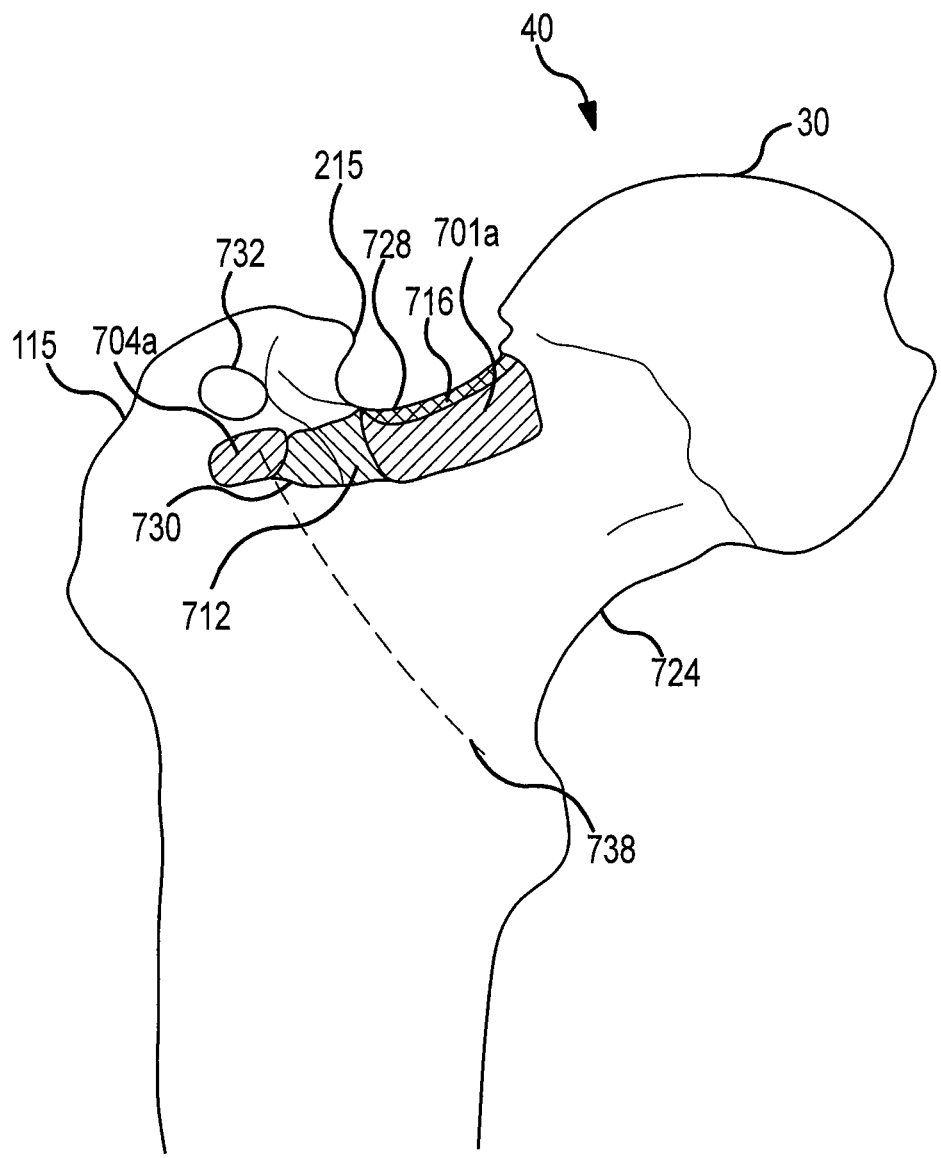
FIG. 14B is an anterior view of FIG. 14A.

As mentioned above, creation of the customized tool 5 (see FIG. 5C) is discussed with respect to FIGS. 14A-14B. However, it is understood that the tool 5 may be customized to correspond with any of the mating and non-mating surfaces disclosed herein, such as those depicted in FIGS. 4, 15 and 16A-16B. As can be understood from FIG. 5C and with reference to FIGS. 14A-14B, the mating end 50 of the tool 5 may be adapted to receive therein and mate with surfaces of the proximal femur 40, such as, for example, portions of the superior posterior surface 700a of the neck 35, a superior anterior surface 701a of the neck 35, a surface 702a that follows along the intertrochanteric crest 116 and a surface 704a that lies on the anterior greater trochanter 115. The femur surfaces 700a, 701a, 702a, 704a to be mated or indexed by the tool index surfaces 700b, 701b, 702b, 704b of the mating region 20 may be separated by areas of non-mating femur surfaces 712, 714, 716 that are spanned by non-contacting surfaces 22, 24 of the mating region 20 of tool 5. The non-contacting surfaces 22, 24, 26 of the mating region 20 of the tool 5 have surfaces that are spaced apart from the non-mating femur surfaces so as to not contact the non-mating femur surfaces 712, 714, 716 when the mating region 20 matingly receives the corresponding region of the femur.

These tool non-mating surfaces 22, 24, 26 may be generated via an overestimating process during image segmentation. Specifically, during the image segmentation process wherein the bone contour lines are identified in each medical imaging slice, the contour lines are moved outward from the interior region of the bone and, in some cases, variations in the contour lines are reduced to result in a smoother line contour. When the contour lines are combined into the 3D computer generated bone model, the regions of the bone model corresponding to the portions of the contour lines subjected to the overestimation process are further from the interior of the bone than they would otherwise be and, in some cases, present a generally smoother surface than the actual bone in corresponding areas. Thus, non-mating surfaces 22, 24, 26 of the tool 5 resulting from the overestimated regions of the bone model (e.g., those areas corresponding to regions 712, 714, 716) will end up being spaced apart from the patient's bone when the mating region 20 matingly receives the patient's femur.

The non-mating surfaces of the patient's femur may correspond to those surface areas having rapidly changing topography and/or those surface areas that are difficult or impossible to machine or manufacture due to their size or configuration. Examples of such areas may be non-mating surfaces 712, 714, 716 of the proximal femur 40. Non-mating surface 712 may include portions of the tubercle 730 of the femur 40. Non-mating surface 714 may include portions of the trochanteric fossa 210 (i.e., the depression between the greater trochanter and the femur neck). Non-mating surface 716 may include portions of the superior junction 728 between the posterior and anterior surfaces of the neck 35.

As can be understood from FIG. 5C, the mating region 20 of the tool may be placed to cover or matingly receive the area encompassing the mating surfaces 700a, 701a, 702a, 704a of the proximal femur 40. As discussed above, non-mating surfaces 712, 714, 716, including portions of the trochanteric fossa 210 (the depression between the greater trochanter and the neck of the femur) and portions of the tubercle 730, are not easily estimated due to drastic changes in surface geometry. Corresponding non-mating surfaces 22, 24, 26 of the mating region 20 of the tool 5 may be configured to be spaced away from and not contact these surfaces 712, 714, 716 of the femur 40. Once the tool is positioned, a cavity or mating region 20, which has index surfaces 700a, 701a, 702a, 704a, is created in the non-customized tool of FIG. 5B. The cavity or mating region 20 conforms to the segmented CT scan or MRI scan of the patient's femur, thereby creating the customized tool as shown in FIG. 5C.

As shown in FIGS. 5D-5E, during surgery, the guide rod 70 is received in the guide rod-receiving opening or guide hole 65 in the head end 45 of the tool 5. The guide rod 70 is configured to receive the drill bit 74 and guide wire 75. The guide rod 70 may be made of surgical stainless steel or titanium. The guide wire 75 may be made of surgical stainless steel or titanium.

As can be understood from FIGS. 5D-5E, and with reference to FIGS. 5C and 14A-14B, by securely mounting the tool 5 on the femur 40 such that the tool index surfaces 700b, 701b, 702b, 704b matingly contact corresponding surfaces 700a, 701a, 702a, 704a of the femur 40, the guide hole 65 is properly aligned to guide a drill bit in forming a hole 77 that is coaxially aligned with a central axis 100 of the femur head 30 and neck 35. Proper alignment of the hole 77 with the axis 100 prevents or at least minimizes the chances of several undesirable complications. For example, failure of the hole 77 to properly align with the axis 100 can cause the femoral neck to become prone to fracture. Additionally, failure of the hole 77 to properly align with the axis 100 can cause the drill bit 74 to hit the femoral artery when drilling the hole 77. The femoral artery is the only blood supply to this region of the femur and if severed, the hip will develop avascular necrosis.

During surgery, and with reference to FIG. 1D, the surgeon may fit the tool appropriately on the femur and in one embodiment, drill into openings 82 at the mating end of the tool and insert fastening members to stabilize the tool [block 1612]. In some embodiments, the tool 5 may be held in place by the surgeon or other medical personnel. Once positioned, the surgeon may place the guide rod through the guide rod receiving opening and prepare to drill the hole for the guide wire [block 1618]. The guide rod 70 is inserted in the guide rod-receiving opening 65 to aid the surgeon in aligning the drill 74 for accurately forming the reference hole 77 in the femur 40. A guide wire 75 may be placed in the hole 77 and used to guide the devices used in resurfacing the spherical surface of the femur head 30 in preparation for receiving the spherical prosthetic surface to be mounted on the resurfaced femur head (e.g. the resurfacing component 600). Once the guide wire is in place, the fastening members at the mating end of the tool may be removed or the surgeon or other medical personnel may discontinue holding the tool in place and the tool may be discarded [block 1620]. The surgeon may then place the hip surface replacement 600 as chosen during the planning step (described below with reference to FIGS. 1A and 1C-1D and FIGS. 13A-13F) and do so more accurately with the single piece tool 5 than with conventional, multiple piece tools. Thus, the tool 5 aids the surgeon in accurately drilling the hole 77 to extend along the central axis 100 of the femur head and neck, thereby decreasing the risks commonly associated with hip surface replacement surgery, such as fractures to the femoral neck and damage to the femoral artery.

1. Pre-Operative Planning

In some embodiments, the proper orientation of the guide hole 65 may be such that a drill extended through the guide hole will extend along the central axis of the femoral head and neck. In some embodiments, the central axis of the femoral head and neck may be determined by analyzing transverse cross-sections of the head and neck and approximating the centroid of each cross-section (see discussion with respect to FIGS. 2A-4, and specifically, FIG. 3, which method may be applied similarly in this and other embodiments). In some embodiments, after determining the central axis based on the centroid method, the placement of the guide wire of a planning pin model may be adjusted to a more valgus position, if necessary. As discussed above, in a first portion of the process, a bone scan, such as a CT scan or an MRI scan, is obtained. The 2D scans may be reconstructed into a 3D bone model, which will be used in the second portion of the process to place the guide wire in a more valgus position and to determine the proper type and placement of a resurfacing component.

Figure 10:
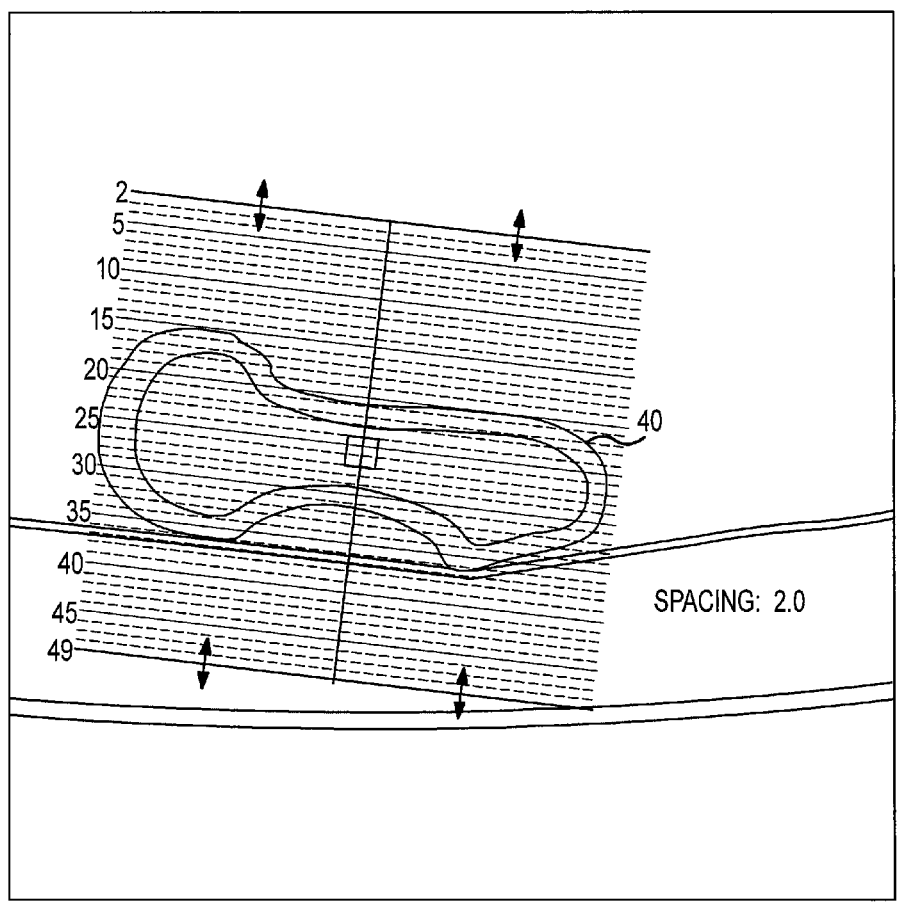
FIG. 10 is an exemplary CT scan of the proximal femur of FIG. 5A, wherein the correct coronal alignment for CT reconstruction is shown.
Figure 11:
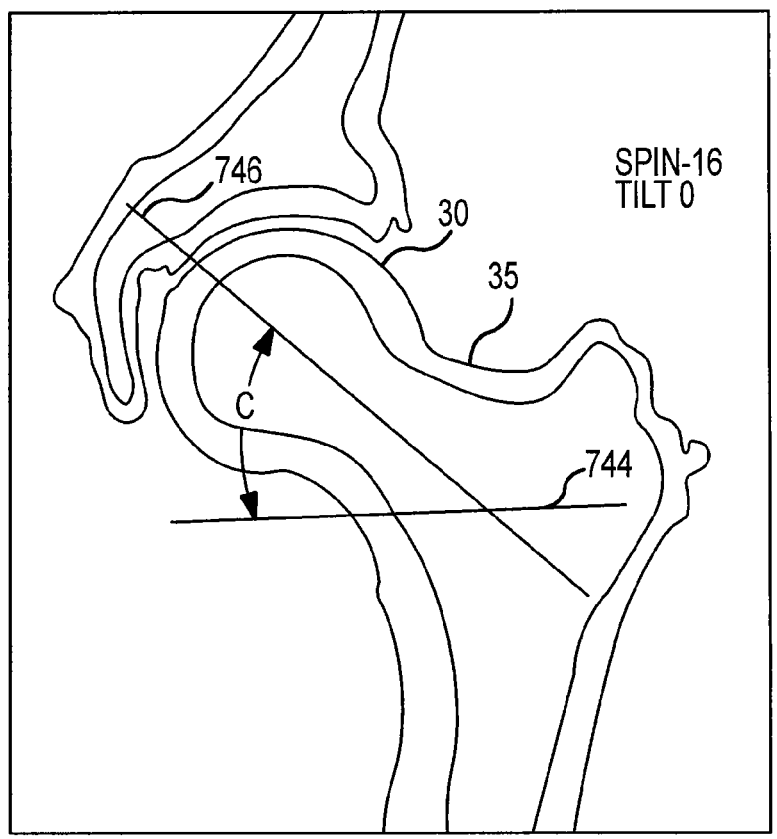
FIG. 11 is an exemplary CT scan of the proximal femur of FIG. 5A, wherein the correct alignment for the final CT reconstruction is shown.

For a discussion of one embodiment of the first portion of the process, reference is first made to FIGS. 6-11. FIG. 6 is a side view of a 3D computer generated model of the proximal femur 40, including its femoral head 30, neck 35 and greater trochanter 115, illustrating the angle A at which the bone scan is sectioned. FIG. 7A is a 3D view of the proximal femur 40 of FIG. 5A, illustrating a section line B at which the bone is sectioned during a CT scan to help delineate mating regions 708, 710 and non-mating regions 718, 720. FIG. 7B is a CT slice as taken along section line B of FIG. 7A. FIG. 8A is the same view as FIG. 7A, except illustrating a section line C at which the bone is sectioned. FIG. 8B is a CT slice as taken along section line C of FIG. 8A. FIG. 9A is the same view as FIG. 7A, except illustrating a section line D at which the bone is sectioned. FIG. 9B is a CT slice as taken along section line D of FIG. 9A. FIG. 10 is an exemplary CT scan of the proximal femur 40 of FIG. 5A, wherein the correct coronal alignment for CT reconstruction is shown. FIG. 11 is an exemplary CT scan of the proximal femur 40 of FIG. 5A, wherein the correct alignment for the final CT reconstruction is shown.

As discussed above, and with reference to FIGS. 1A, 1C and 1D, a first step in product development using the tool design and manufacturing system 4 is to employ a medical imaging machine 8 to generate 2D scan images 500 via a bone scan, such as a CT scan or MRI scan, of the proximal femur 40 of the patient 12 [blocks 1500 and 1600]. In one embodiment, the scan may include up to one-third of the proximal femur 40, including the femoral head 30 and the lesser trochanter 740. As discussed in more detail below with respect to FIGS. 7A-9B and 14A-16B, the scan may also help to delineate between mating surfaces 700a, 701a, 702a, 704a, 706, 708, 710 and non-mating surfaces 712, 714, 716, 718, 720. The CT-scan or MRI scan decreases errors that may occur when the surgeon utilizes an x-ray and a ruler to estimate by observation the center-point of the femoral head and neck. The estimation errors inherent in an estimation by observation technique may lead to inaccurate placement of the hip surface replacement and may cause additional complications such as damage to the femoral artery or femoral neck instability, which may lead to fractures.

The resolution of a CT scan or a MRI scan is also greater than the resolution of the x-ray. Greater resolution leads to more accuracy in the design of the tool and hence, placement of the hip surface replacement. In some embodiments, the resolution of the scan is between approximately 0 mm and approximately 2 mm. In other embodiments, the resolution of the scan is between approximately 0.3 mm and approximately 0.6 mm. In one embodiment, a CT scan with a resolution of approximately 0.6 mm is utilized for creation of the tool. In one embodiment, a CT scan with a resolution of approximately 0.5 mm to 2 mm, with a tube current ranging from 200 to 400 mA and a tube voltage ranging from 120 to 140 kV and a direct field of view (DFOV) ranging from approximately 16 cm to approximately 26 cm is utilized for creation of the tool.

As indicated in FIG. 1D, after obtaining the CT or MRI scan images 500, the scan images 500 may be segmented to identify bone contour lines 502 in the scan images 500 [block 1602]. As shown in FIG. 6, in one embodiment, segmentation is performed utilizing slices or sections at an angle A off the central axis 100 of the femoral neck 35 viewed posteriorly. The segmentation can be done in several ways and for ease of the reader are described in relation to a CT-scan. It can be appreciated that segmentation of an MRI scan may be achieved in a similar manner. For example, the CT locator could be positioned at an angle A to section the CT scan. Alternatively or additionally, the CT scan could be sectioned at an angle A during post-processing. In one embodiment, the angle A is between approximately thirty degrees and approximately sixty degrees. In an alternative embodiment, the angle A is approximately a 45 degree angle.

As can be understood from FIG. 1C and FIGS. 7A-9B, in some embodiments, the contours 502 of the CT or MRI scans 500 in the vicinity of various drastic and abrupt changes in surface geometry in the proximal femur, for example, in the regions of the trochanteric fossa 210 and intertrochanteric crest 116, are modified to be extended outwardly (i.e., overestimated) to result in CNC tool paths that remove excess materials from the blank used to form the tool 5. Thus, for regions of the tool 5 that would: (1) be difficult to machine to correspond to regions of the femur 40 due to limitations in the milling process; or (2) be difficult to model because of limitations in the scanning or 3D computer modeling processes, the contour lines 502 for the corresponding image slices 500 are modified such that the CNC tool paths create surfaces of the tool 5 that do not contact the proximal femur 40.

Figure 15:
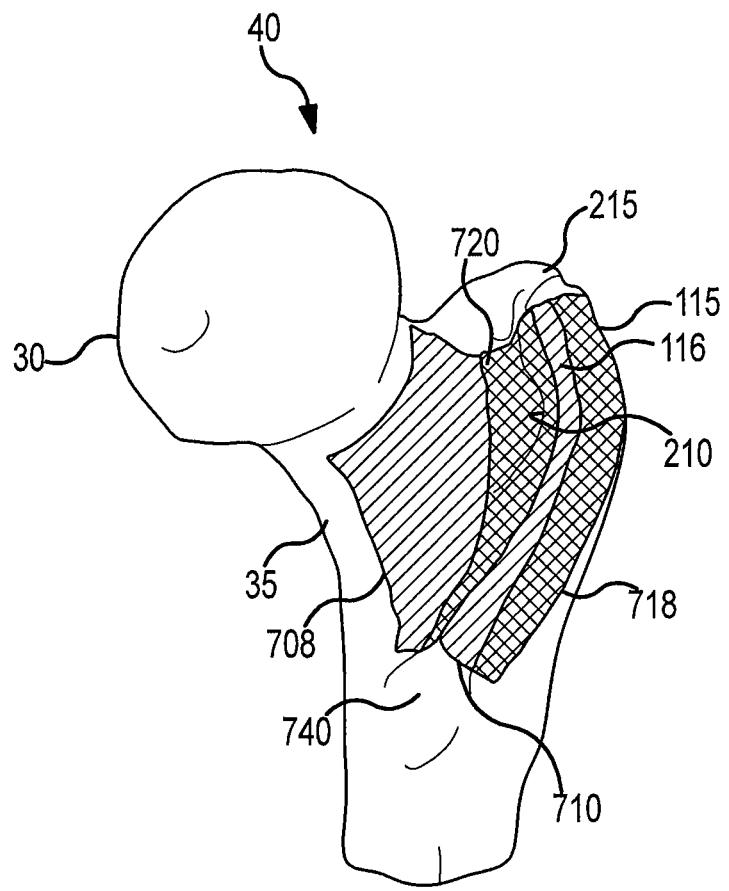
FIG. 15 is a posterior medial view of the proximal femur of FIG. 5A showing the surfaces of the femur that are mated with the index surfaces of another embodiment of the tool and the surfaces that correspond to over-estimated or non-contacting surfaces of the tool, for use with a posterior approach during a hip resurfacing procedure.

Thus, as can be understood from FIGS. 7A-9B, and with reference to FIG. 15, during segmentation, portions of contour lines 502 corresponding to femur non-mating surfaces 718, 720 and the surfaces of osteophytes 742 may be overestimated. As a result, non-mating tool surfaces 22, 24 corresponding to the overestimated portions of contour lines do not contact the corresponding non-mating surfaces 718, 720 of the bone. Through the overestimation process, portions of bone contour lines associated with mating surfaces 708, 710 may be delineated from portions of the bone contour lines associated with non-mating surfaces 718, 720.

Examples of non-contacting surfaces 22, 24, 26 of the tool 5 that may be the result of the over-estimating process can be seen in surfaces 22, 24, 26 in FIG. 5E, and these over-estimated surfaces 22, 24, 26 may correspond to non-mating surfaces 712, 714, 716, 718, 720 of the proximal femur 40 in FIGS. 14A-14B, respectively. That the tool indexing region 20 may include mating surfaces 700b, 701b, 702b, 704b that matingly receive, contact and index with corresponding mating surfaces 700a, 701a, 702a, 704a of the proximal femur 40 can be seen in FIG. 14A-14B, respectively. Also, that the tool over-estimated surfaces 22, 24, 26 extend over, but do not contact their corresponding non-mating surfaces 712, 714, 716 of the proximal femur 40 can be seen in FIG. 5E, with reference to FIGS. 14A-14B.

Although FIGS. 7A-9B are discussed with reference to FIG. 15, it can be appreciated that the same or similar methods of delineation of mating and non-mating regions and overestimation of non-mating regions may be utilized where needed with other non-mating regions that may be exposed during other surgical approaches, as discussed with respect to FIGS. 4, 14A-14B, and 16A-16B. Methods and processes for such overestimation are described in more detail in commonly-owned U.S. Patent Application No. 61/083,053, entitled System and Method for Manufacturing Arthroplasty Jigs Having Improved Mating Accuracy, filed Jul. 23, 2008, which is hereby incorporated by reference in its entirety.

As can be understood from FIG. 10, the CT scan discussed above may be reconstructed if necessary for proper coronal alignment, so that the coronal slices are parallel to the femoral neck 35. For this procedure, the slice width and overlap may range from approximately 0.5 mm to approximately 2 mm. In one embodiment, a slice width and overlap of 0.5 mm is used. The DFOV may range between approximately 16 cm to approximately 26 cm field of view. In one embodiment, the reformatted CT may include up to one-third of the proximal femur 40, including the femoral head 30 and the lesser trochanter 740.

As indicated in FIG. 11, from a coronal slice, the final reconstruction alignment 744 is set to an angle C relative to the long axis 746 of the femoral neck 35. Angle C may range from approximately 30 degrees to approximately 60 degrees. In one embodiment, angle C is 45 degrees. The slice width and overlap may range from approximately 0.5 mm to approximately 2 mm. In one embodiment, the slice width and overlap is 1 mm. The field of view may range from approximately 16 mm to approximately 26 mm. In one embodiment, the scan may include up to one-third of the proximal femur 40, including the femoral head 30 and the lesser trochanter 740.

Figure 12:
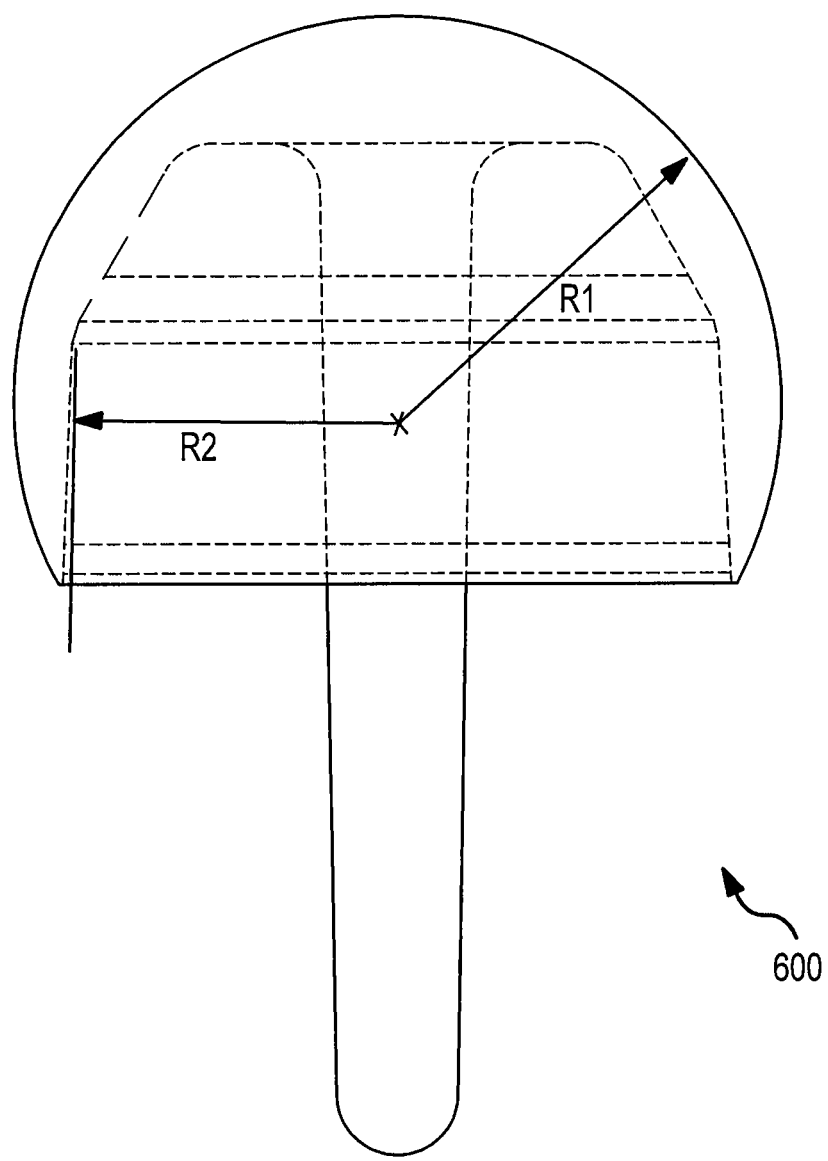
FIG. 12 is an embodiment of a femoral resurfacing component that may be used with the proximal femur of FIG. 5A during a hip resurfacing procedure.
Figure 13A:
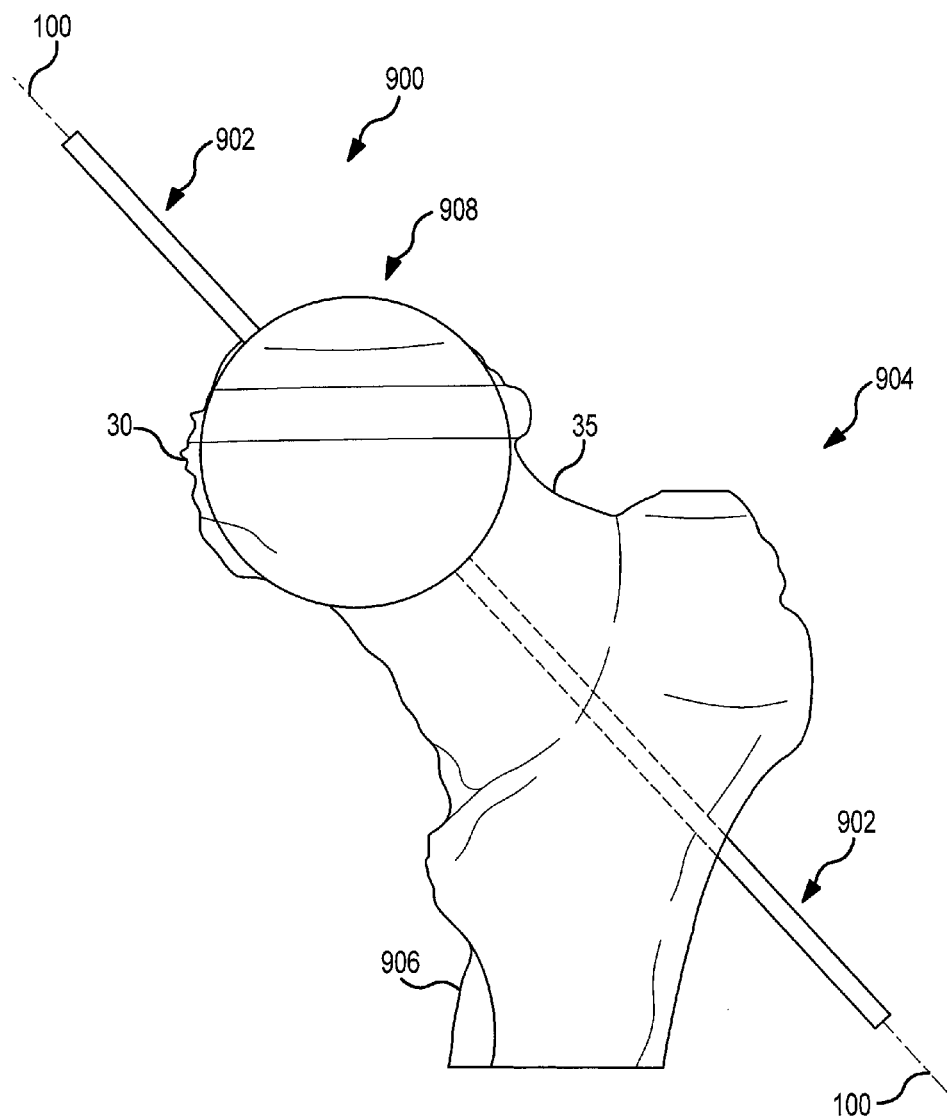
FIG. 13A is a posterior view of a model of the proximal femur of FIG. 5A, wherein a planning pin which may be used during pre-operative planning is shown.
Figure 13B:
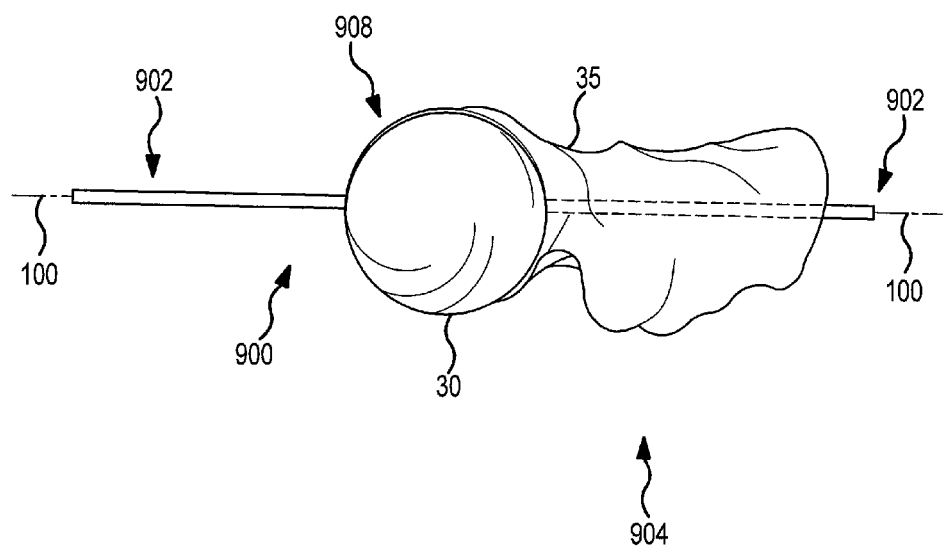
FIG. 13B is a superior view of the femur and planning pin of FIG. 13A.
Figure 13C:
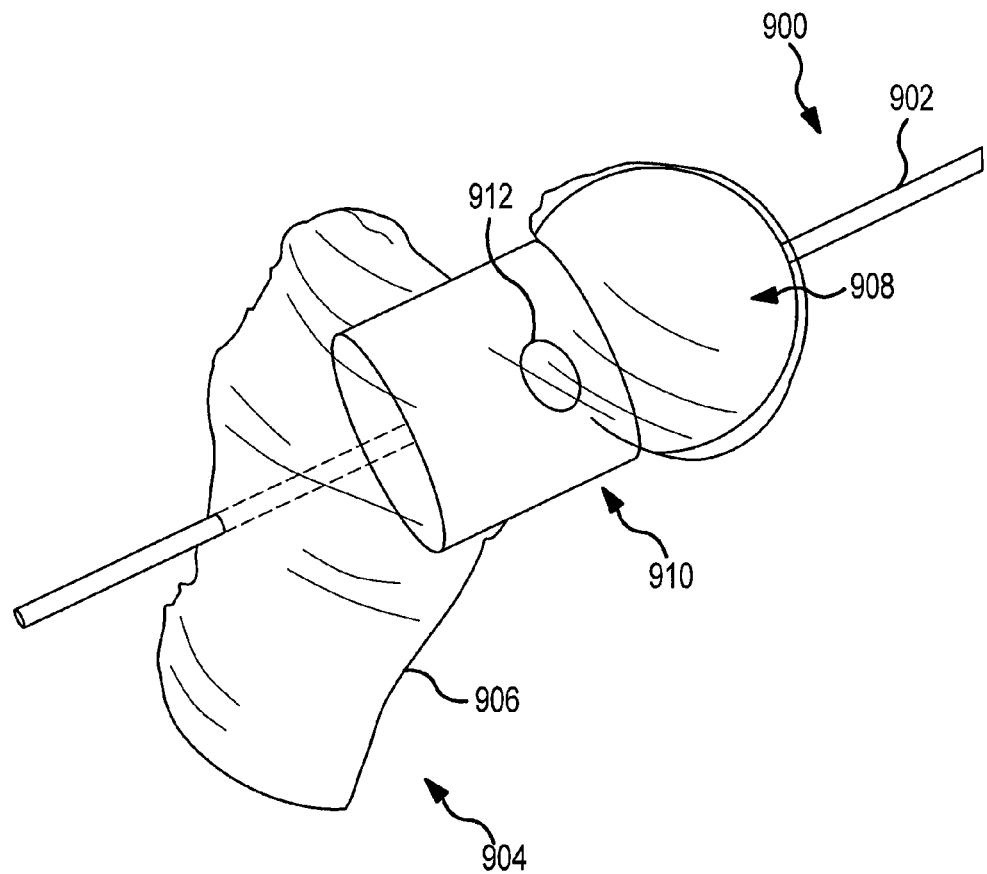
FIG. 13C is an anterior view of the proximal femur model of FIG. 5A, wherein the planning pin is shown in a position that may result in notching.
Figure 13D:
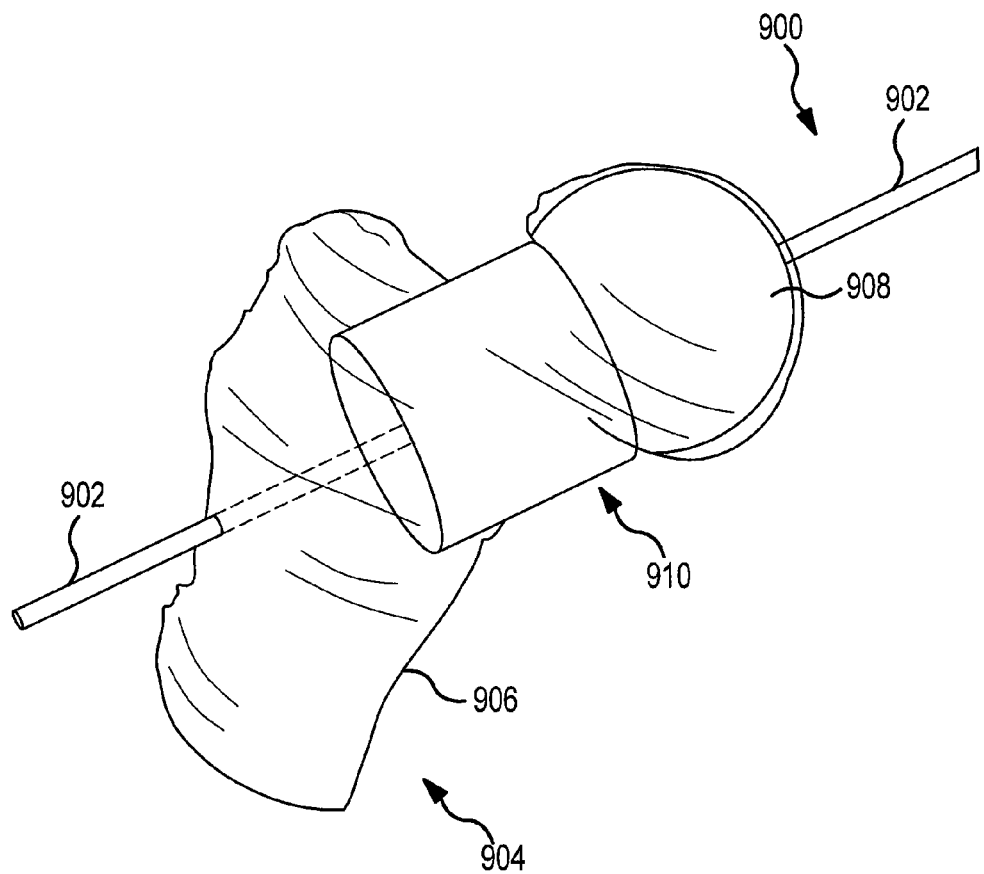
FIG. 13D is the same view as FIG. 13C, except the planning pin is in a position that may result in no notching.
Figure 13E:
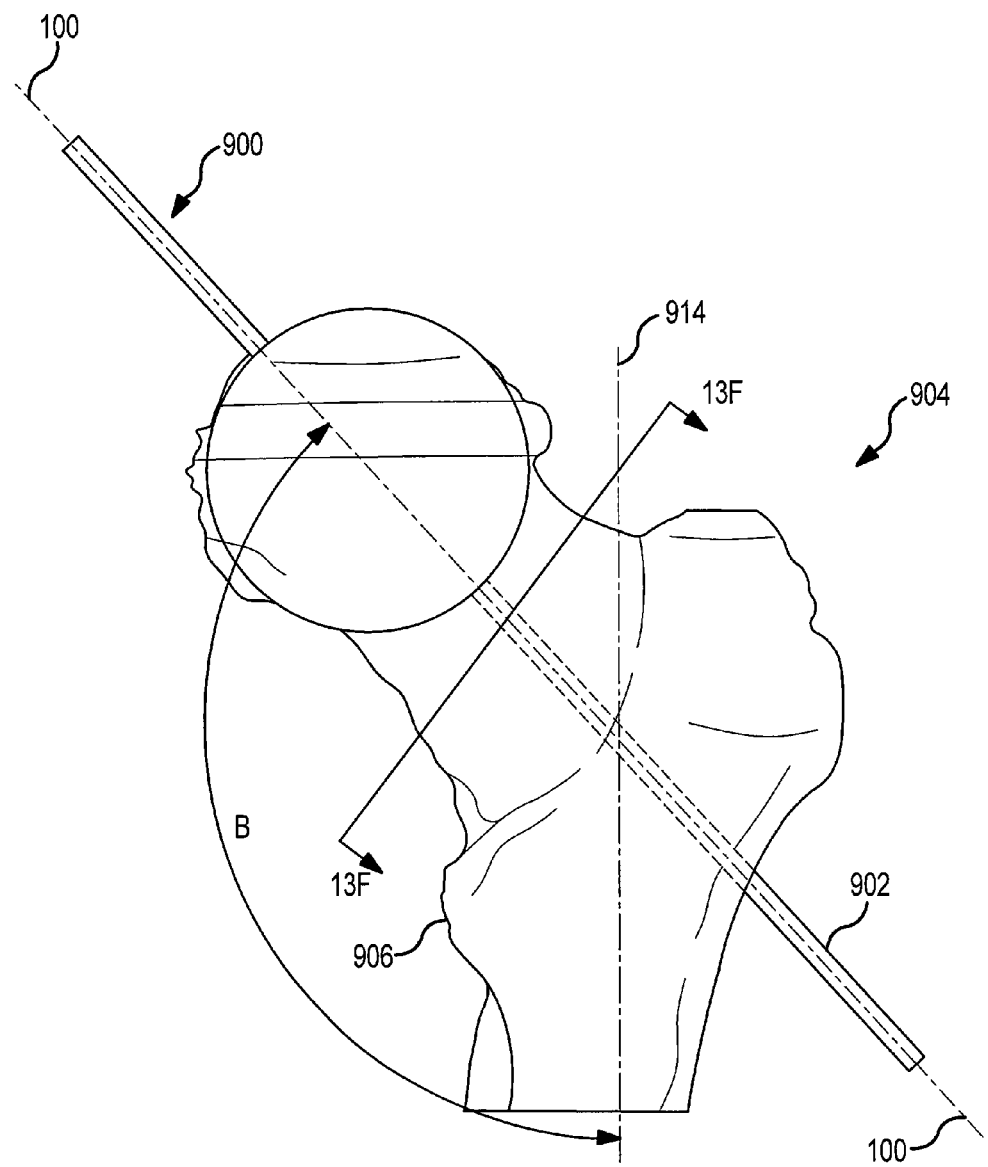
FIG. 13E is a posterior view of the model of the femur of FIG. 5A, wherein a guide wire and shaft of the femur are shown.
Figure 13F:
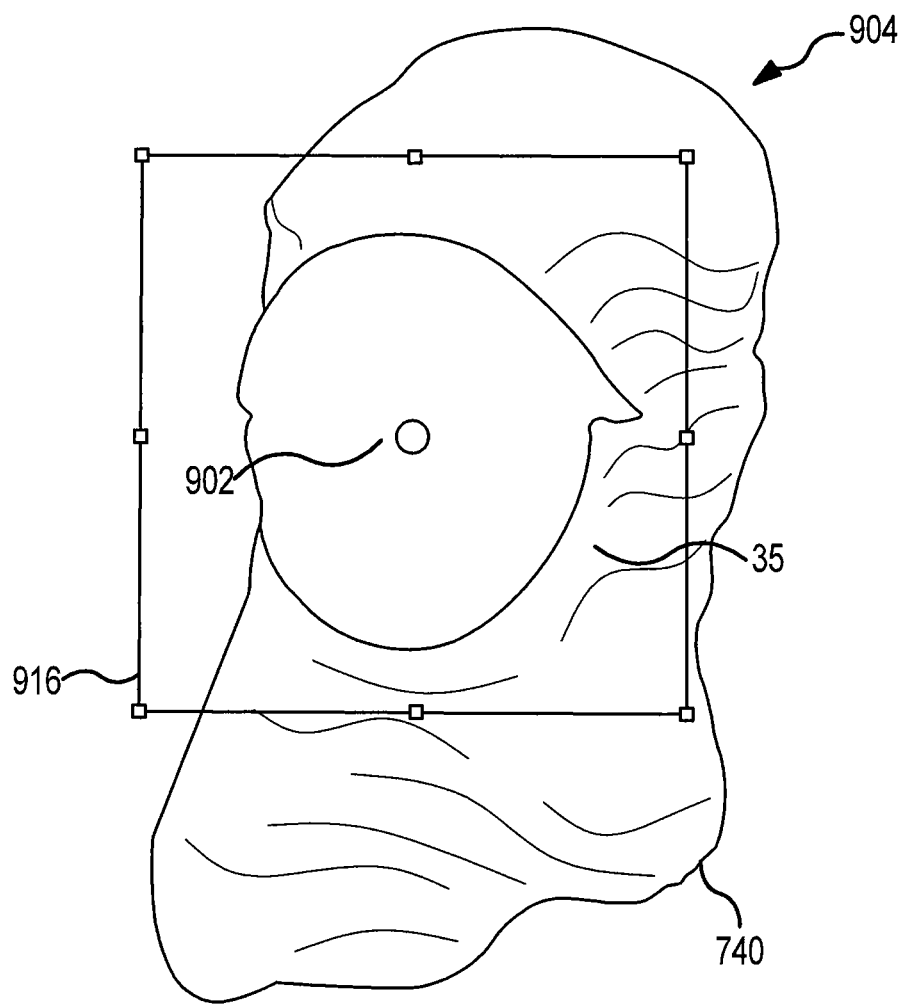
FIG. 13F is a cross-sectional elevation of the proximal femur as taken along section line 13F-13F of FIG. 13E.

For a discussion of one embodiment of the second portion of the process, reference is now made to FIGS. 12-13F. FIG. 12 is an embodiment of a femoral resurfacing component 600 that may be used with the proximal femur 40 of FIG. 5A during a hip resurfacing procedure. FIG. 13A is a posterior view of a model 904 of the proximal femur 40 of FIG. 5A, wherein a planning pin 900 which may be used during preoperative planning is shown. FIG. 13B is a superior view of a femur model 904 and planning pin 900 of FIG. 13A. FIG. 13C is an anterior view of the proximal femur 904 of FIG. 13A, wherein the planning pin 900 is shown in a position that may result in notching. FIG. 13D is the same view as FIG. 13C except the planning pin 900 is in a position that may result in no notching. FIG. 13E is a posterior view of the femur model 904 of FIG. 13A, wherein a guide wire 902 of the planning pin 900 and shaft 906 of the femur model 904 are shown. FIG. 13F is a cross-sectional elevation of the femur model 904 as taken along section line 13F-13F of FIG. 13E.

As can be understood from FIG. 1A, for the surgical planning step, the CT section scans are imported from the medical imaging machine 8 into a modeling program at a workstation 6 having a monitor 9, a user interface 11 and a CPU 7. With the aid of the modeling program, a 3D model 904 of the proximal femur 40 is created and may be displayed on the monitor 9. The surgical planning step can apply to a posterior approach, an anteriorlateral approach or a straight anterior approach. For the surgical planning step, the CT femur model 904 and a planning pin 900 are both provided and used to plan the alignment of the guide wire 75 [block 1502 and block 1604]. As can be understood from FIGS. 13A-13F, the planning pin 900 may include a guide wire model 902, a sphere 908 and a virtual barrel cut or cylinder 910. The planning pin 900 corresponds to a specific size of a resurfacing component 600. That is, the radius of the sphere 908 is equal to the outer radius R1 of the corresponding femoral resurfacing component 600 (as shown in FIG. 12). The radius of the virtual barrel cut 910 is equal to the inner cylindrical radius R2 of the femoral resurfacing component 600 (see FIG. 12).

Using 3D CAD software or 3D imaging software, the CT model of the femur 904 and planning pin 900 are opened together [block 1502]. Initially, and as can be understood from FIGS. 13A and 13B, the planning pin 900 is aligned so that it passes approximately through the center 100 of the femur model 904 in both posterior (FIG. 13A) and superior views (FIG. 13B) [block 1503]. This may be accomplished by simply visually analyzing the position of the guide wire 902 of the planning pin 900 relative to the femur neck and head from different views in a 3D computer environment such that the guide wire 902 appears to pass through the center of the femoral neck and head when viewed from the different views. In other embodiments, the guide wire 902 of the planning pin 900 may be caused to pass through the centroids 135 of transverse cross-sections 130 through the neck and head, as discussed above with respect to FIG. 3.

As shown in FIG. 13C, the virtual barrel cut 910 may be set to some level of transparency such that the pin 900 may be further aligned properly. As indicated in FIGS. 13A-13F, the sphere 908 of the planning pin 900 should be positioned such that it generally corresponds to the surface of the head 30 of the virtual femur model 904. Generally, if there is damage to the head, the damage is typically to the superior and anterior surfaces, so the sphere 908 is typically positioned to correspond to the inferior and posterior regions of the head. The size of the planning pin 900 may be increased or decreased as needed to more accurately fit the femur model 904 and, more specifically, to cause the sphere 908 of the planning pin 900 to correspond as needed to the femoral head.

As can be understood from FIGS. 13C and 13D, the position of the barrel cut 910 relative to the bone model is then checked to see if notching will occur. For this step, it may be necessary to increase the opacity of the barrel cut 910. Notching is indicated by a break 912 in the surface of the virtual barrel cut 910 (FIG. 13C). If notching occurs, the planning pin 900 may be rotated, translate or otherwise adjusted with respect to position or orientation relative to the femur model 904 to achieve a position where no notching occurs (as shown in FIG. 13D). During this realignment, the guide wire 902 of the planning pin 900 should still pass through the approximate center 100 of the neck 35 of the femur model 904. If such a position cannot be found, the size of the planning pin 900 may be increased or decreased as needed.

As shown in FIG. 13E, the angle between the shaft 906 of the femur 904 and the neck 35 may be measured in a posterior view of the femur model 904 by measuring the angle B between the guide wire model 902 of the planning pin 900 and the approximate long axis 914 of the femur. If this angle B is not sufficiently valgus, the planning pin 900 may be rotated about the center of its sphere 908 into a more valgus position, while ensuring that notching doesn't occur, and that the guide wire model 902 still passes through the approximate center 100 of the neck 35 in a superior view. As indicated in FIG. 13F, one or more cross sections 916 through the neck 35 may be used to inspect the position of the guide wire model 902 of the planning pin model 900. Thus, causing the surface of the sphere model 908 to correspond to the proper surface of the head 35 of the femur model 904 while both causing the guide wire model 902 to extend through the center of the neck of the femur model 904 and avoiding notching of the femur neck by the barrel cut 910, the resulting planning pin model 900 may be used to estimate the size of the resurfacing component 600 to be used in surgery. Further, the information regarding the orientation of the guide wire model 902 of the planning pin 900 may be utilized to properly align the tool 5. Specifically, the orientation of the guide wire model 902 may be used to define a desired reference axis 100 that may represent a drilling pathway through the patient's actual femur during the resurfacing procedure and which may be used in the preoperative planning to coordinate the mating surface models 539, 537 relative to the tool blank model 550 during the preoperative planning of the tool model 505 [block 1503].

The generation and placement of the mating surfaces 537, 539 on the tool blank model 550 may determined with the aid of a modeling computer program, such as Solidworks. For example, in one embodiment, a model 550 of a blank of the tool 5 is provided [block 1504]. In one embodiment, the tool blank model 550 may be imported into the models of the femur 904 and planning pin 900 or, alternatively, the femur model 904 and planning pin model 900 may be imported into the tool blank model 550. Thus, in the models and in use, the placement of the guide wire determines where the tool may be positioned on the femur. Since the guide hole 565 of the tool blank model 550 may be placed concentrically around the axis 100, the tool blank model 550 may then be free to rotate around the axis 100 to determine the correct mating regions of the femur to be imported into the tool blank model as mating surfaces for the tool model 505 to be generated and sent to the CNC machine.

In another embodiment, as indicated in FIG. 1C, the mating surface models 537, 539, which correspond to mating surfaces of the actual femur as discussed above and below with respect to FIGS. 4 and 14A-16B, are identified and defined [block 1502] and referenced both with respect to position and orientation relative to the axis 100 identified via the planning model 900 [block 1503]. The combined axis 100 and surface models 537, 539, which may be considered a referenced set of data, may then be imported into the tool blank model 550 such that the axis 100 is coaxial with axis of the guide hole 565 of the blank model 550 or, alternatively, the blank model 550 may be imported into the combined axis 100 and surface models 537, 539 and aligned in the same fashion [block 1505].

The surface models 537, 539 are then used to form mating regions of the tool model 505, the mating regions of the tool model 505 being positionally and orientationally referenced to the axis of the guide hole 565 such that when the mating regions matingly receive the corresponding femur mating surfaces, the guide hole 565 will be generally coaxially aligned with the desired axis 100 extending through the femoral head and neck [block 1506]. As can be understood from FIGS. 1A, 1C and 1D, after the tool model 505 is designed, the tool model 505 may be used to create manufacturing instructions, which are sent to a manufacturing device 10, such as, for example, a CNC machine or SLA, that forms an actual physical customized tool 5 of FIG. 5C from an actual physical tool blank 250 [blocks 1507, 1606 and 1608]. In one embodiment, the tool manufacturing instructions or tool paths may be generated from the tool model 505 via Visual Mill or Cam Works.

Post processing of the tool may include cutting the tool away from the struts and smoothing around the edges. The tool 5 may then be packaged and sent to the surgeon [block 1610]. During surgery, the surgeon fits the tool 5 to the patient's femur such that the mating region matingly receives the corresponding region of the patient's femur, the mating surfaces of the tool mating region matingly contacting the corresponding femur mating surfaces, the non-mating surfaces of the tool mating region being spaced apart from the corresponding non-mating surfaces of the femur so as to not contact the femur non-mating surfaces, and the axis of the guide hole being generally coaxial with a predetermined desired axis extending through the femoral head and neck [block 1612]. Once the tool 5 matingly receives the femur and is secured thereto, the guide rod is placed in the guide hole and the guide rod is used to guide the drilling of a hole along the axis of the femur in preparation for the insertion of the guide wire into the drilled hole [block 1618]. Once the guide wire is in the drilled hole, the tool may be removed and discarded [block 1620]. The resurfacing device can then be applied to the femoral head and guided during its operation via the guide wire.

Generation of the above described mating region models 537, 539 used in the generation of the tool model 505 and corresponding to the mating surfaces discussed above and below with respect to FIGS. 4 and 14A-16B may also be determined with the aid of a modeling computer program, such as Solidworks.

2. Potential Mating Regions

For a discussion of the mating surfaces of an alternative embodiment of a hip resurfacing surgical guide tool 5, reference is now made to FIGS. 14A-16B. As can be understood from FIGS. 14A-16B, depending on the approach (e.g., posterior approach, anteriorlateral approach, straight anterior approach, etc.), there are several different potential mating and non-mating surfaces. As shown in FIGS. 14A-14B, in one embodiment, for use in a posterior or anteriorlateral approach, mating surfaces 700a, 701a, 702a 704a of the mating region 20 of the tool 5 may help to stabilize the positioning of the tool 5. A first mating surface 700a includes portions of the posterior region 724 of the neck 35, having a medial starting point between approximately 1 mm and approximately 5 mm after the cartilage covering the femoral head 30 terminates laterally and extends laterally between approximately 15 mm and approximately 35 mm to or towards the trochanteric fossa 210. The inferior border of the first mating surface 700a begins approximately midway superiorly-inferiorly along the intertrochanteric crest 116, and follows the long axis of the neck 35. The superior border of the first mating surface 700a is between approximately 1 mm and approximately 3 mm below the superior junction 728 between the posterior and anterior surfaces of the neck 35. A second mating surface 701a has approximately the same medial-lateral width as section 700a, but may terminate before the tubercle 730 of the femur 40. The superior border of the second mating surface 701a is approximately 1 mm to approximately 3 mm below the superior junction 728 between the posterior and anterior surfaces of the neck 35. The inferior-superior distance of second mating surface 701a is between 5 and 10 mm. A third mating surface 702a is a narrow band, measuring generally medial-lateral between approximately 0.5 mm and approximately 8 mm, that follows along the intertrochanteric crest 116. Mating surface 702a begins approximately midway superior-inferior along the intertrochanteric crest 116 and may extend any length greater than approximately 5 mm to or towards the most superior tip 215 of the posterior surface of the greater trochanter 115. A fourth mating surface 704a lies on the anterior greater trochanter 115, lateral to the tubercle 730 of the femur 40, and inferior to the origin of the obturator internus 732. The medial-lateral distance of mating surface 704a measures between approximately 3 mm to approximately 14 mm, and its inferior-superior distance measures between approximately 3 mm to approximately 10 mm.

As indicated in FIGS. 14A-14B, mating surfaces 700a, 701a, 702a, 704a may be separated by non-mating surfaces 712, 714, 716 that are spanned by and correspond respectively with non-contacting surfaces 22, 24, 26 of the mating region 20 of the tool 5. A first non-mating surface 712 may include portions of the tubercle 730 of the femur 40. A second non-mating surface 714 may span portions of the trochanteric fossa 210. A third non-mating surface 716 may contain the superior junction 728 between the posterior and anterior surfaces of the neck 35, and may be between approximately 1 mm to approximately 5 mm anterior-posterior. As described in more detail above, and with reference to FIGS. 7A-9B, during segmentation, contour line portions corresponding to non-mating surfaces 712, 714, 716 may be overestimated (e.g., moved outward from the interior of the bone and smoothed) such that portions of the tool mating region 20 defined according to those overestimated contour line portions are over-machined, ensuring that little or no contact occurs between the resulting non-mating surfaces 22, 24, 26 of the mating region 20 of the tool 5 and the corresponding non-mating surfaces 712, 714, 716 of the bone when the tool mating region 20 matingly receives the region of the bone having the non-mating surfaces 712, 714, 716.

In other embodiments, as shown in FIG. 15, other mating surfaces 708, 710 may be available in a posterior approach to help with stable positioning of the tool 5 on the femur 40. A first mating surface 708 covers portions of the posterior region of the neck 35, starting medially between approximately 1 mm and approximately 5 mm after the cartilage covering the head 30 of the femur 40 terminates laterally and laterally extends between approximately 15 mm and approximately 35 mm to or towards the trochanteric fossa 210. The inferior boundary of surface 708 may terminate approximately 5 mm superior to the inferior border between the posterior and anterior surfaces of the neck 35, or may extend up to approximately 5 mm anterior past this border. The superior boundary of mating surface 708 may extend approximately 0 mm to approximately 5 mm posterior to the superior junction between the posterior surface and the anterior surface of the neck 35. A second mating surface 710 may be a narrow band measuring between approximately 0.5 mm and approximately 12 mm medial-lateral. The second mating surface 710 may follow along the intertrochanteric crest 116. Mating surface 710 may begin approximately 0 mm to approximately 12 mm superior to the lesser trochanter 740 and may extend approximately 0 mm to approximately 18 mm inferior to the most superior tip 215 of the posterior surface of the greater trochanter 115.

As indicated in FIG. 15, non-mating surfaces 718, 720 are spanned by non-contacting surfaces 22, 24, 26 of the tool 5. A first non-mating surface 718 may include portions of the posterior greater trochanter 115 and extend superior-inferior adjacent the intertrochanteric crest 116. The medial boundary of the first non-mating surface 718 may be the second mating surface 710, and may extend medial-lateral approximately 0 mm to approximately 12 mm. The second non-mating surface 720 may span portions of the trochanteric fossa 210, and may have a medial boundary that is the first mating surface 708 and a lateral boundary that is the second mating surface 710, and a medial-lateral width that may vary between approximately 0 mm and approximately 20 mm. Both the first non-mating surface 718 and the second non-mating surface 720 may have inferior-superior dimensions similar to the first mating surface 708 and the second mating surface 710. During segmentation, contour line portions corresponding to non-mating surfaces 718, 720 and osteophytes 742 may be overestimated (e.g., moved outward from the interior of the bone and smoothed) such that portions of the tool mating region 20 defined according to those overestimated contour line portions are over-machined, ensuring that little or no contact occurs between the resulting non-mating surfaces of the mating region 20 of the tool 5 and the corresponding non-mating surfaces 718, 720 of the bone when the tool mating region 20 matingly receives the region of the bone having the non-mating surfaces 718, 720.

Figure 16A:
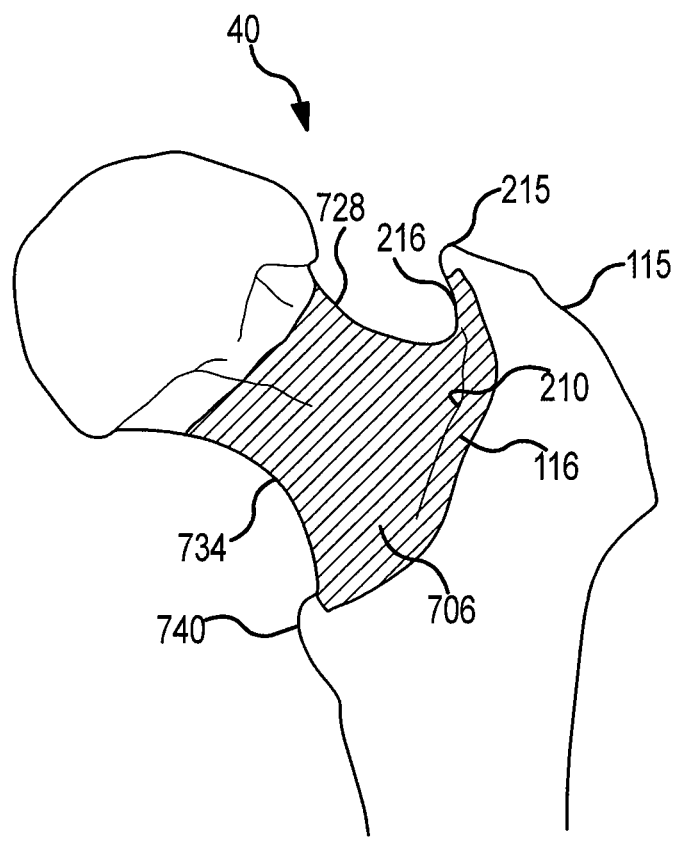
FIG. 16A is a posterior view of the proximal femur of FIG. 5A showing the surfaces of the femur that are mated with the index surfaces of still another embodiment of the tool.
Figure 16B:
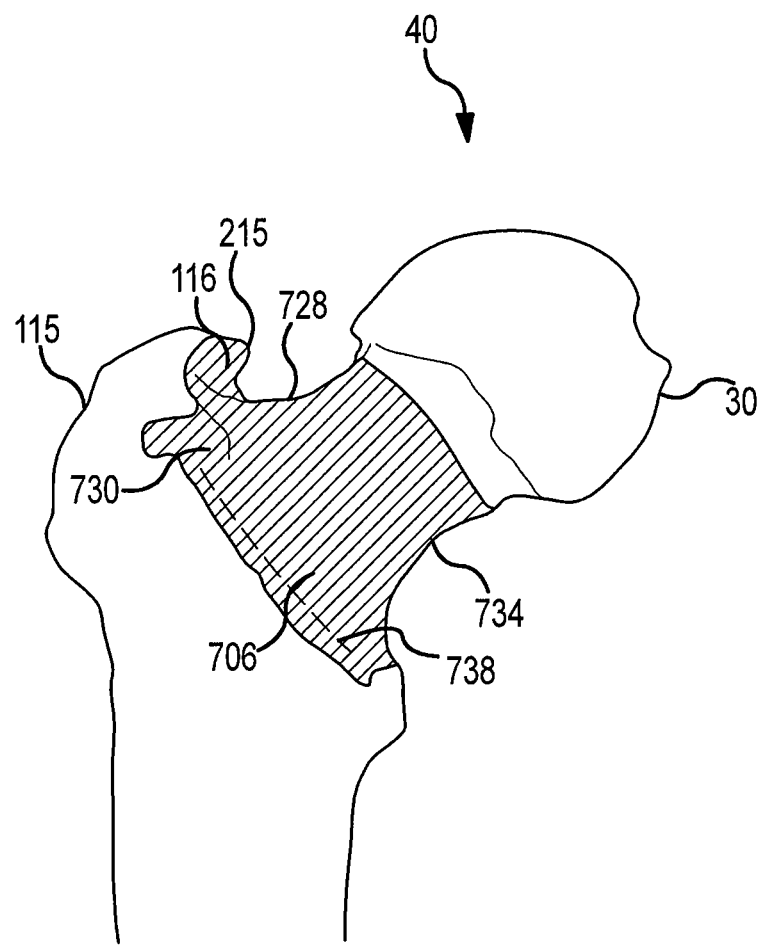
FIG. 16B is an anterior view of FIG. 16A.

In other embodiments, as shown in FIGS. 16A-16B, for use with any approach, a first mating surface 706 of the femur 40 may include the entire or any portion of the circumferential surface 734 of the neck 35. On the posterior surface, the mating surface 706 may start medially between approximately 1 mm and approximately 5 mm after the cartilage covering the head 30 of the femur 40 terminates laterally and extend laterally up to approximately 8 mm past the intertrochanteric crest 116, extending along the intertrochanteric crest 116 from the lesser trochanter 740 to or towards the tip 215 of the greater trochanter 115. On the anterior surface, the mating surface 706 may start medially between approximately 1 mm and approximately 5 mm after the cartilage covering the head 30 of the femur 40 terminates laterally and extend laterally up to approximately 8 mm laterally past the intertrochanteric line 738. The surface 706 may also contain the medial surface of the greater trochanter 115. As discussed above, portions within the mating surface 706 may be overestimated if geometry is too erratic for the surface to be accurately captured with the CT scan. Some such areas may include the trochanteric fossa 210, the superior junction 728 between the posterior and anterior surfaces of the neck 35, and the tubercle 730.

3. Method of Manufacture and Use

For a general discussion of a method of manufacturing and using the tool, reference is now made to FIGS. 1A, 1C and 1D. FIG. 1C is a diagrammatic depiction of a process of manufacturing some embodiments of the tool 5. As can be understood from FIGS. 1A, 1C and 1D, in one embodiment, a process for producing the tool 5 may be as follows. CT image scans 500 of the joint 14 of the patient 12 are generated via the CT machine 8 and sent to the modeling system 6 [block 1500 and block 1600]. Each image scan 500 may have a femur contour line 502 that is identified via an image segmentation process [block 1602]. Where the contour lines 502 have portions corresponding to regions of the femur contour that have rapidly changing geometry, the portions of the contour lines 502 may be subjected to an overestimation process wherein the portions of the contour lines may be moved outwardly into a smoothed, outwardly enlarged, and less erratic contour. The scans 500, which may be a combination of scan images with contour lines with no overestimation and scan images with contour lines having overestimated portions, are compiled into a 3D bone model 904 of the proximal femur via a 3D computer modeling program loaded on the modeling system 6. The preoperative planning may begin with the bone model 904 may be analyzed to determine the central axis 100 through the femur neck and head [block 1604]. For example, the planning pin model 900 and bone model 904 may be superimposed to identify the appropriate size of the resurfacing component 600 and to identify the desired axis 100 through the femoral neck and head [block 1502 and block 1503]. A tool blank model 550 is provided [block 1504]. The bone model 904 may also be analyzed to determine indexing or mating surfaces 537, 539 that will be imported into the tool blank model 550 and be used to form the indexing surfaces of the mating region 20 of the actual tool 5 [block 1502]. In one embodiment, the surfaces 537, 539 and the axis 100, as may be determined by the centroid method and proper alignment of the planning pin model 900, may be imported into the tool blank model 550 such that the axis 100 aligns with the guide hole 565 in the blank model 550, thereby creating a tool model 505 [blocks 1505 and 1506]. The tool model 505 may be used to create milling tool paths that are sent to the CNC machine 10 [block 1507]. The CNC machine 10 uses the milling paths to generate the tool 5 from an actual tool blank 250 [block 1606 and block 1608]. The finished tool 5 is packaged and sent to the surgeon [block 1610].

Upon receipt of the tool and as can be understood from FIG. 1D, the following surgical process may be utilized. During surgery, the surgeon may fit the tool appropriately on the femur 40, stabilize the tool 5 and in one embodiment, drill into the femoral head through the drill hole [block 1612]. In some embodiments, the tool 5 may be held in place by the surgeon or other medical personnel. Once positioned, the surgeon may place a guide wire or rod through the guide hole and into the hole drilled in the femoral head and neck [block 1618]. With the guide wire or rod in place, the tool may be discarded [block 1620]. The surgeon may then use the guide wire or rod to guide the resurfacing of the femoral head in preparation for receiving the resurfacing component 600 chosen during the planning step.

The preoperative planning and resulting customized tool 5 offers a number of benefits. First, there is an increase in the accuracy associated with the resurfacing process. Second, there is an increase in the accuracy in the alignment and fit associated with the resurfacing implant 600. Third, there is a decrease in the risk associated with drilling a hole through the axis of the femoral head and neck.

While the above disclosed embodiments of a arthroplasty jig or surgical guide tool are described in the context of a jig or tool 5 for use in a hip resurfacing procedure and for certain surgical approaches, the features, methods of planning, manufacture and use disclosed herein may be equally useful and applicable for other types of arthroplasty procedures and/or other types of joints. Thus, the disclosure provided herein should be considered as encompassing jigs and the generation thereof for any arthroplasty procedure for any type of joint.

Although the present invention has been described with reference to preferred embodiments, persons skilled in the art will recognize that changes may be made in form and detail without departing from the spirit and scope of the invention.

What is claimed is:

1. A surgical guide tool for use in hip resurfacing surgery on a proximal portion of a femur having a head, a neck extending distally from the head, a surface region distal the head, a bone axis extending through centers of the head and neck, a superior-posterior region of the neck including a narrow band that follows along an intertrochanteric crest, a superior-anterior region of the neck, a cartilage covering the head, a tubercle, an anterior greater trochanter, an origin of a obturator internus, a superior junction between the posterior and anterior surfaces of the neck, and a trochanteric fossa, the tool comprising:
   a body including a guide hole and a mating region configured to matingly contact the surface region, the guide hole including a hole axis, the guide hole and mating region being positioned relative to each other so the hole axis is generally coaxially aligned with the bone axis when the mating region matingly contacts the surface region, wherein the mating region is generally an identical negative shape of the surface region that includes:
   a first area that includes the at least a portion of the superior-posterior region of the neck including the narrow band that follows along the intertrochanteric crest and has the medial-lateral width of between approximately 0.5 mm and approximately 8 mm;
   a second area that includes the at least a portion of the superior-anterior region of the neck starting between approximately 1 mm and approximately 5 mm after the cartilage covering the head terminates distally and extending between approximately 15 mm and approximately 35 mm to terminate before the tubercle; and
   a third area that includes the region on the anterior greater trochanter, distal to the tubercle, and inferior to the origin of the obturator internus;
   wherein the first area, the second area, and the third area are each separated by points of non-contact between the mating region and the surface region.

2. The tool of claim 1, wherein the first area and the second area are separated by a first point of non-contact between the mating region and the surface region, the first point including the superior junction between the posterior and anterior surfaces of the neck.

3. The tool of claim 2, wherein the second area and the third area are separated by a second point of non-contact between the mating region and the surface region, the second point including the tubercle.

4. The tool of claim 1, wherein the surface region further includes a fourth area including an area that extends along the intertrochanteric crest.

5. The tool of claim 4, wherein the first area and the fourth area are separated by a third point of non-contact between the mating region and the surface region, the third point including an area that spans portions of the trochanteric fossa.

* * * * *